(12) United States Patent
Garner

(10) Patent No.: US 8,981,049 B2
(45) Date of Patent: Mar. 17, 2015

(54) AZIRIDINE MEDIATED NATIVE CHEMICAL LIGATION

(71) Applicant: Washington State University, Pullman, WA (US)

(72) Inventor: Philip Garner, Pullman, WA (US)

(73) Assignee: Washington State University, Pullman, WA (US)

(*) Notice: Subject to any disclaimer, the term of this patent is extended or adjusted under 35 U.S.C. 154(b) by 151 days.

(21) Appl. No.: 13/675,524

(22) Filed: Nov. 13, 2012

(65) Prior Publication Data

US 2013/0131311 A1  May 23, 2013

Related U.S. Application Data

(60) Provisional application No. 61/561,520, filed on Nov. 18, 2011.

(51) Int. Cl.

| | | |
|---|---|---|
| C07K 1/00 | (2006.01) | |
| C07K 1/107 | (2006.01) | |
| C07K 5/04 | (2006.01) | |
| C07K 7/64 | (2006.01) | |
| C07K 14/00 | (2006.01) | |
| C07K 9/00 | (2006.01) | |
| C07K 5/062 | (2006.01) | |
| C07K 7/06 | (2006.01) | |
| C07K 5/083 | (2006.01) | |
| C07K 1/04 | (2006.01) | |
| C07K 1/12 | (2006.01) | |
| C07K 5/103 | (2006.01) | |
| C07K 1/02 | (2006.01) | |
| C07K 5/11 | (2006.01) | |
| C07K 5/113 | (2006.01) | |

(52) U.S. Cl.
CPC .............. *C07K 1/00* (2013.01); *C07K 14/001* (2013.01); *C07K 7/64* (2013.01); *C07K 9/001* (2013.01); *C07K 5/0606* (2013.01); *C07K 7/06* (2013.01); *C07K 5/081* (2013.01); *C07K 1/04* (2013.01); *C07K 1/12* (2013.01); *C07K 5/1013* (2013.01); C07K 1/026 (2013.01); C07K 5/1019 (2013.01); C07K 5/1021 (2013.01)
USPC ........... 530/321; 530/300; 530/333; 530/336; 536/17.9

(58) Field of Classification Search
CPC .......... C07K 1/00; C07K 1/001; C07K 1/107; C07K 1/1072; C07K 2/00; C07K 5/081; C07K 5/0606; C07K 5/1013; C07K 5/1005; C07K 5/1072
See application file for complete search history.

(56) References Cited

U.S. PATENT DOCUMENTS 7,323,608 B2 *  1/2008  Buchwald et al. ............ 570/181

OTHER PUBLICATIONS

Kirk-Othmer, Encyclopedia of Chemical Technology, 4th Edition, vol. 14, 1995.*
Forbeck, A Regio- and Stereoselective Approach to Quaternary Centers from Chiral Trisubstituted Aziridines, Journal of the American Chemical Society 129:14463-14469, 2007.*
Dewick, "Nucleophilic Reactions of Carbonyl Groups" in Essentials of Organic Chemistry, John Wiley & Sons, Jun. 13, 2006.*
Assem et al., JACS Communications (2010) 132, 10986-10987.*
Galonic, JACS (2005) 127, 7359-7369.*
Namelikonda et al., Chem. Commun (2012, first published online Sep. 2011) 48, 1526-1528.*
Allen et al., Chem. Soc. Rev. (Mar. 2011) 40, 3405-3415.*
Rotstein et al.; "Synthesis of peptide macrocycles using unprotected amino aldehydes"; Nature Protocols, vol. 5, No. 11, 2010, pp. 1813-1822.
Galonic et al.; "Aziridin-2-carboxylic Acid-Containing Peptides: Application to Solution- and Solid-Phase Convergent Site-Selective Peptide Modification"; Journal of the American Chemical Society, vol. 127, No. 20, 2005, pp. 7359-7369.
Assem et al.; "Chemoselective Peptidomimetic Ligation Using Thioacid Peptides and Aziridine Templates"; Journal of the American Chemical Society, vol. 132, No. 32, 2010, pp. 10986-10987.
Weiss et al.; "Covalent HLA-B27 / peptide complex induced by specific recognition of an aziridine mimic of arginine"; Proceedings of the National Academy of Science, vol. 93, Oct. 1996, pp. 10945-10948.
Shao et al.; "Tilted amides in amino acid and peptide derivatives"; Chemistry & Biology 1994, vol. 1, No. 4, pp. 231-234.

* cited by examiner

*Primary Examiner* — Karlheinz R Skowronek
*Assistant Examiner* — Catherine Mader
(74) *Attorney, Agent, or Firm* — Whitman Curtis Christofferson & Cook, PC

(57) ABSTRACT

Improved methods of native chemical ligation are provided. The methods involve reacting a thioacid (e.g. a peptide thioacid) with an aziridinyl compound (e.g. an aziridinyl peptide) under mild conditions without the use of protecting groups, and without requiring that a cysteine residue be present in the ligation product. Initial coupling of the thioacid and the aziridinyl compound yields a ligation product which contains an aziridinyl ring. Subsequent opening of the aziridinyl ring (e.g. via a nucleophilic attack) produces a linearized and modified ligation product.

7 Claims, 2 Drawing Sheets

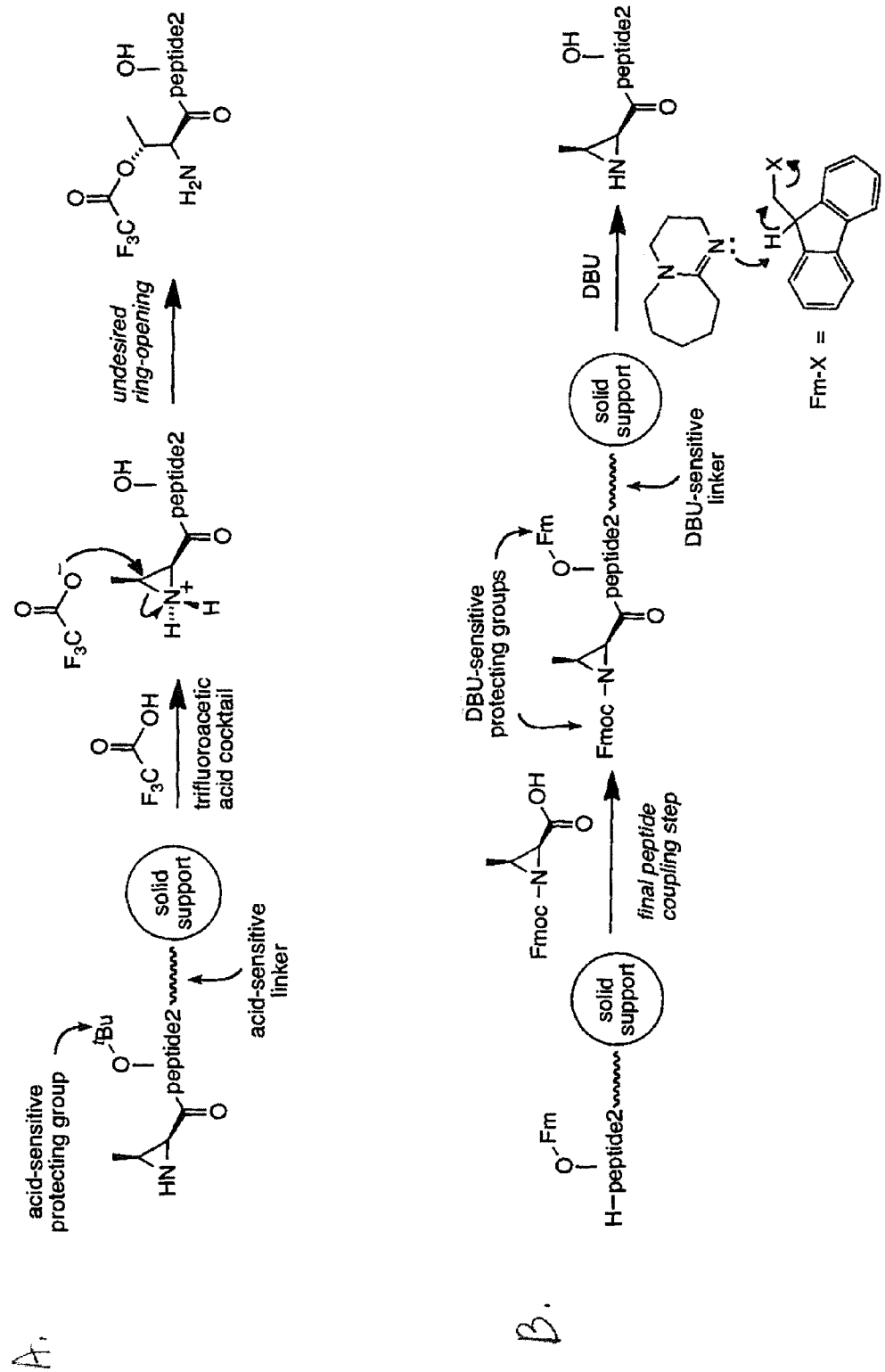
Figure 2A and B

ND NATIVE CHEMICAL LIGATION

SEQUENCE LISTING

```
<160> NUMBER OF SEQ ID NOS: 16

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Carboxy terminus is benzylated

<400> SEQUENCE: 1

Lys Tyr Thr Thr
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Carboxy terminus is benzylated

<400> SEQUENCE: 2

Glu Tyr Thr Thr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Carboxy terminus is benzylated

<400> SEQUENCE: 3

Cys Tyr Ala Thr
1

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Lys Tyr Thr Thr Phe Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Gln Tyr Thr Thr Phe Gly
1               5
```

-continued

```
<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Aziridine is between resideus 3 and 4

<400> SEQUENCE: 6

Lys Tyr Thr Phe Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Aziridine is between residues 3 and 4

<400> SEQUENCE: 7

Glu Tyr Thr Phe Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Leu Tyr Arg Ala Met Phe Arg Ala Gln Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Palmitoyl is attached to residue 5
<220> FEATURE:
<221> NAME/KEY: MISC_FEATURE
<222> LOCATION: (10)..(10)
<223> OTHER INFORMATION: Farnesyl is attached to residue 10

<400> SEQUENCE: 9

Gly Thr Asn Gly Cys Met Gly Leu Pro Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Thr at position 6 is phosphorylated
```

```
<400> SEQUENCE: 10

Leu Glu Thr Val Ser Thr Gln Glu Leu Tyr Cys
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Amino terminus contains aziridine

<400> SEQUENCE: 11

Pro Gly Cys Val Ala
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Carboxy terminus is sulfated

<400> SEQUENCE: 12

Pro Ala Ile Ala Ile Leu Ala Ala Tyr Ile
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Amino terminus contains aziridine
<220> FEATURE:
<221> NAME/KEY: MISC_FEATURE
<222> LOCATION: (4)..(4)
<223> OTHER INFORMATION: Carboxy terminus contains sulfated tetramethyl
      benzidine

<400> SEQUENCE: 13

Thr Asn Thr Cys
1

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (11)..(15)
<220> FEATURE:
<221> NAME/KEY: MISC_FEATURE
<222> LOCATION: (15)..(15)
<223> OTHER INFORMATION: Carboxy terminus is sulfataed

<400> SEQUENCE: 14
```

```
Pro Ala Ile Ala Ile Leu Ala Ala Tyr Ile Ala Thr Asn Thr Ala
1               5                   10                  15

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (11)..(15)
<220> FEATURE:
<221> NAME/KEY: DISULFID
<222> LOCATION: (16)..(19)
<220> FEATURE:
<221> NAME/KEY: MISC_FEATURE
<222> LOCATION: (16)..(16)
<223> OTHER INFORMATION: Residue 16 is aminobutonoic acid
<220> FEATURE:
<221> NAME/KEY: MISC_FEATURE
<222> LOCATION: (19)..(19)
<223> OTHER INFORMATION: Carboxy terminus is sulfated

<400> SEQUENCE: 15

Pro Ala Ile Ala Ile Leu Ala Ala Tyr Ile Ala Thr Asn Thr Ala Ser
1               5                   10                  15

Xaa Thr Lys Ala
            20

<210> SEQ ID NO 16
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (11)..(15)
<220> FEATURE:
<221> NAME/KEY: DISULFID
<222> LOCATION: (16)..(19)
<220> FEATURE:
<221> NAME/KEY: MISC_FEATURE
<222> LOCATION: (16)..(16)
<223> OTHER INFORMATION: Residue 16 is aminobutanoic acid
<220> FEATURE:
<221> NAME/KEY: DISULFID
<222> LOCATION: (20)..(23)
<220> FEATURE:
<221> NAME/KEY: MISC_FEATURE
<222> LOCATION: (20)..(20)
<223> OTHER INFORMATION: Residue 20 is aminobutanoic acid

<400> SEQUENCE: 16

Pro Ala Ile Ala Ile Leu Ala Ala Tyr Ile Ala Thr Asn Thr Ala Xaa
1               5                   10                  15

Thr Lys Ala Xaa Arg Ala Ala
            20
```

AZIRIDINE MEDIATED NATIVE CHEMICAL LIGATION

CROSS-REFERENCE TO RELATED APPLICATIONS

This application claims benefit of U.S. provisional patent application 61/561,520, filed Nov. 18, 2011, the complete contents of which is hereby incorporated by reference.

SEQUENCE LISTING

This application includes as the Sequence Listing the complete contents of the accompanying text file "Sequence.txt", created Nov. 9, 2012, containing 4096 bytes, hereby incorporated by reference.

DESCRIPTION

Background of the Invention

1. Field of the Invention

The invention generally relates to improved methods of native chemical ligation. In particular, the invention provides methods of ligating a peptide thioacid and an aziridinyl peptide to yield an aziridinyl peptide ligation product without the use of protecting groups, and without requiring the inclusion of a cysteine residue. Nucleophilic ring opening of the ligation product yields a linearized peptide ligation product.

2. Background of the Invention

The process of native chemical ligation (NCL)[1] involves the chemoselective coupling of unprotected thioesters (Group A) (Group B) via an intramolecular S— to N-acyl transfer to give products of the type A-Cys-B, wherein Cys represents the amino acid residue cysteine.

NCL was a significant achievement because it enabled the synthesis of large peptides and proteins ("protein semisynthesis") under very mild reaction conditions. A key feature of NCL is that it does not require the use of protecting groups and thus represents a particularly powerful approach to specifically modified proteins. The prototypical NCL process is characterized by the chemoselective coupling of "Group A", an unprotected peptide thioester (e.g. peptide1-Xaa-SR) and a "Group B" amino functionalized compound bearing a branched side chain that includes a removable thiol auxiliary, e.g. an unprotected cysteinyl peptide (H-Cys-peptide2). The resulting ligation product is A-Cys-B, where Cys represents the amino acid residue cysteine. If the reactants are peptides, the ligation product has the general structure peptide1-Xaa-Cys-peptide2.

The rate-determining step for NCL has been shown to be transthioesterification of the peptide thioester by the Cys thiol.[2] Unfortunately, since an N-terminal Cys residue is required,[3] and since the frequency of occurrence of Cys in proteins (1.82%) is low, NCL-based strategies are rather limited, e.g. to ligation at peptide linkages Xaa-Cys, where Xaa is preferably an unhindered amino acid. It follows that the incorporation of post-translationally modified or unnatural amino acids at the ligation site is not feasible with NCL.

The lack of generality and coupling efficiency represent significant gaps in the existing NCL technology repertoire.

Shao et al. (Chemistry & Biology 1994 (1) 4:231-234) describe aziridine containing peptides. However, the peptides were synthesized by conventional methods using protecting groups.

Rotstein et al. (Nature Protocols 2010 (5) 11: 1813-22) describe the synthesis of peptides that contain an aziridine ring which can be modified by ring opening. However, the method employs aziridine aldehydes, and the peptides are all macrocyclic and the products do not have a natural peptide backbone.

Weiss et al., (PNAS 1996. 93:10945-10948) describe the synthesis of an azirdine-containing peptide. However, the peptide is an arginine mimic and the aziridine is present on a side chain of the peptide.

Assem et al., (J. Am. Chem. Soc. 2010, 132, 10986-10987), describes chemoselective peptidomimetic ligation using thio-acid peptides and aziridine templates. However, the peptide with the aziridine employs protecting groups, and the resulting peptides necessarily contain an SH group, unless removed by a step of desulfurization. Further, the linkage formed is not an alpha-peptide but a beta-peptide.

Galonic et al, (J. Am. Chem. Soc. 2005, 127, 7359-7369), describe aziridine-2-carboxylic acid-containing peptides. However, the synthesis method employs conventional protecting groups, and the aziridine containing peptides were reacted with thiols while they were still protected and attached to the solid phase

SUMMARY OF THE INVENTION

The present invention provides an improved or modified method of NCL denominated "Aziridine Mediated Native Chemical Ligation". The method avoids many of the limitations of classical NCL. Like NCL, the present method is carried out under mild conditions and does not require the use of protecting groups. However, the present method advantageously does not require the presence of a cysteinyl peptide for the reaction to occur and is thus not limited to peptides and proteins which contain or can tolerate the presence of a Cys residue. In addition, the method is not unduly sensitive to steric hindrance during the coupling reaction. Furthermore, nucleophilic ring-opening of the aziridine ring results in production of unprotected peptides that are specifically modified at the ligation site. These features of the method make it applicable for the ligation or coupling of a wide array of molecules, including peptides of any desired sequence, even those which contain non-natural amino acid residues and those which contain various types of chemical modifications. The technology thus complements and extends existing native NCL technology.

Accordingly, with reference to Scheme 1, the invention provides methods and compositions for chemical ligation of a first component that includes a thioacid of variable group $R_1$ (1) and a second component that includes a 3-substituted aziridinyl-2-carbonyl (2, where the 3-substitution is depicted as "$R_2$") to give an aziridinyl-2-$COR_3$-3-$R_2$ ligation product (3). This coupling reaction is advantageously promoted by Cu(II) ion. The ligation product 3 has an amide bond at the aziridine nitrogen via which the $R_1$—CO group from the thioacid is attached. Ligation product 3 can be further modified via a nucleophilic attack resulting in an opening of the aziridine ring to yield a linear ligation product 4. Nucleophilic ring-opening is regioselective and stereoselective and results in production of unprotected peptides that are specifically modified at the ligation site.

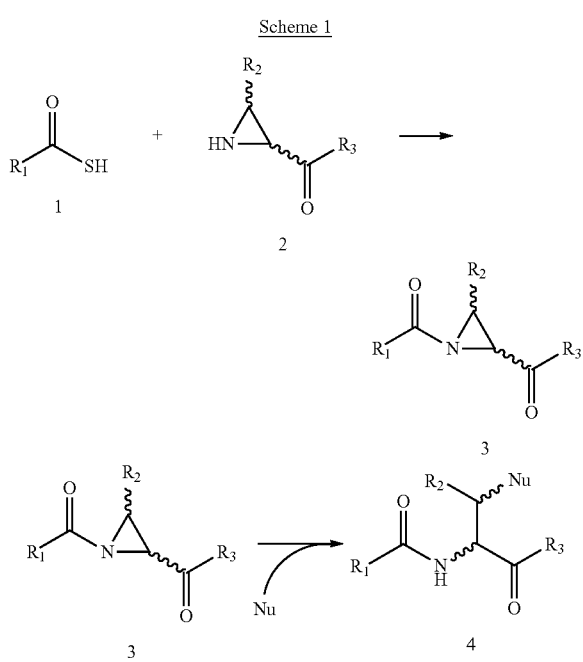

Scheme 1

The methods and compositions described herein are particularly useful for ligation of peptides and polypeptides. Variable groups $R_{1-3}$ can be independently varied, thereby providing the means to produce a wide variety of synthetically assembled complex molecules, including peptides, polypeptides, and other natural or non-natural amino acid containing polymers.

BRIEF DESCRIPTION OF THE DRAWINGS

FIGS. 2A and B. General aziridinyl peptide synthesis. A, illustration of undesired ring opening upon exposure to TFA; B, ring opening avoided by using DBU sensitive protecting groups.

DETAILED DESCRIPTION

Figure 1:
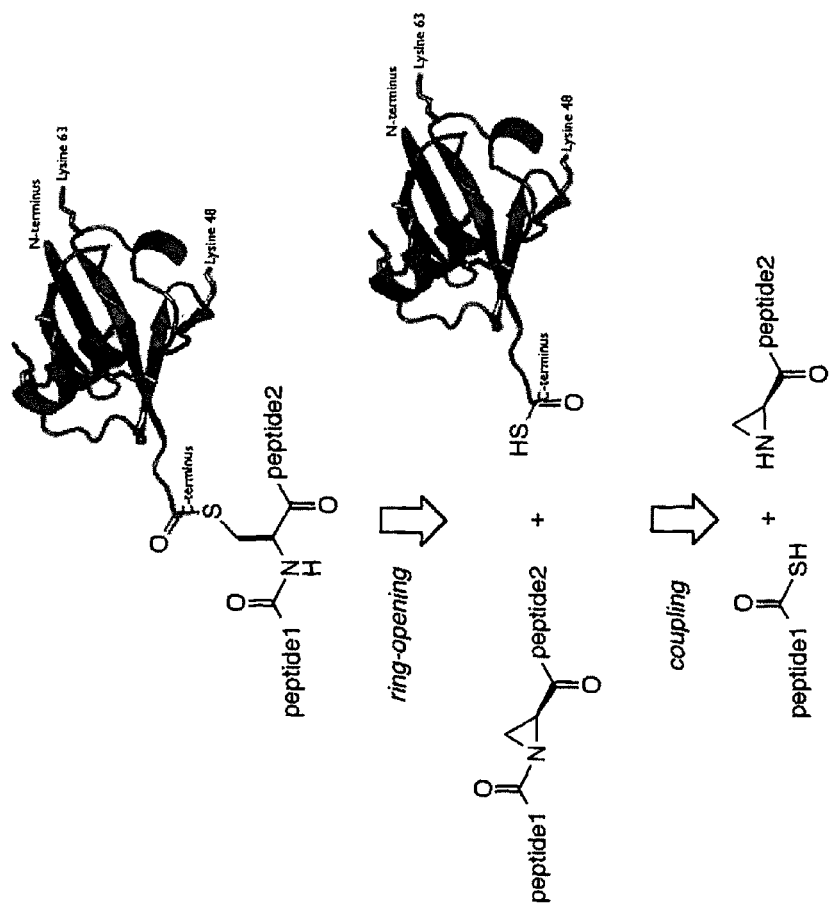
FIG. 1. Site-specific S-palmitoylation via aziridine-mediated ligation.

The invention provides methods and compositions for forming a covalent chemical bond between (i.e. for ligating, coupling, joining, etc.) two components of interest (e.g. a first and a second component) to form a polymeric compound. The first component is a thioacid i.e. an organic acid (usually a carboxylic acid) in which one or more of the oxygen atoms have been replaced by sulfur atoms; the thioacid contains a terminal SH that is reactive, i.e. which can undergo chemical coupling reactions. The thioacid also comprises a variable group, $R_1$ in Scheme 1. The second component is or includes an aziridinyl-2-carbonyl compound which comprises a variable group $R_3$ (see Scheme 1). The aziridinyl ring of component 2 may be further substituted at the 3 position with a second variable group, $R_2$ in Scheme 1.

Reaction between SH of component 1 and NH at position 1 of the aziridinyl ring of component 2 (e.g. mediated by Cu(II) ion) displaces SH from 1 and results in the joining of components 1 and 2 via formation of an amide bond between the organic acid and N of the aziridinyl ring. The resulting ligation product (3 in Scheme 1) is thus 1-$R_1$CO-2-CO$R_3$-3$R_2$-substituted aziridine.

Ligation product 3 can be further modified via opening of the aziridinyl ring which yields a linearized ligation product with formula $R_1$CO—NHCH(CH(Nu)$R_3$)CO—NH$R_2$ (4). In some embodiments, ring opening is accomplished by a nucleophilic attack on carbon at position 3 of the aziridine ring. The nucleophile or a portion thereof is "added" to the carbon, and the bond between positions 1 and 3 of the aziridine ring is broken (see Scheme 1).

In some embodiments, the method involves the coupling of unprotected peptide thioacids and N—H aziridine-2-carbonyl peptides. The unique reactivity of the resulting N-acylated aziridine-2-carbonyl peptides facilitates their subsequent regioselective and stereoselective nucleophilic ring-opening to give unprotected peptides that are specifically modified at the ligation site. Significantly, the overall process is compatible with a variety of unprotected amino acid functionality, most notably the N-terminus and Lys sidechain, and the method is applicable to both solid and solution phase syntheses, even those involving epimerizable and sterically hindered amino acids.

The following descriptions and definitions are used throughout.

According to the invention, both the joining of components 1 and 2 and ring opening are carried out under mild reaction conditions, precluding the need for protecting groups on variable groups $R_1$-$R_3$. By "mild reaction conditions" we mean ambient temperature. While the use of protecting groups (e.g. 9-fluorenylmethyloxycarbonyl (Fmoc), di-tert-butyl dicarbonate (tBoc), benzyloxy-carbonyl (Z) groups, allyloxycarbonyl (alloc), various lithographic light-cleavable protecting groups, etc.) is not required, in some embodiments it may be desirable to do so for one or more of $R_1$-$R_3$, and such embodiments are also encompassed by the invention.

By "nucleophile" we mean a chemical species that donates an electron-pair to an electrophile to form a chemical bond in a reaction. Because nucleophiles donate electrons, they are by definition Lewis bases. All molecules or ions with a free pair of electrons can act as nucleophiles. Nucleophilic reactions include those in which the nucleophile is an alcohol (alcoholysis), or contains and amino group (aminolysis), etc. Exemplary nucleophiles that may be used in the practice of the invention include but are not limited to: $H_2O$, alcohols, thioacids, thiols, phosphates, halides, isonitriles, and azides, etc.

The term "polymer" means a long molecule consisting of structural units connected by covalent chemical bonds. The units are typically smaller molecules of low to moderate molecular weight (e.g. from about 50 to about 500 Mr), and are linked to each other during a polymerization. The number of structural subunits in a polymer may range from at least 2 to about, for example, 5, 10, 15, 20, 25, 30, 35, 40, 45, 50, 55, 60, 65, 70, 75, 80, 84, 90, 95, or 100 or more (e.g. even up to 500, or up to 1000 or more), per polymer. In some embodiments, the number of structural units will be in the range of from about 2 to about 10, e.g. 2, 3, 4, 5, 6, 7, 8, 9, or 10; or up to about 20, e.g. 11, 12, 13, 14, 15, 16, 17, 18, 19 or 20. The structural units themselves may be "polymers", and may be or may comprise synthetic and/or naturally occurring components. Examples of polymers include, but are not limited to: proteins, nucleic acids, and carbohydrates. One or both of components 1 and 2 may be polymers or structural units of polymers, and the linearized reaction product may be a polymer, and/or may be used as a structural unit of a larger polymer.

As used herein, the term "peptide" refers to two or more amino acids covalently attached through a peptide bond. Peptide is intended to mean both naturally occurring and recombinant forms, as well as other non-naturally occurring forms of the peptide or protein.

"Amino acid" as used herein has the usual meaning as understood in the art, e.g. a molecule containing an amine group, a carboxylic acid group and a variable side-chain. Twenty-two "standard" amino acids are known alanine, arginine, aspartic acid, asparagine, cysteine, glycine, glutamic acid, glutamine, histidine, isoleucine, leucine, lysine, methionine, serine, phenyalanine, proline, threonine, tryptophan, tyrosine, valine, as well as selenocysteine, ornithine, etc. Any of these, or any variant thereof (e.g. 5-hydroxytryptophan, L-dihydroxyphenylalanine, phosphorylated amino acids, glycosylated amino acids, lipidated amino acids, dehydroalanine, dehydro-2-aminobutyric acid, lanthionine, methyllanthionine, D-amino acids, amino acids containing any unnatural modification (e.g. azido, alkyne, fluorescent functionality, etc.)) and others, may be employed in the practice of the invention.

The term "alkyl" refers to linear (unbranched) or branched chain unsubstituted hydrocarbon groups of about 1 to 20 carbon atoms, for example. The expression "lower alkyl" refers to unsubstituted alkyl groups of about 1 to 4 carbon atoms.

The term "substituted alkyl" refers to an alkyl group substituted by, for example, about one, two three or four substituents, examples of which include but are not limited to: halo, hydroxy, alkoxy, oxo, alkanoyl, aryloxy, alkanoyloxy, amino, alkylamino, substituted alkylamino, cycloalkylamino, substituted cycloalkylamino, arylamino, substituted arylamino, aralkylamino, substituted aralkyamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. These substituents may be further substituted, e.g. with alkyl, alkoxy, aryl, aralkyl, etc.

The term "halogen" or "halo" refers to, e.g. fluorine, chlorine, bromine and iodine.

The term "aryl" refers to compounds which contain an aromatic group, e.g. a monocyclic or polycyclic aromatic compound. Monocyclic aryls generally have about 4 to about 7 carbon atoms, bicyclic aryls may have e.g. from about 7 to about 11 carbon atoms, and tricyclic aryls may contain from about 10 to about 15 or more carbon atoms. Exemplary aryls are or comprise groups that include but are not limited to: phenyl, naphthyl, biphenyl (diphenyl), thienyl, indolyl, etc. Aryls may be substituted or unsubstituted, and may or may not include one or more heteroatoms (e.g. S, N, etc.) in one or more ring structures (heteroaryls).

The term "arylalkyl" refers to an aryl or a substituted aryl group bonded directly to an alkyl group, such as benzyl.

The term "substituted aryl" refers to an aryl group substituted by, for example, about one to about four (e.g. 1, 2, 3, or 4) substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" or "heteroaromatic" means that the compound is both heterocyclic (containing more than one type of ring, i.e. comprises at least two different rings) and aromatic (at least one of the rings is aromatic as described herein). Such compounds may be substituted or unsubstituted, and may contain heteroatoms within one or more rings, so long as a least one ring of the structure retains its aromatic character. Exemplary heteroaryls and/or components thereof include but are not limited to: pyridine, tetrazole, indazole, etc.

The term "alkenyl" refers to straight or branched chain hydrocarbon groups of about 2 to about 20 carbon atoms, preferably about 2 to about 15 carbon atoms, and most preferably 2 to 8 carbon atoms, having, for example, about one to about four double bonds.

The term "substituted alkenyl" refers to an alkenyl group substituted by, for example, one or more substituents, examples of which include but are not limited to: halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of about 2 to about 20 carbon atoms, preferably about 2 to about 15 carbon atoms, and most preferably about 2 to about 8 carbon atoms, having, for example, about one to about four triple bonds.

The term "substituted alkynyl" refers to an alkynyl group substituted by at least one substituent, examples of which include but are not limited to: halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring system, preferably containing from about 1 to 3 rings with from about 3 to 7 carbons per ring which may be further fused with, for example, one or more unsaturated carbocyclic rings (e.g. a C3-C7 unsaturated rings). Exemplary groups include cyclopropyl, cyclobutyl, cyclopentyl, cyclohexyl, cycloheptyl, and adamantyl. Exemplary substituents include one or more alkyl groups as described above, and/or one or more groups described above as alkyl substituents.

The terms "heterocycle", "heterocyclic" and "heterocyclyl" refer to an optionally substituted, fully saturated or unsaturated, aromatic or nonaromatic cyclic group which, for example, is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

The term "heteroatoms" shall include at least oxygen, sulfur and nitrogen.

The compounds of the invention may form salts which are also within the scope of this invention. Pharmaceutically acceptable (i.e. non-toxic, physiologically acceptable) salts are preferred, although other salts are also useful, e.g., in isolating or purifying the compounds of this invention.

An embodiment of the invention is directed to methods and compositions for chemical ligation of a first component that includes a thioacid (1) and a second component that includes a 3-substituted or 3-unsubstituted aziridinyl-2-carbonyl (2) to give a ligation product (3) having an amide bond at the ligation site. (Scheme 1) In some embodiments, the initial ligation is promoted by Cu(II) ions. However, this need not always be the case, as other catalysts may be discovered and/or employed.

The ligation product 3 (optionally) can be further converted via ring opening (e.g. by nucleophillic attack) to yield ligation product 4. (Scheme 1) Groups $R_{1-3}$, can be independently varied, thereby providing means to synthetically assemble various types of polymers and/or oligomers, including peptides, polypeptides, and various other natural or non-naturally occurring amino acid containing polymers. In one embodiment, $R_1$ and $R_3$ comprise amino acids or peptides the identity or primary sequences of which may be varied independently. In certain embodiments, $R_1$, $R_2$ and/or $R_3$ may comprise a polymer. In certain embodiments $R_1$, $R_2$ and/or $R_3$ may comprise a hydrogen (e.g. R=H), alkyl, substituted alkyl, halogen, aryl, aralkyl, substituted aryl, heteroaryl, alkenyl, substituted alkenyl, alkynyl, substituted alkynyl, cycloalkyl, heterocycle or heteroatom. In certain embodiments, $R_2$ comprises a chemical group suitable to form an amino acid side chain upon ring opening. In certain embodiments the $R_2$ may comprise a biologically active agent, examples include but are not limited to: a sugar, glycan, carbohydrate, nucleotide, nucleic acid, cofactor, peptide, prodrug, polymer, and/or lipid. In yet further embodiments $R_1$, $R_2$ and or $R_3$ may comprise a group operable for the detection or identification of the ligation product (i.e. they may be or comprise a detectable label), examples of which include but are not limited to: a fluorescent agent, a colored agent, a radiolabel, a capture agent (e.g. biotin), and/or a detectable polymer.

In certain embodiments, it may be desirable to open (break) the aziridine ring of compound 3, i.e. to linearize the molecule (although this is not always the case, since in some embodiments the desired end product may be "intermediate" 3 of Scheme 1). If desired, ring opening may be accomplished by a variety of mechanisms, including but not limited to, for example: isomerization (to yield a dehydroamino acid residue), and ring opening by exposing compound 3 to a suitable nucleophile. The nucleophile (Nu) may comprise a chemical group suitable to form an amino acid side chain upon ring opening. In certain embodiments the nucleophile (Nu) may comprise a biologically active agent, examples of which include but are not limited to: a sugar, glycan, carbohydrate, nucleotide, nucleic acid, cofactor, peptide, prodrug, radioactive agent, polymer, thioacid, thiol, phosphoric acid, azide, and/or isocyanide. In yet further embodiments, the nucleophile (Nu) may comprise a group operable, functioning or suitable for the detection or identification of the ligation product, examples of which include but are not limited to: a fluorescent agent, a colored agent, radiolabel, and/or a capture agent (e.g. biotin). In other embodiments, the nucleophile may comprise a chemical group which it is advantageous to include or retain in the final product. For example, Nu may comprise a thiopalmitic acid to give a specifically S-palmitoylated product or the Nu may comprise a ubiquitin thioacid to give a specifically S-ubiquitinated product.

In some embodiments, the ligation reaction is carried out using a single type of thioacid and a single type of aziridine compound. However, this need not always be the case. In some embodiments, multiple types of thioacids may be reacted with one aziridine compound in a reaction, or with multiple types of aziridine compounds, or multiple types of aziridine compounds may be reacted with one type of thioacid or with multiple types of thioacids, so that a mixture of reaction products is produced.

Scheme 2 provides an overview of the utility of the present invention with respect to the many variations that can be introduced into the composition of compounds synthesized by the method. Depending on the reaction conditions and specific nature of the nucleophile, a variety of distinct ligation products can be formed. Here $R_4$, $R_5$, $R_6$ and $R_7$ are independently selected from hydrogen (e.g. R=H), alkyl, substituted alkyl, halogen, aryl, aralkyl, substituted aryl, heteroaryl, alkenyl, substituted alkenyl, alkynyl, substituted alkynyl, cycloalkyl, heterocycle or heteroatom. X in 11 is a heteroatom present on $R_3$ prior to the opening of the azridine ring.

Scheme 2

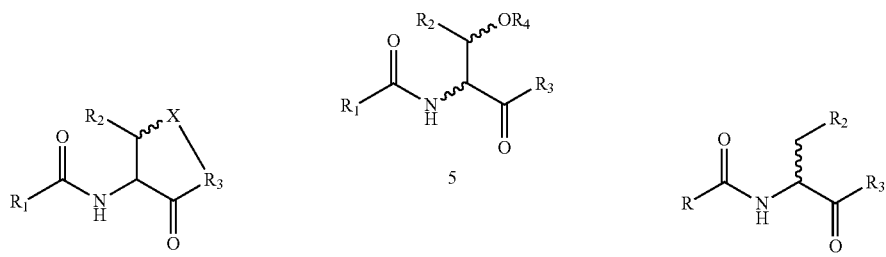

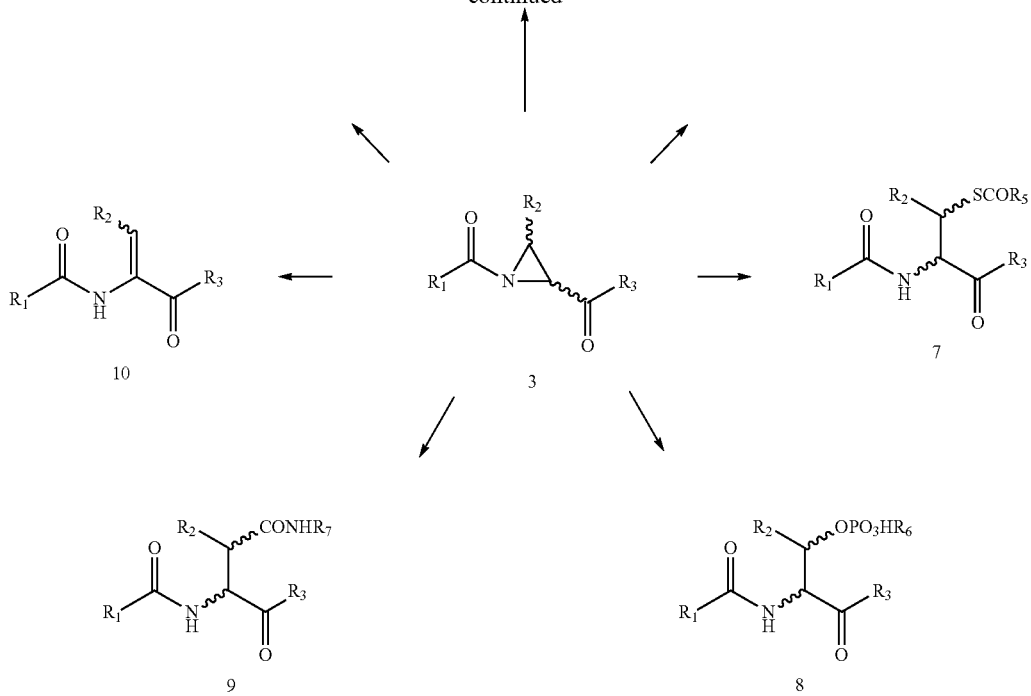

EXAMPLES

Example 1

Aziridine-Mediated Ligation and Site-Specific Modification of Unprotected Peptides Native chemical ligation (NCL)[1] enables the convergent synthesis of peptides and proteins under mild reaction conditions without the need for protecting groups. The NCL process is characterized by the chemoselective coupling of unprotected peptide thioesters (peptide1-Xaa-SR) and unprotected cysteinyl peptides (H-Cys-peptide2) to give ligation products peptide1-Xaa-Cys-peptide2[2]. Since an N-terminal Cys residue is required,[2] the general application of NCL to peptide/protein synthesis is limited to ligation at peptide linkages Xaa-Cys, where Xaa is preferably an unhindered amino acid. It follows that the incorporation of post-translationally modified or unnatural amino acids at the ligation site is not feasible with NCL.

We now disclose a ligation protocol that combines the convergent synthesis of unprotected aziridine-2-carbonyl containing peptides with their controlled site-specific chemical modification. The key reaction (Scheme 3) involves chemoselective Cu(II)-promoted coupling of a peptide thioacid[3] 1 with an aziridine-2-carbonyl (Azy) peptide 2 to give the initial ligation product 3 under native conditions. The unique properties of the chemical species involved—a moderately acidic thioacid combined with a moderately basic aziridine—enable the aziridine-mediated peptide ligation to be performed without peptide protecting groups. The Azy-containing peptide 3 may be converted to a site-specifically modified peptide 4 through regioselective opening of the aziridine ring by a nucleophile. Modifications may be introduced via the aziridine substituent ("R") and/or the nucleophilic species ("Nu").

Scheme 3. Aziridine-Mediated Peptide Ligation Concept.

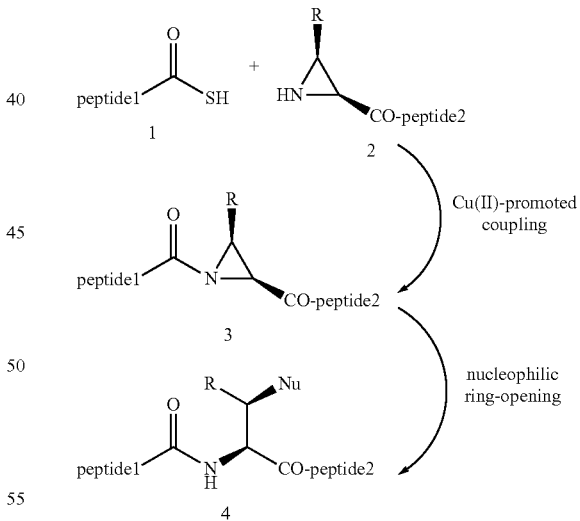

The potential utility of using an aziridine embedded in the backbone of a peptide as an electrophilic handle for the site-specific introduction of modifications has been recognized for some time.[4,5,6] However, the difficulty associated with the synthesis and manipulation of unprotected Azy-containing peptides has limited the full exploration and exploitation of their properties. In this communication, the aziridine-mediated peptide ligation concept is illustrated with a methyl-substituted aziridine-2-carbonyl moiety using water as the nucleophile, with the net result being ligation at a threonine site.

Scheme 4. Initial Coupling Reaction Optimization

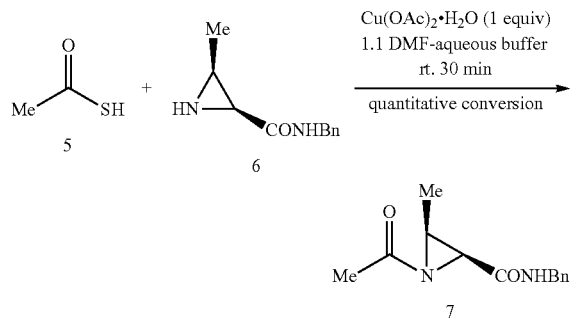

Our study began with thioacetic acid (5) serving as a model for 1 and the known[6] aziridine H-Azy(Me)-NHBn (6, Azy (Me)=(2S,3S) 3-methylaziridine-2-carbonyl) as a model for 2. In the presence of Cu(OAc)$_2$.H$_2$O, thioacid 5 reacted rapidly with aziridine 6 in mixtures of DMF and phosphate-citrate buffer (pH range 4.2-7.2) to give 7 (Scheme 4). Stoichiometric Cu(II) was found to be essential for clean and efficient coupling. In its absence, a complex mixture of products was observed, emanating from non-regioselective

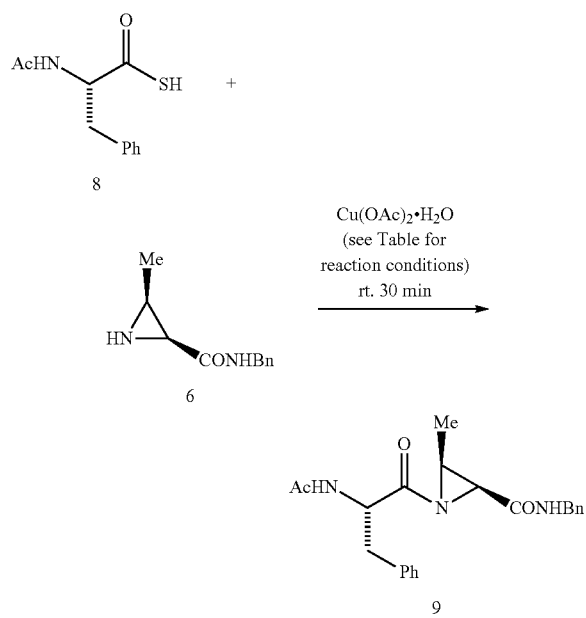

ring opening of 6 by 5 and, presumably, S— to N-acyl transfer.[8,9] The use of AgOAc instead of Cu(OAc)$_2$.H$_2$O resulted in a much slower reaction.[10] The subpar performance with K$_3$Fe(CN)$_6$ suggested that the Cu(II)-mediated reaction does not simply involve an oxidative mechanism.[11] These experiments established the critical role that Cu(II) plays in the aziridine-mediated coupling process as well as the reaction's compatibility with aqueous conditions.

The next stage of reaction optimization focused on assessing the level of epimerization during the coupling of Ac-Phe-SH (8)[12] to 6 and defining conditions to minimize it (Table 1). This coupling reaction proceeded rapidly and cleanly in DMF-aqueous buffers to produce Ac-Phe-Azy(Me)-NHBn (9). However, 13-14% of the epimeric product Ac-phe-Azy (Me)-NHBn (epi-9) was also observed in these reactions (Entries 1-3). The level of epimerization could be reduced to 6% when the reaction was performed in DMF alone but the crude yield was lowered (Entry 4). The inclusion of 1-hydroxybenzotriazole (HOBt) in the reaction mixture was found to reduce the level of epimerization to 10% in DMF-aqueous buffer and 5% in DMF. HOBt also increased the yield of the ligation reaction. The optimal coupling conditions were thus defined as 1 equiv of Cu(OAc)$_2$.H$_2$O and 2 equiv HOBt in DMF.

TABLE 1

Optimization of Coupling Reaction Conditions

| Entry | Solvent | HOBt (equiv) | 9 + epi-9 (% yield) | epi – 9[b] (mol %) |
|---|---|---|---|---|
| 1 | 1:1 DMF-buffer (pH 7.2) | 0 | 68 | 13 |
| 2 | 1:1 DMF-buffer (pH 6.2) | 0 | 82 | 13 |
| 3 | 1:1 DMF-buffer (pH 5.2) | 0 | 87 | 14 |
| 4 | DMF | 0 | 53 | 6 |
| 5 | 1:1 DMF-buffer (pH 7.2) | 2 | 88 | 10 |
| 6 | DMF | 2 | 89 | 5 |

We were now ready to combine the coupling reaction with an aziridine ring-opening reaction and address the chemoselec-tivity issue (Table 2). It was decided to use H$_2$O as the nucleophile converting the unprotected Azy(Me)-containing peptide to a Thr-containing peptide (10+11→[12]→13). First, the coupling of 8 and 6 was repeated but, rather than isolate 9, the reaction mixture was treated directly with 10% TFA/H$_2$O. The hydrolysis product Ac-Phe-Thr-NHBn (14) was isolated in good overall yield after standard workup and purification (Entry 1).[13] The formation of this 14 is consistent with regioselective and stereoselective nucleophilic opening of the aziridine ring at C3 by H$_2$O. The reaction of diastereomerically pure dipeptide thioacid Fmoc-Phe-Ala-SH (15) and aziridine 6 produced Fmoc-Phe-Ala-Thr-NHBn (16) (Entry 2).[14] Comparison with an authentic sample of Fmoc-Phe-Ala-Thr-NHBn (epi-16) established the level of epimerization at 5%.

TABLE 2

Aziridine-Mediated Peptide Ligation at Xaa-Thr Sites

| Entry | Thioacid (1.1 equiv.) | Aziridine | Solvent | Product | Yield |
|---|---|---|---|---|---|
| 1 | Ac-Phe-SH (8) | H-Azy(Me)-NHBn (6) | DMF | Ac-Phe-Thr-NHBn (14) | 69 |
| 2 | Fmoc-Phe-Ala-SH (15) | H-Azy(Me)-NHBn (6) | DMF | Fmoc-Phe-Ala-Thr-NHBn (16) | 72 |

TABLE 2-continued

Aziridine-Mediated Peptide Ligation at Xaa-Thr Sites

| Entry | Thioacid (1.1 equiv.) | Aziridine | Solvent | Product | Yield |
|---|---|---|---|---|---|
| 3 | H-Lys-Tyr-Thr-SH (17) | H-Azy(Me)-NHBn (6) | DMF | H-Lys-Tyr-Thr-Thr-NHBn (18) (SEQ ID NO: 1) | 80 |
| 4 | H-Glu-Tyr-Thr-SH (19) | H-Azy(Me)-NHBn (6) | DMF | H-Glu-Tyr-Thr-Thr-NHBn (20) (SEQ ID NO: 2) | 69 |
| 5 | H-Glu-Tyr-Thr-SH (19) | H-Azy(Me)-NHBn (6) | 0.2M Pi-citrate buffer, pH 6.9 | H-Glu-Tyr-Thr-Thr-NHBn (20) (SEQ ID NO: 2) | 71 |
| 6 | H-Glu-Tyr-Thr-SH (19) | H-Azy(Me)-NHBn (6) | 8M urea in 0.1M Pi buffer, pH 7.5 | H-Glu-Tyr-Thr-Thr-NHBn (20) (SEQ ID NO: 2) | 88 |
| 7 | H-Cys-Tyr-Ala-SH (21) | H-Azy(Me)-NHBn (6) | DMF | H-Cys-Tyr-Ala-Thr-NHBn (22) (SEQ ID NO: 3) | 43 |
|   |   |   |   | (H-Cys-Tyr-Ala-Thr-NHBn)$_2$ (23) (SEQ ID NO: 3) | 40 |
| 8 | H-Lys-Tyr-Thr-SH (17) | H-Azy(Me)-Phe-Gly-NH$_2$ (24) | DMF | H-Lys-Tyr-Thr-Thr-Phe-Gly-NH$_2$ (25) (SEQ ID NO: 4) | 78 |
| 9 | H-Glu-Tyr-Thr-SH (19) | H-Azy(Me)-Phe-Gly-NH$_2$ (24) | 8M urea in 0.1M Pi buffer, pH 7.5 | H-Glu-Tyr-Thr-Thr-Phe-Gly-NH$_2$ (26) (SEQ ID NO: 5) | 77 |

The coupling/ring-opening sequence was then performed with H-Lys-Tyr-Thr-SH (17)[15] and 6 to produce H-Lys-Tyr-Thr-Thr-NHBn (18) (SEQ ID NO: 1) in good yield (Entry 3). An analogous experiment using the peptide thioacid H-Glu-Tyr-Thr-SH (19) produced H-Glu-Tyr-Thr-Thr-NHBn (20) (Entry 4) (SEQ ID NO: 2). Compatibility of the coupling reaction with aqueous buffer and the denaturant urea was established (Entries 5 & 6). The coupling/ring-opening protocol was also applied to a Cys-containing peptide thioacid 21 to afford a mixture of peptide 22 and its disulfide 23 (Entry 7).[16] Finally, we extended the ligation to the union of thioacids 17 and 19 with the aziridine-containing tripeptide H-Azy(Me)-Phe-Gly-NH$_2$ (24)[17] to give hexapeptides 25 and 26, respectively (Entries 8 & 9). To summarize, the aziridine-mediated ligation is compatible with free NH$_2$, CO$_2$H, OH (aliphatic and aromatic), and SH functional groups (by virtue of in situ protection as a disulfide). The facility of ligation employing an equimolar quantity of relatively hindered thioacid (reaction complete within 1-2 h) is also noteworthy.

The method disclosed herein enables one to synthesize unprotected aziridine-containing peptides and regioselectively hydrolyze the embedded aziridine moiety to give products corresponding to ligation at Xaa-Thr linkages.[18] It is anticipated that the aziridine ring-opening reaction will not be limited to the use of water as a nucleophile.[4,6]

REFERENCES FOR BACKGROUND AND EXAMPLE 1

(1) Reviews: a) Tam, J. P.; Xu, J.; Eom, K. D. *Biopolymers* (Peptide Sci.) 2001, 60, 194-205; b) Nilsson, B. L.; Soellner, M. B.; Raines, R. T. *Annu. Rev. Biophys. Biomol. Struct.* 2005, 34, 91-118; c) Hackenberger, C. P. R.; Schwarzer, D. *Angew. Chem. Int. Ed.* 2008, 47, 10030-10074; d) Kent, S. B. H. *Chem. Soc. Rev.* 2009, 38, 338-351.

(2) Efforts to overcome this requirement include: a) Tam, J. P.; Yu, Q. *Biopolymers* 1998, 46, 319-327; b) Offer, J.; Boddy, C. N. C.; Dawson, P. E. *J. Am. Chem. Soc.* 2002, 124, 4642-4646; c) Wu, B.; Chen, J.; Warren, J. D.; Chen, G; Hua, Z.; Danishefsky, S. J. *Angew. Chem. Int. Ed.* 2006, 45, 4116-4125; d) Botti, P.; Tchertchian, S. WO/2006/133962; e) Crich, D.; Banerjee, A. *J. Am. Chem. Soc.* 2007, 129, 10064-10065; f) Payne, R. J.; Fichet, S.; Greenberg, W. A.; Wong, C.-H. *Angew. Chem. Mt Ed.* 2008, 47, 4411-4415; g) Okamoto, R.; Kajihara, Y. *Angew. Chem. Int. Ed.* 2008, 47, 5402-5406; h) Haase, C.; Rohde, H.; Seitz, O. *Angew. Chem. Int. Ed.* 2008, 47, 6807-6810; i) Chen, J.; Wan, Q.; Yuan, Y.; Zhu, J.; Danishefsky, S. J. *Angew. Chem. Int. Ed.* 2008, 47, 8521-8524; j) Bennett, C. S.; Dean, S. M.; Payne, R. J.; Ficht, S.; Brik, A.; Wong, C.-H. *J. Am. Chem. Soc.* 2008, 130, 11945-11952; k) Yang, R.; Pasunooti, K. K.; Li, F.; Liu, X.-W.; Liu, C.-F. *J. Am. Chem. Soc.* 2009, 131, 13592-13593; l) Harpaz, Z.; Siman, P.; Kumar, K. S. A.; Brik, A. *ChemBioChem* 2010, 11, 1232-1235; m) Chen, J.; Wang, P; Zhu, J.; Wan, Q.; Danishefsky, S. J. *Tetrahedron* 2010, 66, 2277-2283; n) Shang, S.; Tan, Z.; Dong, S.; Danishefsky, S. J. *J. Am. Chem. Soc.* 2011, 133, 10784-10786.

(3) Danishefsky has reported the HOBt-mediated oxidative coupling of peptide thioacids and free N-terminal peptides. This method is not compatible with unprotected sidechain amines. Wang. P.; Danishefsky, S. J. *J. Am. Chem. Soc.* 2010, 132, 17045-17051.

(4) Okawa, K.; Nakajima, K. *Biopolymers* 1981, 20, 1811-1821.

(5) Korn, A.; Rudolph-Böhner, S.; Moroder, L. *Tetrahedron* 1994, 50, 1717-1730.

(6) Galonic, D. P.; Ide, N. D.; van der Donk, W. A.; Gin, D. Y. *J. Am. Chem. Soc.* 2005, 127, 7359-7369.

(7) Shao, H.; Jiang, X.; Gantzel, P.; Goodman, M. *Chemistry & Biology* 1994, 1, 231-234.

(8) The C2-selective opening of NH aziridine-2-carbonyl-terminated peptides (formed in situ from β-bromoalanylpeptides) by peptide thioacids to give a β-peptide linkage (after S- to N-acyl transfer) was originally observed by Tam et al.: Tam, J. P.; Lu, Y. A.; Liu, C. F.; Shao, J. *Proc. Natl. Acad. Sci. USA* 1995, 92, 12485-12489.

(9) Recently, a convergent synthesis of protected peptidomimetics via the coupling of protected peptide thioacids and protected 2-aziridinylmethylpeptides was reported: Assem, N.; Natarajan, A.; Yudin, A. K. *J. Am. Chem. Soc.* 2010, 132, 10986-10987.

(10) Ag(I) ion is known to promote the oxidative coupling of thioacids and primary amines: a) Schwabacher, A. W.; Bychowski, R. A. *Tetrahedron Lett.* 1992, 33, 21-24; b) Blake, J. *Int. J. Peptide Protein Res.* 1981, 17, 273-274; c) Blake, J.; Li, C. H. *Proc. Natl. Acad. Sci. USA* 1981, 78, 4055-4058.

(11) $K_3Fe(CN)_6$, is known to promote the N-acylation of primary amines via dithioacids: Liu, R.; Orgel, L. E. *Nature* 1997, 389, 52-54.

(12) Thioacid 8 was prepared from commercially available Ac-Phe-OH (1. NHS, DCC, DCM, rt, 4 h; 2. NaHS, MeOH, 63% yield) using a known method: Goldstein, A. S.; Gelb, M. H. *Tetrahedron Lett.* 2000, 41, 2797-2800.

(13) The structure of 14 was confirmed through comparison with an authentic sample prepared using standard peptide coupling protocols.

(14) The Fmoc protecting group was retained in this example to facilitate quantitative determination of the epimer ratio.

(15) Peptide thioacids 17, 19, and 21 were prepared by deprotection (TFA, DCM, $Et_3SiH$, 0° C.) of their STmb thioester precursors in 73, 53, and 45% yields.

(16) MS analysis of this coupling reaction indicated predominant formation of a disulfide corresponding to intermediate 12, which implies that the free thiol may be undergoing an in situ protection. Reductive disulfide cleavage likely occurs during the workup with aqueous NaSH, which can act as a reducing agent. Minor products emanating from perthioester intermediates were also detected. See: Liu, C. F.; Rao, C.; Tam, J. P. *Tetrahedron Lett.,* 1996, 37, 933-936.

(17) The aziridine-containing tripeptide 24 was prepared from the union of Tr-Azy(Me)-OH and H-Phe-Gly-$NH_2$ (HATU, DIEA, DMF, rt, 48% yield) followed by deprotection (TFA, (1:1) $CHCl_3$-MeOH, 0° C., 61% yield).

(18) A protocol for ligation at Thr via chemical ligation of a γ-thiol-substituted N-terminal Thr peptide followed by post-ligation desulfurization was recently reported. See reference (2m).

I. Experimental Procedures

Ia. General Considerations. Reagent grade solvents were used for extraction and flash chromatography. All reagents and solvents were purchased from commercial sources and were used without further purification unless otherwise noted. The progress of reactions was monitored by analytical thin layer chromatography (TLC, silica gel F-254 plates) or analytical HPLC (see below). TLC plates were visualized first with UV illumination (254 nm) followed by charring using either ninhydrin stain (0.3% ninhydrin (w/v) in 97:3 EtOH/AcOH) or a modification of Hanessian's stain (10 g ammonium molybdate (($NH_4$)$_6$$Mo_7$$O_{24}$.$4H_2O$) and 5 g cerium sulfate ($Ce(SO_4)_2$) in 1 L 10% aq. $H_2SO_4$). Aqueous NaSH was prepared fresh daily by dissolving ~50 mg NaSH hydrate in 1-2 mL of water. Flash column chromatography was performed on flash grade (230-400 mesh) silica gel. The solvent compositions reported for all chromatographic separations are on a volume/volume (v/v) basis. Solvent removal under reduced pressure was performed by rotary evaporation (pressure ~16 mm Hg, bath temperature 25-30° C.) followed by pumping under high vacuum until the container reached a constant mass. High performance liquid chromatography (HPLC) was carried out using an X-Bridge C18 (3×250 mm column) for analytical separations and X-Bridge C18 (19× 150 mm) column for semipreparative purifications. HPLC Eluent B was a solution of 0.1% TFA in MeCN and Eluent A was a 0.1% aqueous solution. HPLC analysis was monitored using dual channel UV detection at 254 and 215 nm. All peptide products purified by preparative HPLC were isolated by removing the MeCN and free TFA by rotary evaporation and the remaining water by lyophilization. Melting points are uncorrected. Optical rotations were recorded at room temperature at the sodium D line (589 nm). $^1$H NMR spectra were recorded at ambient temperature, at 300 or 600 MHz, and are reported in parts per million (ppm) on the δ scale relative to tetramethylsilane (δ0.00). $^{13}$C NMR spectra were recorded at 75.5 or 150.8 MHz and are reported in parts per million (ppm) on the δ scale relative to $CDCl_3$ (δ77.00). High resolution mass spectrometry (HRMS) was performed using MALDI in either α-cyano-4-hydroxycinnamic acid or 3,5-dimethoxy-4-hydroxycinnamic acid matrices. Low resolution mass spectrometry (LRMS) was performed using ESI.

Ib. Aziridine and Aziridinyl Peptide Synthesis i. Synthesis of Ac-Azy(Me)-NHBn (7)

H-Azy(Me)-NHBn (6) Tr-Azy(Me)-NHBn[1a] (S1, 860 mg, 1.99 mmol) was added to an ice-cold stirring solution of 1:1 $CHCl_3$/MeOH (7 mL) and stirred until homogeneous. TFA (3.0 mL, 39 mmol) was added dropwise to the stirring solution over 10 minutes. After 2 h, the reaction was diluted with EtOAc (250 mL) and extracted with water (3×100 mL). The combined aqueous extracts were neutralized by adding portions of sat. $NaHCO_3$ until solution reached pH 8 (litmus). The aqueous solution was extracted with DCM (3×100 mL) and the DCM layers were combined, dried ($MgSO_4$), filtered, and solvent was removed under reduced pressure to afford 6 as clear oil that solidified when stored at 4° C. (360 mg, 95% yield). This solid was used without further purification. $R_f$ 0.24 (6% MeOH/DCM); HPLC: gradient 5% to 70% MeCN/ $H_2O$ over 20 min, 0.5 mL/min $t_R$: 12.8 min; $^1$H NMR (300 MHz, $CDCl_3$) δ 7.33-7.23 (5H), 6.92 (bs, 1H), 4.42 (d, J=6.0 Hz, 2H), 2.70 (d, J=6.7 Hz, 1H), 2.38 (m, 1H), 1.29 (bs, 1H), 1.13 (d, J=5.7 Hz, 3H); $^{13}$C NMR (75 MHz, $CDCl_3$) δ 169.4, 138.4, 128.8, 128.0, 127.6, 43.3, 36.6, 32.5, 13.8; HRMS m/z calcd for $C_{11}H_{15}N_2O$ [$MH^+$] 191.1263. found 191.1196.

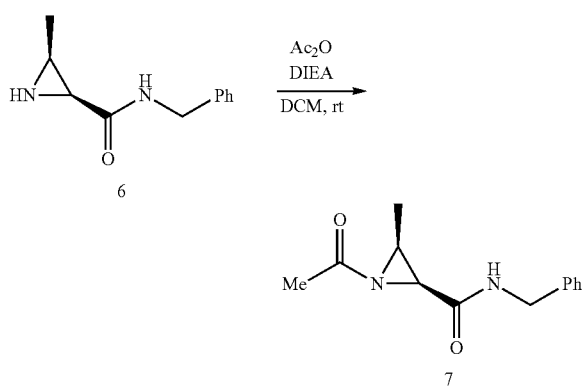

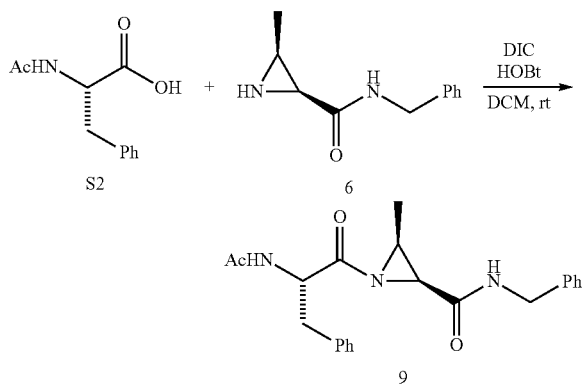

Ac-Azy(Me)-NHBn (7). A genuine sample of 7 was prepared as follows: To a stirring solution of 6 (46 mg, 0.24 mmol) in DCM (1 mL) was added DIEA (0.200 mL, 1.15 mmol) and Ac$_2$O (0.050 mL, 0.53 mmol). After stirring at rt for 1 h, the reaction mixture was directly loaded onto a silica gel column for chromatographic purification (6% MeOH/DCM) to afford the desired product as a clear, colorless oil (52 mg, 93% yield). R$_f$ 0.28 (6% MeOH/DCM); HPLC: gradient 5% to 70% MeCN/H$_2$O over 20 min, 0.5 mL/min t$_R$: 14.3 min; $^1$H NMR (300 MHz, CDCl$_3$) δ 7.40-7.14 (5H), 6.65 (s, 1H), 4.51 (dd, J=14.7, 6.3 Hz, 1H), 4.36 (dd, J=14.6, 5.6 Hz, 1H), 3.16 (d, J=6.8 Hz, 1H), 2.80-2.70 (m, 1H), 2.10 (s, 3H), 1.25 (d, J=5.7 Hz, 3H); $^{13}$C NMR (75 MHz, CDCl$_3$) δ 182.2, 166.5, 137.9, 129.0, 128.1, 127.9, 43.5, 41.9, 38.6, 23.6, 13.6; HRMS m/z calcd for C$_{13}$H$_{17}$N$_2$O$_2$ [MH$^+$] 233.1290. found 233.1102.

ii. Synthesis of Ac-Phe-Azy(Me)-NHBn (9)

Ac-Phe-Azy(Me)-NHBn (9). A genuine sample of 9 was prepared as follows: Ac-Phe-OH (S2, 50 mg, 0.24 mmol)+HOBt (40 mg, 0.30 mmol)+6 (44 mg, 0.23 mmol) were stirred into a suspension in DCM (0.5 mL) at rt. To make the reaction homogenous, a small amount of DMF (~0.3 mL) was added. To the stirring solution was added DIC (50 µL, 0.32 mmol). After 1 h, the resulting white suspension was filtered and the filter cake was washed with EtOAc (10 mL). The filtrate was washed with water (6×10 mL), and the organic layer was dried (MgSO$_4$), filtered, and concentrated by rotary evaporation. Flash chromatographic purification (6% MeOH/DCM) of the crude residue afforded 9 as a white solid (30 mg, 34% yield). R$_f$ 0.18 (6% MeOH/DCM); HPLC: gradient 15% to 50% B in A over 25 min, 0.5 mL/min t$_R$: 22.0 min; $^1$H NMR (300 MHz, CDCl$_3$) δ 7.41-7.01 (10H), 6.34 (bm, J=5.8, 1H), 6.23 (bm, 1H), 4.59 (ddd, J=9.6, 7.1, 5.9, 1H), 4.46 (dd, J=14.7, 6.6, 1H), 4.27 (dd, J=14.7, 5.5, 1H), 3.09 (dd, J=13.0, 5.8, 1H), 2.98 (dd, J=13.0, 9.6, 1H), 2.89-2.79 (m, 2H), 1.97 (s, 3H), 1.13 (d, J=6.5, 3H); $^{13}$C NMR (75 MHz, CDCl$_3$) δ 183.1, 170, 4, 166.3, 138.1, 136.3, 129.5, 128.9, 128.8, 128.1, 127.8, 127.6, 56.6, 43.4, 41.1, 39.1, 38.7, 23.0, 13.4. HRMS m/z calcd for C$_{22}$H$_{26}$N$_3$O$_3$ [MH$^+$] 380.1974. found 380.1980.

iii. Synthesis of H-Azy(Me)-Phe-Gly-NH$_2$ (20)

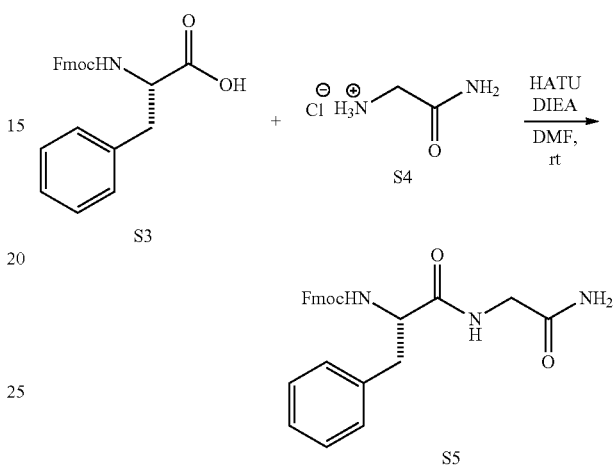

Fmoc-Phe-Gly-NH$_2$ (S5). To a stirring solution of Fmoc-Phe-OH(S3, 1.800 g, 4.647 mmol)+HATU (1.856 g, 4.881 mmol) in DMF (19.0 mL) was added DIEA (2.40 mL, 13.8 mmol). This solution slowly changed from colorless to yellow over 5 minutes, when the HCl salt of H-Gly-NH$_2$ (S4, 0.444 g, 4.02 mmol) was added and the reaction stirred under dry argon for 3 h. The reaction was subsequently concentrated under high vacuum to ~5 mL, then diluted with EtOAc (500 mL). The resulting yellow solution was sequentially washed with 10% aq. citric acid, sat. NaHCO$_3$, and brine (100 mL each). The organic layer was dried (MgSO$_4$), filtered, and left to stand at rt whereupon S5 began to spontaneously crystallize. After allowing the mixture to stand overnight, a first crop was collected and air-dried (0.949 g, 53% yield, mp 185-187° C.). After successive concentrations and recrystallizations of the mother liquor, subsequent crops had elevated, broader melting ranges (528 mg combined, 28%, mp 195-201° C.). These samples were identical to the first crop by $^1$H NMR analysis. R$_f$ 0.18 (7% MeOH/DCM); $^1$H NMR (300 MHz, DMSO-d$_6$) δ 8.22 (t, J=5.6, 1H), 7.86 (d, J=7.5, 2H), 7.72-7.57 (overlapped d+t, 3H), 7.45-7.06 (13H), 4.24 (ddd, J=10.4, 8.6, 4.1, 1H), 4.19-4.04 (3H), 3.68 (dd, J=17.0, 5.9, 1H), 3.61 (dd, J=17.0, 5.9, 1H), 3.03 (dd, J=13.6, 4.1, 1H), 2.77 (dd, J=13.6, 10.6, 1H); $^{13}$C NMR (75 MHz, DMSO-d$_6$) δ 172.4, 171.4, 156.6, 144.4, 141.3, 138.9, 129.9, 128.7, 128.3, 127.7, 126.9, 126.0, 120.8, 66.4, 56.9, 47.2; HRMS m/z calcd for C$_{26}$H$_{26}$N$_3$O$_4$ [MH$^+$] 444.1923. found 444.1722; m/z calcd for C$_{26}$H$_{25}$N$_3$NaO$_4$ [MNa$^+$] 466.1743. found 466.1622.

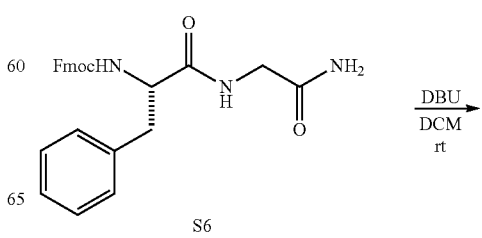

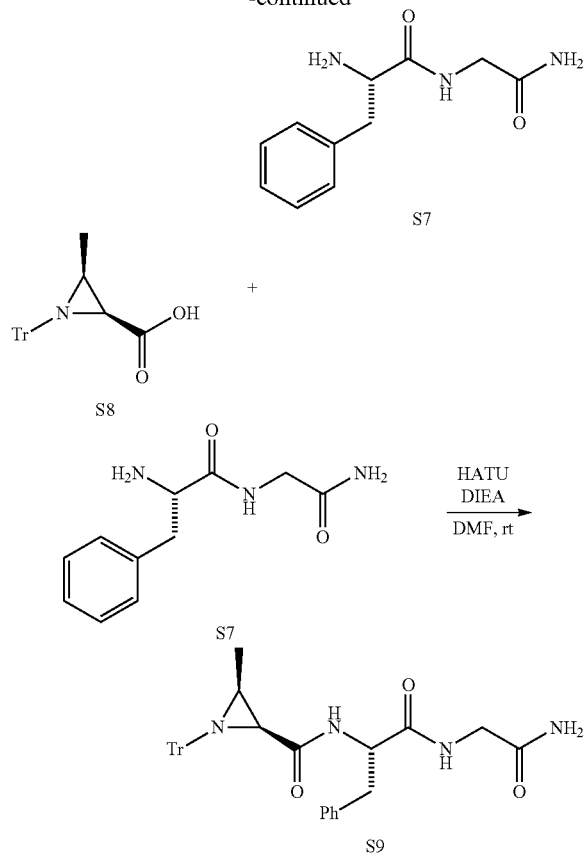

Tr-Azy(Me)-Phe-Gly-NH$_2$ (S9). S6 (140 mg, 0.316) was subjected to a standard Fmoc deprotection procedure (see section Ic-ii below) and then and then coupled to Tr-Azy(Me)-OH[1b] (S8) using the standard HATU coupling procedure (see section Ic-ii). The reaction was diluted with EtOAc (20 mL) and washed sequentially with 10% citric acid (15 mL), water (6×15 mL), and brine (20 mL). The organic layer was dried (MgSO$_4$), filtered, and solvent was removed under reduced pressure. The crude product was purified by flash chromatography (7% MeOH/DCM) to afford S9 as a white foam (83 mg, 48% over two steps). R$_f$ 0.57 (10% MeOH/DCM); FIRMS m/z calcd for C$_{34}$H$_{35}$N$_4$O$_3$ [MH$^+$] 547.2709. found 547.2928.

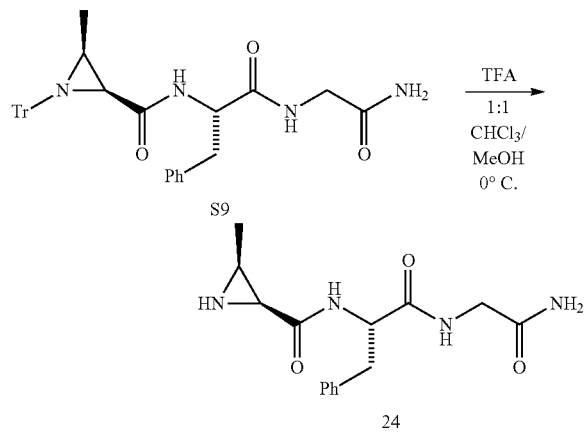

H-Azy(Me)-Phe-Gly-NH$_2$ (24).
Method A: To an ice-cold stirring solution of 1:1 CHCl$_3$/MeOH (1 mL)+S9 (29 mg, 0.053 mmol) was added TFA (3.0 mL, 39 mmol, dropwise over 5 minutes). After 30 minutes, solvent was removed by rotary evaporation (ca. 20 Torr, 22° C.) to afford an oily yellow solid. Et$_2$O (1 mL) was added to the flask to precipitate a slightly sticky white solid. The supernatant was decanted carefully by Pasteur pipette, and the Et$_2$O wash/decant was repeated twice. The white solid had residual solvent removed in vacuo to afford 24 as it is TFA salt (18 mg, 81%). This salt, showing >90% purity by HPLC, was used directly in the subsequent ligation. Analytical samples of the TFA salt of 24 prepared in H$_2$O or MeOH had to be analyzed immediately after being prepared or significant decomposition would be observed.

Method B: The reaction was performed as in method A. The oily yellow solid obtained from rotary evaporation is partitioned between EtOAc (1 mL) and sat. NaHCO$_3$ (3×1 mL). The combined aq. layers were washed with Et$_2$O (2 mL). Residual volatile organics were removed by a brief rotary evaporation. The crude product solution was purified by preparative HPLC to afford 24 as a fluffy white solid (10.1 mg, 61% yield). This lyophilized product was found to be stable to storage in the freezer for 5 days, however when analyzed again after 2 months significant decomposition was observed.

HPLC: gradient 5% to 95% B in A over 25 min, 0.8 mL/min t$_R$: 6.9 min; $^1$H NMR (600 MHz, DMSO-d$_6$) δ 8.71 (d, J=7.9 Hz), 8.30 (t, J=5.7 Hz, 1H), 8.25 (t, J=5.8 Hz), 7.35-7.03 (8H), 4.54 (m, 1H), 3.68 (m, 1H), 3.58 (m, 1H), 3.05 (dd, J=14.0, 4.5 Hz, 1H), 2.84 (dd, J=13.9, 9.9 Hz, 1H), 2.37 (dd, J=8.6, 6.8 Hz, 1H), 2.19-2.03 (m, 1H), 1.08 (d, J=5.7 Hz, 1H), 0.53 (d, J=5.5 Hz, 2H); HRMS m/z calcd for C$_{15}$H$_{21}$N$_4$O$_3$ [MH$^+$] 305.1614. found 305.1669; m/z calcd for C$_{15}$H$_{20}$N$_4$NaO$_3$ [MNa$^+$] 327.1433. found 327.1539.

Ic. Thioacid Synthesis
i. Synthesis of Ac-Phe-SH (8)

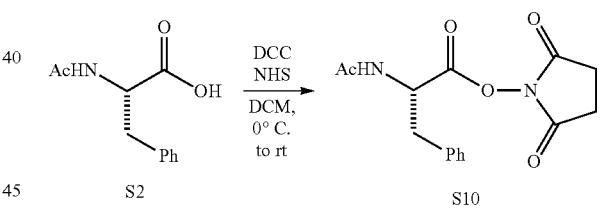

Ac-Phe-OSu (S10). An ice-cold stirring suspension of Ac-Phe-OH(S2, 0.504 g, 2.43 mmol) in DCM (10 mL) was sequentially charged with DCC (0.187 g, 2.95 mmol) and N-Hydroxysuccinimide (NHS, 307 mg, 2.67 mmol). The reaction was stirred for 3.5 h at 0° C., when $^1$H NMR analysis of the crude reaction mixture showed the reaction to be complete (diagnostic peak for remaining S2 (300 MHz, CDCl$_3$) δ 1.82 ppm). The resulting white sus-pension was filtered and the filter cake washed with DCM (10 mL). The filtrate was chilled in a −10° C. freezer for 2 h and filtered again with minimal DCM rinsing of the filtercake (1-2 mL). The DCM solution was concentrated by rotary evaporation and the product was precipitated from EtOAc to afford S10 as a white solid (734 mg, 99% yield). This product, contaminated with a neglible amount of dicyclohexylurea, was used without further purification. $^1$H NMR (300 MHz, CDCl$_3$) δ 7.42-7.10 (5H), 5.78 (d, J=7.7 Hz, 1H), 5.29 (m, 1H), 3.33 (dd, J=14.1, 6.1 Hz, 1H), 3.23 (dd, J=14.2, 5.6 Hz, 1H), 2.86 (s, 4H), 1.97 (s, 3H).; HRMS m/z calcd for C$_{15}$H$_{16}$N$_2$NaO$_5$ [MNa$^+$] 327.0957. found 327.3312.

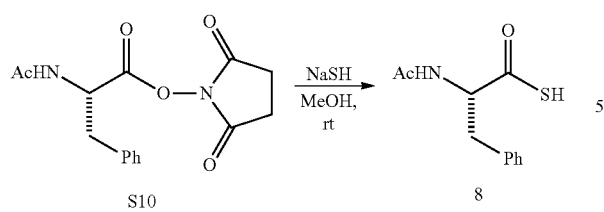

Ac-Phe-SH (8). Following the general procedure reported by Gelb,[2] to a stirring solution of S10 (113 mg, 0.371 mmol) in MeOH (3.0 mL) was added with NaSH hydrate (pellet form, 59 mg, 1.0 mmol) at rt. The NaSH dissolved within 5 minutes, resulting in a translucent yellow solution that gradually changed to a yellow opaque suspension during the course of the reaction. After stirring for 2.5 h, the reaction has solvent removed by rotary evaporation and the resulting residue was partitioned between water (5 mL) and EtOAc (2×5 mL). The aq. layer was acidified by dropwise addition of conc. HCl solution (~0.2 mL) to pH 1 (litmus). The acidic layer was extracted with DCM (3×10 mL), and the combined organic extracts were dried (MgSO$_4$), filtered, and solvent was removed under reduced pressure to afford 8 as a colorless oil (52 mg, 63% yield). The product was found to be very unstable to a variety of storage conditions, thus was used immediately in the subsequent ligation reactions. $^1$H NMR (300 MHz, CDCl$_3$) δ 7.46-7.07 (5H), 6.24 (bs, 1H), 4.92 (dt, J=7.5, 5.9, 1H), 3.17 (dd, J=14.2, 5.7, 1H), 3.04 (dd, J=14.3, 7.3, 1H), 1.96 (s, 3H); $^{13}$C NMR (75 MHz, CDCl$_3$) δ 199.1, 170.6, 135.6, 129.5, 129.0, 128.8, 127.6, 61.1, 37.6, 25.7, 23.2.

ii. General Fmoc-Based Solution Phase Peptide Synthesis Protocols.

General Fmoc deprotection procedure of amino acid derivatives: The Fmoc-protected compound was dissolved and stirred in a solution of DCM (0.1 M)+DBU (2 equiv.) at rt. The reaction, unless otherwise noted, was complete within 30 min. The reaction mixture was directly loaded onto a short silica gel column (50 mL dry silica/1 g Fmoc-protected starting material) with minimal DCM rinsing. The column was eluted under pressure (as in flash chromatography, but with the solvent flow rate increased ~300%) with DCM to remove dibenzofulvene and subsequently eluting with 5-10% MeOH in DCM to obtain the free amine. The product had solvent removed under reduced pressure and was used directly in the subsequent coupling step.

General HATU peptide coupling procedure: Reactions were performed using a modified version of Carpino's original procedure:[3] An ice cold stirring solution of the carboxylic acid (1.2 equiv.) in DMF (0.1 M) was sequentially charged with HATU (1.2 equiv.) and DIEA (1.2 equiv.). The resulting solution was stirred for 5 minutes. The free amine (1.0 equiv.) was added as a solution DMF. The ice bath removed after 0.5 h, and the reaction was monitored by TLC for the disappearance of the free amine. Once complete, the reaction was worked up and the product purified as indicated.

iii. Synthesis of Fmoc-Phe-Ala-SH (15).

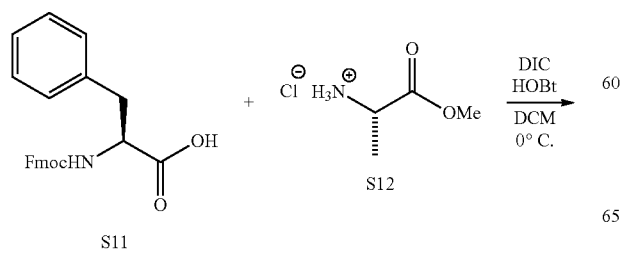

Fmoc-Phe-Ala-OMe (S13). Fmoc-Phe-OH(S11, 831 mg, 2.15 mmol)+HOBt (295 mg, 2.18 mmol) was stirred into an ice-cold suspension in DCM (20 mL). The reaction was charged with DIC (0.340 mL, 2.20 mmol) and stirred for 5 minutes. To the resulting homogenous colorless solution was added the HCl salt of H-Ala-OMe (S12, 251 mg, 1.80 mmol) and DIEA (0.320 mL, 1.84 mmol). After 70 minutes, the resulting suspension was filtered, the filtercake was washed with DCM (10 mL), and the combined filtrates were chilled to −10° C. for 1 h. The mixture was filtered again, then washed with sat. NaHCO$_3$ (2×10 mL) and brine (10 mL). The organic layer was dried (MgSO$_4$), filtered, and concentrated by rotary evaporation. The crude product was precipitated from Et$_2$O and residual solvent was removed under reduced pressure, affording S13 as a white solid (983 mg, 97% yield). The crude product was used without further purification despite a minor contamination of diisopropylurea. An analytical sample was obtained by flash chromatographic purification (35% EtOAc/hexanes). R$_f$ 0.59 (1:1 EtOAc/hexanes); $^1$H NMR (300 MHz, CDCl$_3$) δ 7.77 (d, J=7.5 Hz, 2H), 7.54 (m, 2H), 7.40 (t, J=7.2 Hz, 2H), 7.35-7.15 (7H), 6.29 (d, J=5.6 Hz, 1H), 5.35 (d, J=6.3 Hz, 1H), 4.55-4.41 (overlapped m, 3H), 4.33 (t, J=8.7 Hz, 1H), 4.19 (t, J=6.9 Hz, 1H), 3.71 (s, 3H), 3.14 (dd, J=13.5, 6.2 Hz, 1H), 3.03 (dd, J=13.1, 7.1 Hz, 1H), 1.34 (d, J=7.2 Hz, 1H); HRMS m/z calcd for C$_{28}$H$_{27}$N$_2$O$_5$ [MH$^+$] 473.2067. found 473.1988; m/z calcd for C$_{28}$H$_{26}$N$_2$NaO$_5$ [MH$^+$] 495.1896. found 495.1872.

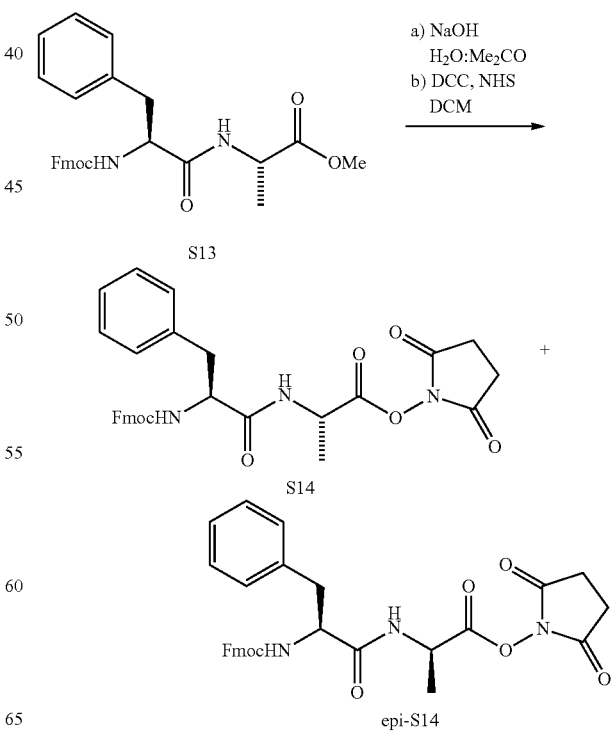

Fmoc-Phe-Ala-OSu (S14)+Fmoc-Phe-ala-OSu (epi-S14). To a stirring solution of S13 (483 mg, 1.02 mmol) in 4:1 Me₂CO/H₂O at rt was added 2M aq. NaOH (1.0 mL, 2.0 mmol). After 1 h, TLC analysis indicated the consumption of S13 along with the formation of dibenzolfulvene, indicating partial decomposition of the Fmoc group during this process. Acetone was removed by rotary evaporation, and the aq. layer was washed with Et₂O (5 mL). The aq. layer was carefully acidified to pH 1 with conc. HCl (~0.5 mL), then extracted with DCM (2×20 mL). The DCM extracts were combined, dried (MgSO₄), filtered, and had solvent removed under reduced pressure to afford the crude carboxylic acid (231 mg, 49% yield).[4] The residue was stirred into solution in DCM (10 mL). To the stirring solution was added DCC (170 mg, 0.824 mmol)+NHS (89 mg, 0.77 mmol). With intent to racemize the product at this stage, the reaction was left to stir overnight at rt. The resultant white suspension was filtered, and the filter-cake was washed with DCM (10 mL). The combined filtrates were chilled to −10° C. for 1 h. The mixture was filtered again, and solvent was removed by rotary evaporation. Stirring the resulting sticky foam with Et₂O/hexanes (1:1, ~4 mL) precipitated a white solid that was significantly easier to handle. Residual solvent was removed under reduced pressure to afford S14 and epi-S14 (285 mg, 49% yield over two steps). As the product is an inseparable mixture, only diagnostic peaks of the ¹H NMR are being reported. ¹H NMR (300 MHz, CDCl₃) δ 7.76 (d, J=7.5 Hz, 1H), 7.53 (dd, J=7.1, 4.3 Hz, 1H), 7.40 (t, J=7.1 Hz, 1H), 2.86 (s), 2.83 (s), 2.82 (s).

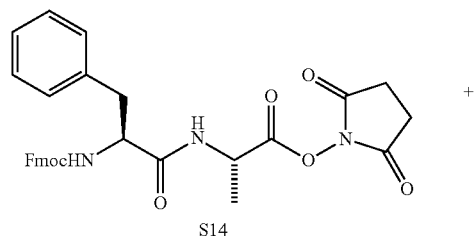

S14

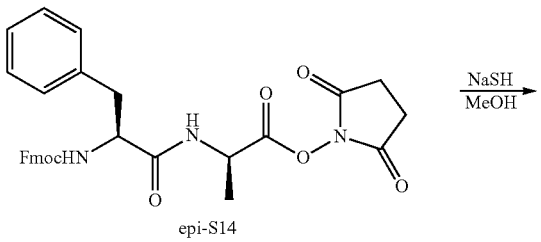

epi-S14

Fmoc-Phe-Ala-SH (15)+Fmoc-Phe-Ala-SH (epi-15). The mixture of S14+epi-S14 (102 mg, 0.184 mmol) was dissolved in MeOH (2 mL). To the stirring solution was added NaSH hydrate (29 mg, 0.52 mmol). The reaction changed from a colorless solution to a semi-transparent yellow suspension over the course of 2.5 h. At this time, solvent was removed by rotary evaporation and the residue was partitioned between H₂O (10 mL) and Et₂O (10 mL). After removing trace volatiles by rotary evaporation, a white precipitate formed in the aq. layer. This precipitate was brought back into solution by addition of a small amount of MeOH. The crude product solution was purified by preparative HPLC (in this case, lyophilization required the use of ⁱBuOH as a co-solvent) to afford 15 (18.4 mg, 21% yield) and epi-15 (3.0 mg, 3% yield). Significant quantities of side-products were observed but were not identified.[4]

15: HPLC: gradient 5% to 100% B in A for 20 min, 0.6 mL/min; $t_R$: 18.0 min; ¹H NMR (600 MHz, DMSO-d₆) δ 8.54 (bs, 1H), 7.87 (d, J=7.5 Hz, 2H), 7.70 (d, J=8.8 Hz, 1H), 7.67-7.60 (m, 2H), 7.42-7.25 (8H), 7.18 (t, J=7.4 Hz, 1H), 4.37-4.30 (m, 1H), 4.27 (ddd, J=11.9, 8.9, 3.4 Hz, 1H), 4.12 (s, 3H), 3.11 (dd, J=13.8, 3.2 Hz, 1H), 2.76 (dd, J=13.8, 11.4 Hz, 1H), 1.30 (d, J=7.1 Hz, 3H); HRMS m/z calcd for $C_{27}H_{26}N_2NaO_4S$ [MNa⁺] 497.1511. found 497.0669.

epi-15: HPLC: gradient 5% to 100% B in A for 20 min, 0.6 mL/min; $t_R$: 17.6 min; HRMS m/z $C_{27}H_{26}N_2NaO_4S$ [MNa⁺] 497.1511. found 497.1478.

iv. Synthesis of H-Lys-Tyr-Thr-SH (17).

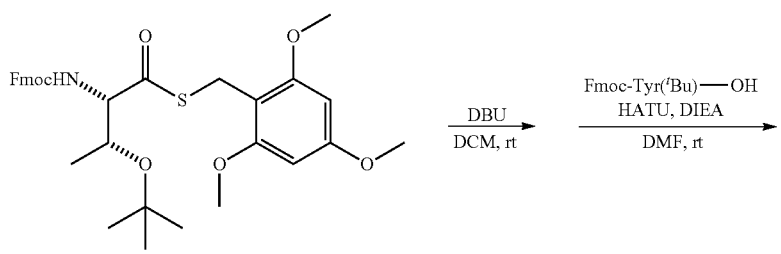

S15

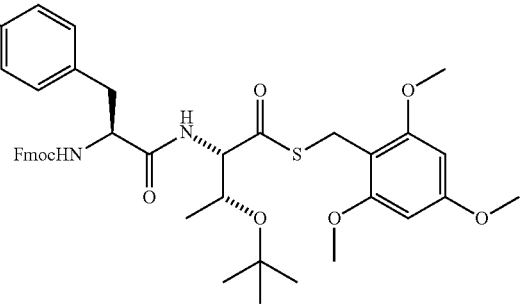

S16

Fmoc-Tyr(tBu)-Thr(tBu)-STmb (S16). S15[5] (469 mg, 0.790 mmol) was subjected to the standard Fmoc deprotection procedure and then coupled to Fmoc-Tyr(tBu)-OH using the standard HATU coupling procedure. The reaction was diluted with EtOAc (150 mL), and washed with 10% citric acid solution (50 mL), sat. NaHCO$_3$ (3×50 mL), and brine (50 mL). The organic layer was dried (MgSO$_4$), filtered, and concentrated by rotary evaporation. The crude product was purified by flash chromatography (dry loading the crude product onto silica is strongly recommended; eluted with 40% EtOAc/hexanes) to afford S16 as a white foam (437 mg, 68% yield over two steps).[6] R$_f$ 0.62 (1:1 EtOAc/hexanes); $^1$H NMR (300 MHz, CDCl$_3$) δ 7.81-6.80 (14H), 6.05 (s, 1H), 5.32 (d, J=8.9, 1H), 4.59-4.41 (m, 2H), 4.27 (m, 2H), 4.16 (m, 2H), 3.75 (bs, 9H), 3.17 (dd, J=13.7, 5.1, 1H), 3.05 (dd, J=14.1, 6.9, 1H), 1.29 (s, 9H), 1.10 (s, 9H); HRMS m/z calcd for C$_{46}$H$_{56}$N$_2$NaO$_9$S [MNa$^+$] 835.3604. found 835.2576.

Fmoc-Lys(Boc)-Tyr(tBu)-Thr(tBu)-STmb (S17). S16 (420 mg, 0.517 mmol) was subjected to the standard Fmoc deprotection procedure and then coupled to Fmoc-Lys(Boc)-OH using the standard HATU coupling procedure. The reaction was diluted with EtOAc (150 mL), and washed with 10% citric acid solution (50 mL), sat. NaHCO$_3$ (3×50 mL), and brine (50 mL). The organic layer was dried (MgSO$_4$), filtered, and concentrated by rotary evaporation. The crude product was purified using flash chromatography (dry loading the crude product onto silica is strongly recommended, eluted with 1:1 EtOAc/hexanes) to afford S17 as a white foam (413 mg, 77% yield over two steps). R$_f$ 0.29 (1:1 EtOAc/hexanes); $^1$H NMR (300 MHz, CDCl$_3$) δ 7.81-6.41 (m, 15H), 6.08 (s, 2H), 4.86-4.64 (m, 2H), 4.47 (d, J=8.9, 3H), 4.43-4.14 (m, 6H), 3.79 (s, 3H), 3.77 (s, 6H), 3.20 (dd, J=14.4, 5.9, 1H), 3.02 (m, 3H), 1.83-1.67 (m, 1H), 1.59 (m, 1H), 1.42 (s, 9H), 1.27 (s, 9H), 1.10 (s, 9H); HRMS m/z calcd for C$_{57}$H$_{76}$N$_4$NaO$_{12}$S [MNa$^+$] 1063.5078. found 1063.4727.

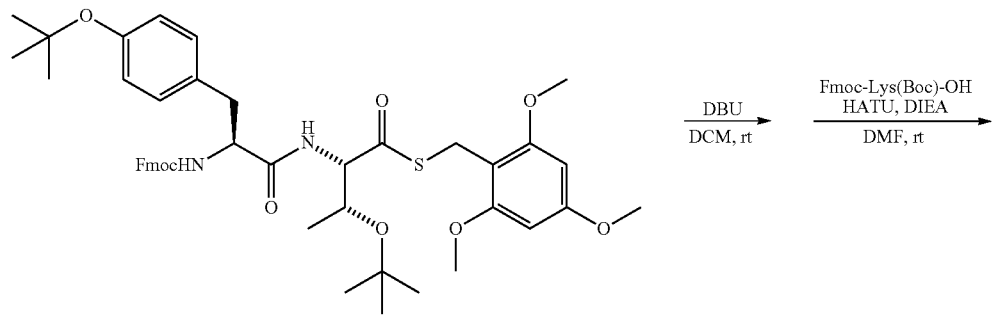

S16

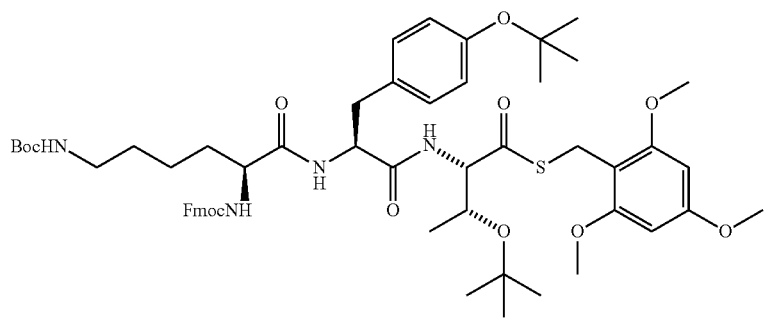

S17

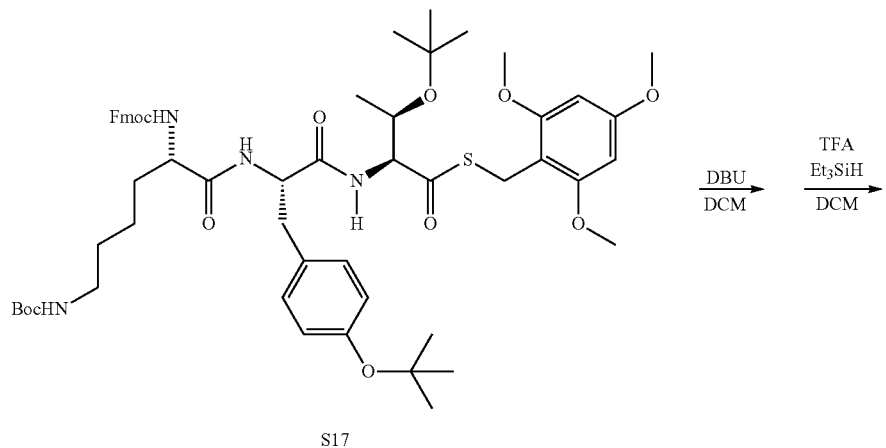

S17

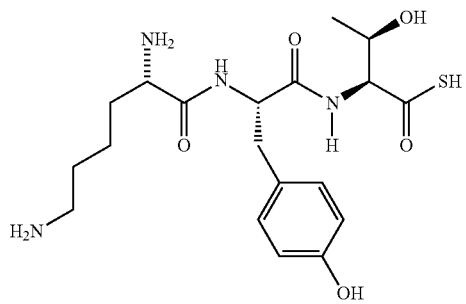

17

H-Lys-Tyr-Thr-SH (17). S17 (48 mg, 0.046 mmol) was subjected to the standard Fmoc de-protection procedure. The amine residue was chilled to 0° C., and the reaction vessel was purged under high vacuum and flushed with argon. An ice-cold solution of TFA (0.600 mL), DCM (0.200 mL), and Et$_3$SiH (0.250 mL) was charged to the reaction vessel and stirred at 0° C. After 0.5 h, the ice bath was removed and the reaction allowed to warm to ambient temperature, where it was monitored by HPLC and LRMS until analysis showed the reaction to be complete after an additional 3.5 h. Diagnostic HPLC: isocratic 10% B in A, 2 min, then gradient 10% to 60% B in A over 23 min, 0.6 mL/min; $t_R$: 5.5 min for 17, $t_R$: 17.4 min for H-Lys-Tyr(OH)-Thr(OH)-STmb (identified by LRMS: m/z calcd for $C_{29}H_{43}N_4O_8S$ [MH$^+$] 607.1. found 607.1). The reaction was partitioned between water (10 mL) and Et$_2$O (2×6 mL). The aqueous layer had trace volatiles removed by brief rotary evaporation, and then the crude product solution was purified by preparative HPLC to afford the bis-TFA salt of 17 as a fluffy white solid (22 mg, 73% yield over two steps). HRMS m/z calcd for $C_{19}H_{30}N_4O_5S$ [MH$^+$] 427.2015. found 427.2891.

v. Synthesis of H-Glu-Tyr-Thr-SH (19)

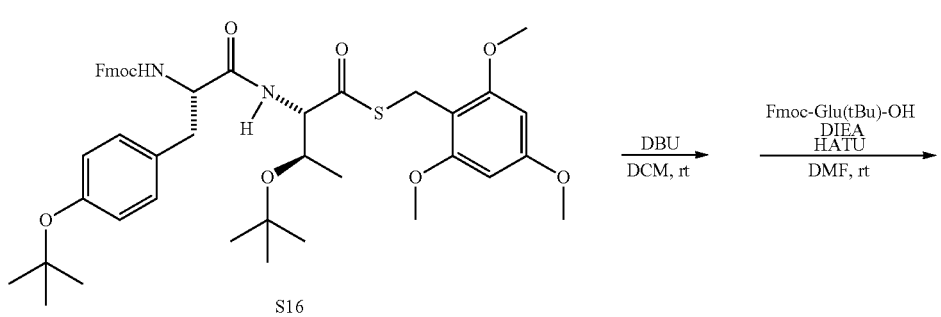

S16

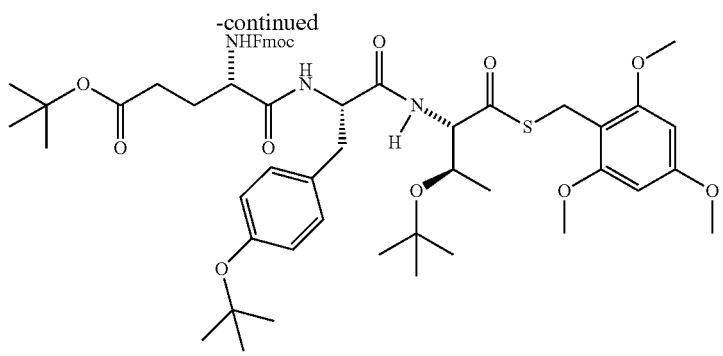

S18

Fmoc-Glu(ᵗBu)-Tyr(ᵗBu)-Thr(ᵗBu)-STmb (S18). S16 (285 mg, 0.315 mmol) was subjected to the standard Fmoc deprotection procedure and then coupled to Fmoc-Glu(ᵗBu)-OH using the standard HATU coupling procedure. The reaction was diluted with EtOAc (100 mL), and washed with 10% citric acid solution (30 mL), sat. NaHCO$_3$ (2×30 mL), water (20 mL) and brine (30 mL). The organic layer was dried (MgSO$_4$), filtered, and concentrated by rotary evaporation. The crude product was purified using flash chromatography (dry loading the crude product onto silica is strongly recommended, eluted with 45% EtOAc/hexanes) to afford S18 as a white foam that reverted to an clear oil upon standing at rt. Triturating the oil at −78° C. with Et$_2$O/hexanes (~1:10 mixture) and removal of solvent under reduced pressure afforded S18 as a white powder (340 mg, 97% yield over two steps). $R_f$ 0.50 (1:1 EtOAc/hexanes); $^1$H NMR (300 MHz, CDCl$_3$) δ 7.76 (d, J=7.3, 2H), 7.59 (d, J=7.6, 2H), 7.39 (t, J=7.4, 2H), 7.31 (t, J=7.5, 2H), 7.13 (d, J=8.4, 2H), 6.96 (d, J=7.2, 1H), 6.84 (d, J=8.4, 2H), 6.71 (d, J=9.2, 1H), 6.08 (s, 2H), 5.64 (d, J=7.5, 1H), 4.71 (~q, J=7.0, 1H), 4.47 (d, J=8.9, 1H), 4.35 (d, J=6.9, 2H), 4.27 (d, J=7.2, 1H), 4.21 (d, J=6.3, 1H), 4.16 (d, J=2.9, 1H), 3.79 (s, 3H), 3.77 (s, 6H), 3.21 (dd, J=14.2, 5.6, 1H), 3.01 (dd, J=14.1, 7.4, 1H), 2.47-2.20 (2H), 2.11-1.95 (1H), 1.87 (2H), 1.44 (s, 9H), 1.27 (s, 9H), 1.10 (s, 9H).; HRMS m/z calcd for C$_{55}$H$_{71}$N$_3$NaO$_{12}$S [MNa$^+$] 1020.4656. found 1020.4389.

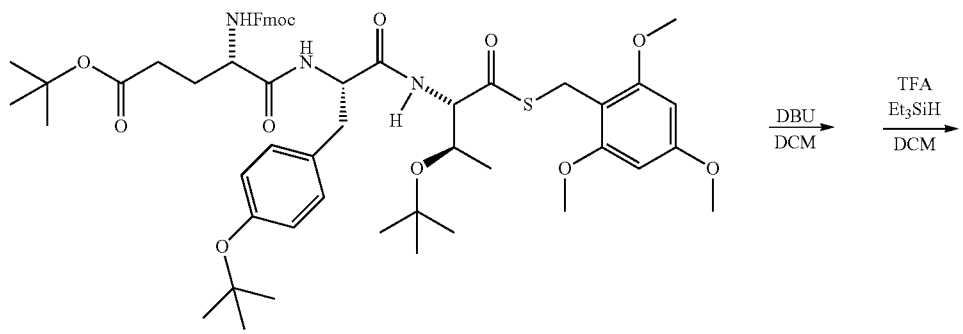

S18 →(DBU/DCM)→ (TFA, Et$_3$SiH/DCM) →

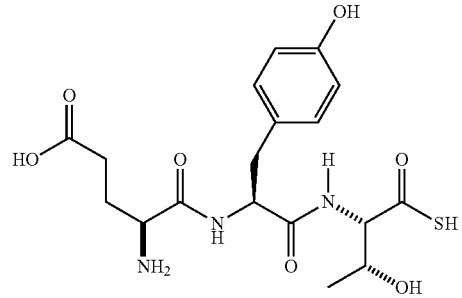

19

H-Glu-Tyr-Thr-SH (19). S18 (63.5 mg, 0.0636 mmol) was subjected to the standard Fmoc de-protection procedure. The amine residue was chilled to 0° C., and the reaction vessel was purged under high vacuum and flushed with argon. An ice-cold solution of TFA (0.600 mL), DCM (0.200 mL), and Et$_3$SiH (0.250 mL) was charged to the reaction vessel and stirred at 0° C. After 0.5 h, the ice bath was removed and the reaction was allowed to warm to ambient temperature, where it was monitored by HPLC and LRMS until analysis showed the reaction to be complete after an additional 3.5 h. The reaction was partitioned between water (13 mL) and Et$_2$O (2×6 mL). The aqueous layer had trace volatiles removed by brief rotary evaporation, and then the crude product solution was purified by preparative HPLC to afford the TFA salt of 19 as a fluffy white solid (18.2 mg, 53% yield over two steps). HPLC: isocratic 10% B in A, 2 min, then gradient 10% to 60% B in A over 23 min, 0.6 mL/min; $t_R$: 7.6 min; HRMS m/z calcd for $C_{18}H_{26}N_3O_7S$ [MH$^+$] 428.1491. found 428.1364.

vi. Synthesis of H-Cys-Tyr-Ala-SH (21).

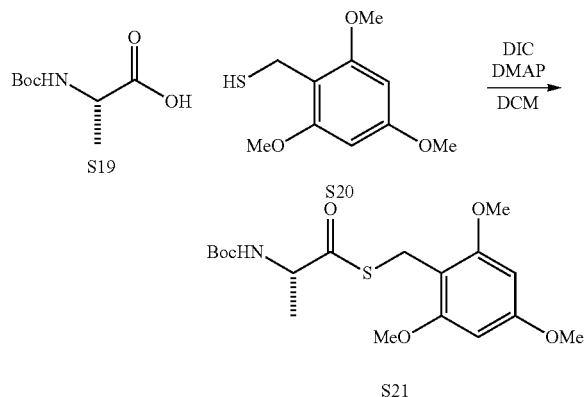

Boc-Ala-STmb (S21). To an ice-cold stirring suspension of S19 (377 mg, 1.99 mmol)+S20[7] (427 mg, 1.99 mmol)+HOBt (323 mg, 2.39 mmol) in dry DCM (5 mL, fresh dist. under argon from CaH$_2$) under argon was added DIC (302 mg, 2.39 mmol). The white suspension rapidly changed to a homogenous solution that was allowed to stir overnight and warm to ambient temperature. After 24 h (TLC analysis still showed unreacted S20), the reaction was diluted with DCM (5 mL) and washed with NaHCO$_3$ (2×10 mL), water (2×10 mL), and brine. The organic layer was dried (Na$_2$SO$_4$), filtered, and was concentrated by rotary evaporation. The crude residue was purified by flash chromatography (1:4 EtOAc/hexanes) afforded the desired product S21 (167 mg, 22%) as well as unreacted S20.[4] $R_f$ 0.67 (30% EtOAc/hexanes); NMR (300 MHz, CDCl$_3$) δ 6.11 (s, 2H), 5.03 (d, J=7.9, 1H), 4.43 (p, J=7.0, 1H), 4.21 (s, 2H), 3.82 (s, 3H), 3.81 (s, 6H), 1.45 (s, 9H), 1.40 (d, J=7.0, 3H); $^{13}$C NMR (75 MHz, CDCl$_3$) δ 161.1, 159.4, 104.7, 90.7, 56.4, 56.0, 55.6, 28.6, 22.4, 19.6; HRMS m/z calcd for $C_{18}H_{27}NNaO_6S$ [MNa$^+$] 408.1457. found 408.1393.

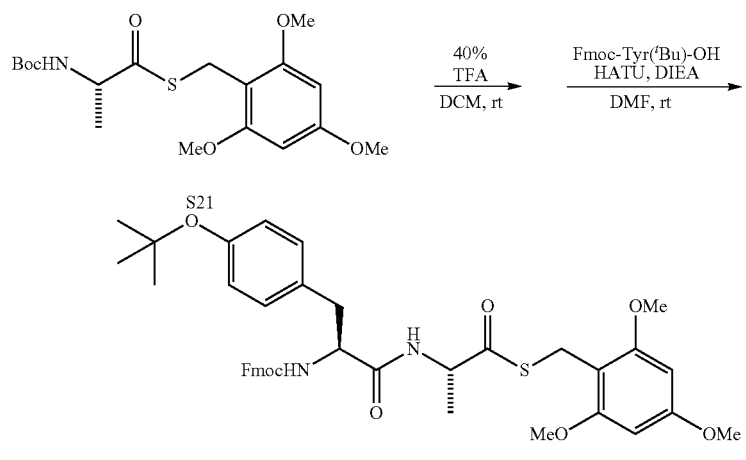

Fmoc-Tyr($^t$Bu)-Ala-STmb (S22). To a stirring solution of S21 (365 mg, 0.950 mmol) in DCM (6 mL) was added TFA (4 mL). After stirring for 10 minutes, the reaction was washed with a solution of water (10 mL)+20% aq. NaHCO$_3$ (20 mL), then washed once more with 20% aq. NaHCO$_3$ (20 mL). The organic layer was dried (MgSO$_4$), filtered, and had solvent removed under reduced pressure. The free amine residue was used directly in a standard HATU coupling with Fmoc-Tyr($^t$Bu)-OH. The coupling reaction was worked up by diluting with DCM (15 mL) and washing sequentially with sat. NaHCO$_3$ (2×15 mL), water (3×20 mL), and brine (20 mL). The organic layer was dried (MgSO$_4$), filtered, and concentrated by rotary evaporation. Flash chromatographic purification of the crude residue afforded S22 as a white solid (509 mg, 74% yield). $R_f$ 0.82 (5% MeOH/DCM); $^1$H NMR (300 MHz, CDCl$_3$) δ 7.62-6.83 (12H), 6.52 (d, J=6.7, 1H), 6.08 (s, 2H), 5.43 (d, J=8.2, 1H), 4.68 (p, J=7.1 Hz, 1H), 4.41 (m 2H), 4.30 (dd, J=10.6, 6.9, 1H), 4.24-4.11 (m, 3H), 3.77 (s, 9H), 3.05 (d, J=5.6, 2H), 1.34 (d, J=7.0, 3H), 1.30 (s, 9H). $^{13}$C NMR (75 MHz, CDCl$_3$) δ 200.7, 170.6, 161.1, 159.4, 154.6, 143.9, 141.5, 130.1, 127.9, 127.3, 125.3, 124.6, 120.2, 90.6, 78.6, 67.3, 56.0, 55.5, 55.1, 47.3, 38.0, 29.0, 22.5, 19.4; FIRMS m/z calcd for $C_{41}H_{46}N_2NaO_8S$ [MNa$^+$] 749.2873. found 749.2454.

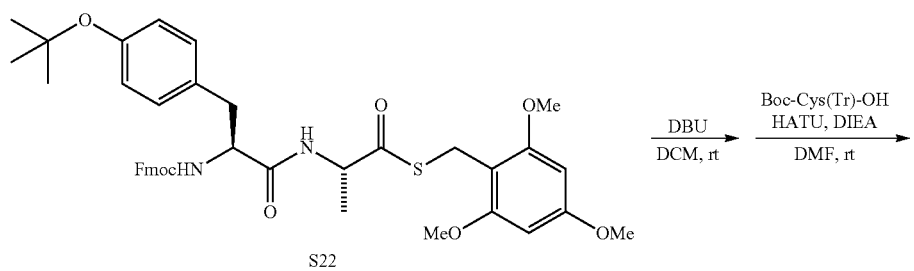

Boc-Cys(Tr)-Tyr(tBu)-Ala-STmb (S23). S22 (249 mg, 0.34 mmol) was subjected to the standard Fmoc deprotection procedure and then coupled to Boc-Cys(Tr)-OH using the standard HATU coupling procedure. The reaction was diluted with DCM (10 mL), and sequentially washed with sat. NaHCO$_3$ (2×10 mL), water (3×15 mL), and brine (10 mL). The organic layer was dried (MgSO$_4$), filtered, and concentrated by rotary evaporation. The crude residue was purified by flash chromatography (1:1 EtOAc/hexanes) to afford S27 as a white solid (167 mg, 51%). HS-Tmb (S20, 28 mg, 38%) was recovered as a by-product, leading us to conclude that significant decomposition of the thioester occurred during the Fmoc deprotection procedure.[6] R$_f$ 0.28 (30% EtOAc/hexanes); $^1$H NMR (300 MHz, CDCl$_3$) δ 7.52-7.15 (15H), 7.05 (d, J=8.5, 1H), 6.83 (d, J=8.5, 1H), 6.63 (d, J=6.4, 2H), 6.48 (d, J=8.1, 2H), 6.09 (s, 2H), 4.69 (d, J=6.7, 1H), 4.58 (p, J=7.3, 2H), 4.19 (d, J=3.7, 2H), 3.79 (s, 3H), 3.77 (s, 6H), 3.02 (dd, J=13.3, 6.1, 1H), 2.55 (dd, J=13.0, 5.2, 1H), 1.38 (s, 9H), 1.31 (s, 9H), 1.25 (d, J=1.8, 3H). $^{13}$C NMR (75 MHz, CDCl$_3$) δ 200.6, 170.3, 170.0, 161.0, 159.3, 154.5, 144.4, 131.1, 130.0, 129.6, 128.2, 127.1, 124.3, 104.5, 90.6, 80.5, 78.4, 67.4, 55.9, 55.4, 55.1, 54.1, 36.8, 33.7, 29.0, 28.3, 22.3, 18.9; HRMS m/z calcd for C$_{53}$H$_{63}$N$_3$NaO$_9$S$_2$ [MNa$^+$] 972.3903. found 972.3837.

H-Cys-Tyr-Ala-SH (21). Solid S23 (39 mg, 0.041 mmol) placed under argon and chilled to 0° C. in an ice-bath. The solid was dissolved in an ice cold solution of TFA (0.600 mL)+DCM (0.150 mL)+Et$_3$SiH (0.250 mL) and stirred into solution. After 6 h, the reaction had reached rt, and HPLC analysis showed the deprotection to be complete. Diagnostic HPLC: isocratic 10% B in A, 2 min, then gradient 10% to 60% B in A over 23 min, 0.6 mL/min; t$_R$: 9.9 min for 21, t$_R$: 20.5 min for H-Cys-Tyr-Ala-STmb (identified by LRMS analysis: m/z calcd for C$_{25}$H$_{33}$N$_3$NaO$_7$S$_2$ [MNa$^+$] 574.2. found 574.2). It was noted that the HPLC peak belonging to 21 had a small shoulder, and despite our best efforts, better resolution could not be obtained by HPLC. MS analysis of the peak showed no MS peaks other than that assigned to 21. This may be an analytical artifact emanating from its polyfunctional nature or indicate that 21 was partially epimerized during the final global deprotection step ($^1$H NMR of all precursors to 21 show no evidence of an epimer). The reaction was partitioned between water (10 mL) and Et$_2$O (2×6 mL). The aqueous layer had trace volatiles removed by brief rotary evaporation, and then the crude product solution was purified by preparative HPLC to afford the TFA salt of 21 as a fluffy white solid (9 mg, 45% yield). HRMS m/z calcd for C$_{15}$H$_{22}$N$_3$O$_4$S$_2$

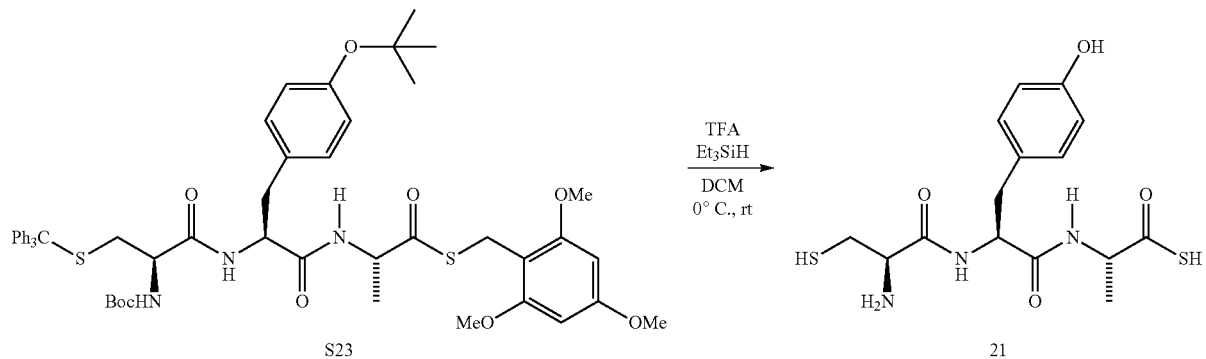

[MH⁺] 379.1052. found 379.0930; m/z calcd for $C_{15}H_{21}N_3NaO_4S_2$ [MNa⁺] 394.0871. found 394.0649.

Id. Aziridine+Thioacid Ligations

Preparation of aqueous buffers. Stock solutions of 2.0 M $Na_2HPO_4$ in water and 1.0 M citric acid in water were combined in proportions to give phosphate-citrate buffer of the desired pH.[8] The urea-phosphate buffer was prepared by dissolving urea and $Na_2HPO_4$ in water, adjusting the pH by adding solid NaOH before bringing the solution up to the desired volume. Using HCl to adjust the pH can lead to undesired decomposition of the aziridine intermediate, thus should be avoided.

i. Reactions to Define Coupling Conditions.

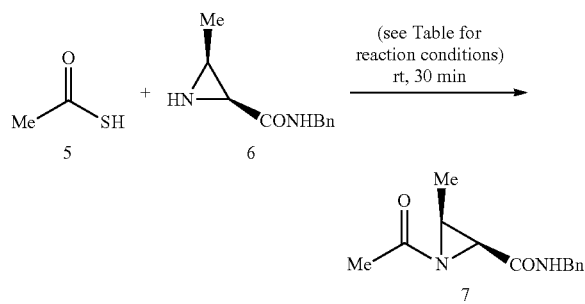

General Procedure for the Metal Mediated Couplings of Thioacetic acid to 6 (Table 3). To a solution of 6 (0.100 mmol) in a 1:1 mixture of DMF and aq. buffer (0.400 mL) was added the appropriate metal salt (1.0 equiv.) and was stirred until homogeneous (in the case of CuCN and CuI, the solution never became homogeneous). To this stirring solution was added AcSH (5, 1.2 equiv.). After 30 minutes, the reaction was filtered through a cotton/celite plug with EtOAc (5 mL) and washed with water (3×5 mL). The organic phase was dried (MgSO₄), filtered, and the solvent was removed under reduced pressure. The crude product (85-97% isolated yield) was analyzed by HPLC without further purification. Replicate experiments of entries 1-4, 6, and 10 were performed under argon in degassed solvents. These experiments yielded no significantly different data than obtained from the experiments conducted under the ambient atmosphere.

TABLE 3

Initial Experiments to Define the Coupling Reaction

| Entry | Metal salt | Solvent | 6[a] | 7[a] | Ring-Opening[a] |
|---|---|---|---|---|---|
| 1 | Cu(OAc)₂•H₂O (100 mol %) | 1:1 DMF-buffer (pH 7.2) | 0% | 100% | 0% |
| 2 | Cu(OAc)₂•H₂O (100 mol %) | 1:1 DMF-buffer (pH 6.2) | 0% | 100% | 0% |
| 3 | Cu(OAc)₂•H₂O (100 mol %) | 1:1 DMF-buffer (pH 5.2) | 0% | 100% | 0% |
| 4 | Cu(OAc)₂•H₂O (100 mol %) | 1:1 DMF-buffer (pH 4.2) | 0% | 100% | 0% |
| 5 | None | 1:1 DMF-buffer (pH 7.2) | 6% | 13% | 81% |
| 6 | AgOAc (100 mol %) | 1:1 DMF-buffer (pH 7.2) | 65% | 35% | 0% |
| 7 | K₃Fe(CN)₆ (100 mol %) | 1:1 DMF-buffer (pH 7.2) | 0% | 50% | 50% |
| 8 | CuI | 1:1 DMF-buffer (pH 7.2) | 45% | 26% | 29% |
| 9 | CuCN | 1:1 DMF-buffer (pH 7.2) | 55% | 28% | 17% |
| 10 | Cu(OAc)₂•H₂O (5 mol %) | 1:1 DMF-buffer (pH 7.2) | 26% | 74% | 0% |

[a]Percentages were determined from the HPLC peak integrations of the crude product mixture. Peak identity was determined by LRMS and/or ¹H NMR analysis.

ii. General Procedures for Table 3.

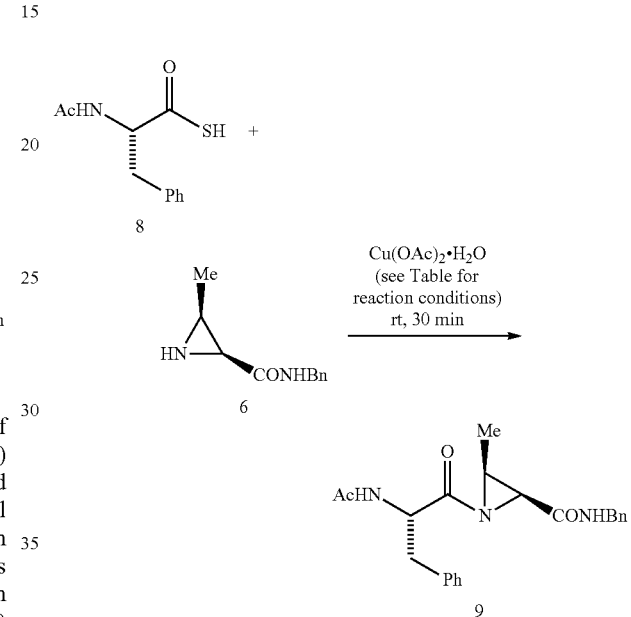

General Procedure for Ac-Phe-SH (or Ac-phe-SH)+H-Azy (Me)-NHBn Ligations (Table 3). To a stirring solution of 6 (0.040 mmol) in the indicated solvent system was Cu(OAc)₂.H₂O (1.0 equiv.) and, if indicated, HOBt (2.0 equiv.). Once the solution became homogeneous, an aliquot of a 0.4 M stock solution of 8 in DMF (1.1 equiv., final reaction concentration 0.1 M) was added, where it was noted the reaction slowly changed color to a dark brown over the next 5 minutes. Thirty minutes after the addition of 8, the reaction was treated with a dropwise addition of aq. NaSH, which precipitated a black solid. Aq. NaSH addition was halted (usually ~0.3 mL) when it had been determined that no more black solid was forming. The heterogeneous mixture was then filtered through a cotton/Celite plug with EtOAc (5 mL). The organic phase was washed with water (5 mL), dried (MgSO₄), filtered, and solvent was removed under reduced pressure to afford a white solid which was analyzed by HPLC and/or ¹H NMR without further purification.

Identification of epi-9. For identification purposes, mixtures of 8 and ent-8 were prepared by an unoptimized version of the synthesis of 8, starting with Ac-Phe-OH(S2) and Ac-phe-OH (ent-S2), respectively. These mixtures were subjected to an unoptimized version of the general procedure for Ac-Phe-SH+H-Azy(Me)-NHBn ligations. For a comparison of ligations using mixtures enriched in 8 vs. mixtures enriched in ent-8 resulting in mixtures of 9 and epi-9, see ¹H NMR data.

iii. Procedures for Ligation/Ring-Opening Reactions

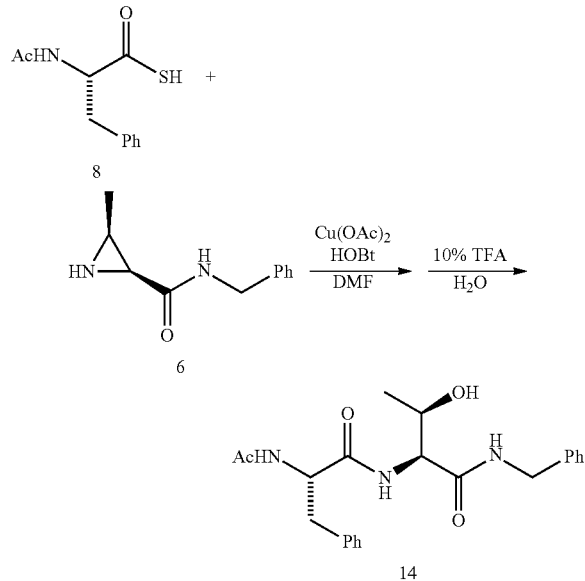

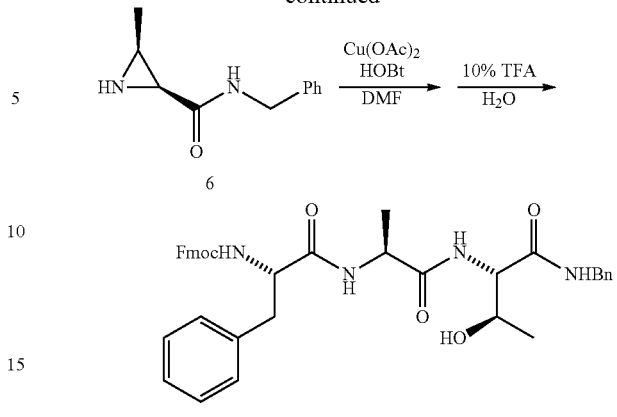

Ac-Phe-Thr-NHBn (10). To a stifling solution of 6 (0.040 mmol) in DMF (0.300 mL) was added Cu(OAc)$_2$.H$_2$O (1.0 equiv.) and HOBt (2.0 equiv.). Once the solution became homogeneous and dark green, 8 (0.125 mL, 0.4 M in DMF, 1.2 equiv.) was added. It was noted the reaction slowly changed color over the next 5 minutes. After 30 minutes, the reaction was charged with 10% aq. TFA. After 1.5 h, the reaction was neutralized by adding sat. NaHCO$_3$ and filtered through cotton/Celite with EtOAc (5 mL). The filtrate was washed with sat. NaHCO$_3$ (5 mL), filtered, and solvent was removed by rotary evaporation. The crude product was purified by flash chromatography (10% iPrOH/DCM) to afford 10 (11 mg, 69% yield) as a white solid. R$_f$ 0.14 (10% iPrOH/DCM); $^1$H NMR (300 MHz, CD$_3$OD) δ 7.40-7.09 (10H), 4.67 (dd, J=9.1, 5.9, 1H), 4.37 (s, 2H), 4.29 (d, J=3.7, 1H), 4.21 (dd, J=6.4, 3.7, 1H), 3.13 (dd, J=17.2, 8.6, 1H), 2.91 (dd, J=13.9, 9.0, 1H), 1.90 (s, 3H), 1.14 (d, J=6.3, 3H); $^1$H NMR (600 MHz, DMSO-d$_6$) δ 8.18 (d, J=8.2 Hz, 1H), 8.08 (t, J=6.1 Hz, 1H), 7.81 (d, J=8.6 Hz, 1H), 7.33-7.17 (9H), 7.15 (t, J=7.1 Hz, 1H), 4.92 (d, J=4.9 Hz, 1H), 4.59 (ddd, J=10.1, 8.4, 4.4 Hz, 1H), 4.28 (overlapped dd, 2H), 4.16 (dd, J=8.6, 3.7 Hz, 1H), 4.05 (complex, overlapped ddt, 1H), 3.01 (dd, J=14.0, 4.3 Hz, 1H), 2.74 (dd, J=14.0, 10.3 Hz, 1H), 1.73 (s, 3H), 1.01 (d, J=6.4 Hz, 3H). $^{13}$C NMR (150.8 MHz, DMSO-d$_6$) δ=172.4, 170.7, 170.0, 162.2, 140.0, 138.8, 129.8, 128.8, 128.7, 127.7, 127.3, 67.0, 59.1, 54.6, 23.1, 20.8; HRMS m/z calcd for C$_{22}$H$_{28}$N$_3$O$_4$ [MH$^+$] 398.2080. found 398.2201; m/z calcd for C$_{22}$H$_{27}$N$_3$NaO$_4$ [MNa$^+$] 420.1899. found 420.2065.

Fmoc-Phe-Ala-Thr-NHBn (16). To a solution of 6 (4.1 mg, 0.022 mmol)+Cu(OAc)$_2$.H$_2$O (4.6, mg, 0.023 mmol) in DMF (0.177 mL) was added HOBt (0.023 mL, 2.00 M in DMF, 0.042 mmol). To the stirring dark green solution was added 15 (10 mg, 0.021 mmol). The reaction color changed to yellow and eventually a very dark brown over the course of 10 minutes. This aziridine intermediate was not detected by analytical HPLC, but was identified by LRMS analysis of the crude reaction mixture (m/z calcd for C$_{38}$H$_{38}$N$_6$NaO$_6$ [MNa$^+$] 653.3. found 653.4). After stirring for 3 h (6 was not detected by LRMS after 1.5 h), the reaction was charged with a solution of TFA (0.060 mL)+H$_2$O (0.500 mL). After 3 h, the reaction was diluted with EtOAc (5 mL) and washed with H$_2$O (3 mL). The organic layer was dried (MgSO$_4$), filtered, and had solvent removed under reduced pressure to afford crude 16 (11.5 mg, 84% yield). HPLC analysis of this crude product determined that the epimerization of this coupling/ring-opening process was 5% (epi-16 was identified by a HPLC co-injection with an authentic sample; see below). The crude product was purified by preparative HPLC (in this case, the HPLC solvent was removed by rotary evaporation, precipitating the product. The product was extracted in DCM and solvent was removed under reduced pressure) to afford 16 as a white solid (9.8 mg, 72% yield) HPLC: gradient 50% to 70% MeCN in H$_2$O over 20 min, 0.6 ml/min; t$_R$: 10.1 min; $^1$H NMR (600 MHz, DMSO-d$_6$) δ 8.37 (d, J=7.1 Hz, 1H), 8.20 (t, J=5.7 Hz, 1H), 7.93 (d, J=7.3 Hz, 1H), 7.87 (d, J=7.1 Hz, 2H), 7.68-7.57 (m, 3H), 7.48 (t, J=7.5 Hz, 12H), 7.43-7.14 (m, 4H), 4.94 (d, J=5.1 Hz, 1H), 4.43-4.37 (m, 2H), 4.32-4.26 (m 3H), 4.19 (dd, J=8.3, 3.6 Hz, 1H), 4.16-4.08 (m, 3H), 4.05 (dd, J=10.1, 5.3 Hz, 1H), 3.84-3.80 (m, 1H), 3.01 (dd, J=13.8, 2.8 Hz, 1H), 2.76 (dd, J=13.4, 11.4 Hz, 1H), 1.26 (d, J=7.1 Hz, 3H), 1.04 (d, J=6.2 Hz, 3H).; HRMS m/z calcd for C$_{38}$H$_{40}$N$_4$NaO$_6$ [MNa$^+$] 671.2846. found 671.3943.

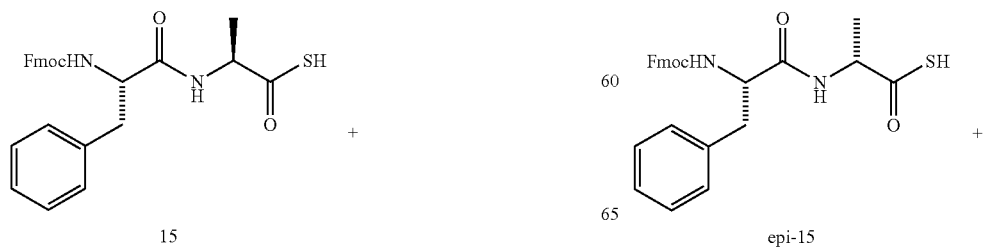

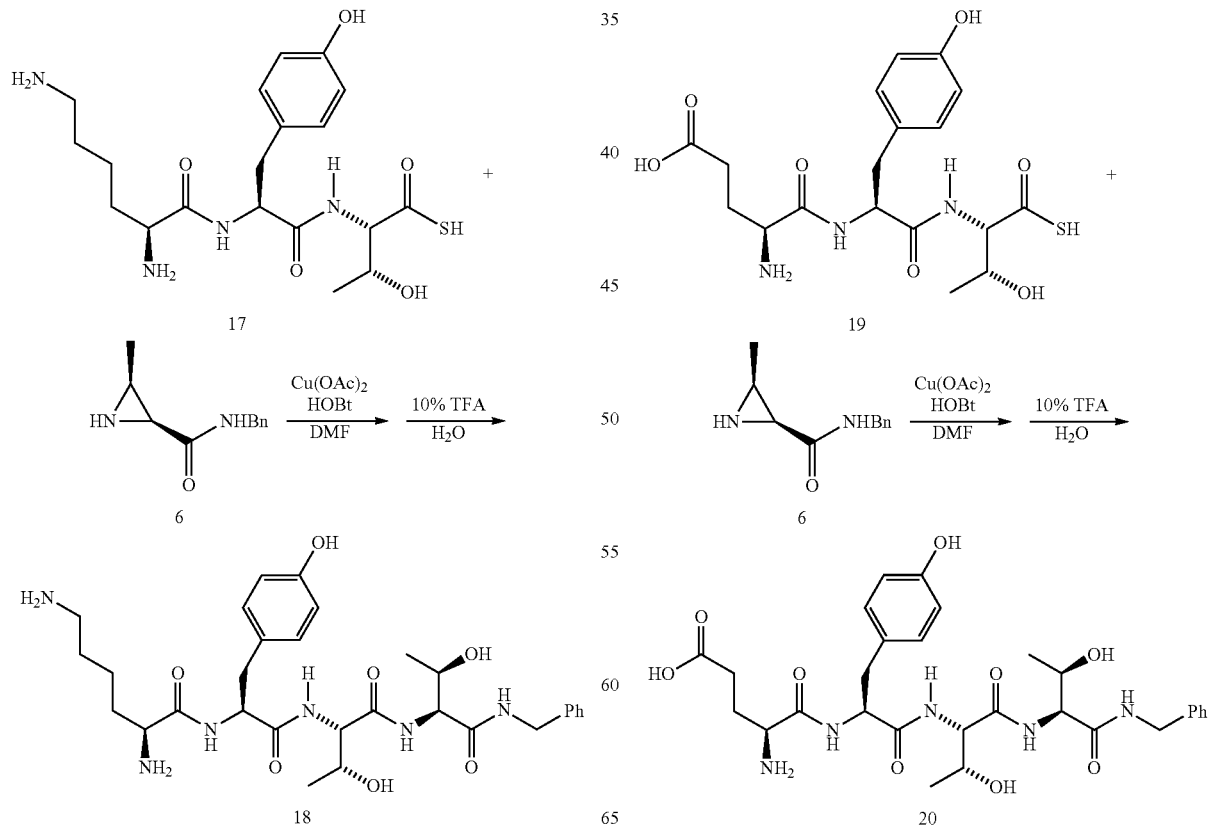

Fmoc-Phe-Ala-Thr-NHBn (epi-16). Following the procedure for preparing Fmoc-Phe-Ala-Thr-NHBn, epi-15 (2.6 mg)+6 (1.1 mg) afforded crude epi-16 (3.7 mg, quant.). An aziridine intermediate identical to that above by LRMS was observed. This crude sample was used to identify the epi-16 found in the crude ligation product of 16 (by analytical HPLC co-injection). HPLC analysis of this crude product determined that the epimerization of this coupling/ring-opening process was 5%. The crude product was purified by preparative HPLC (in this case, the HPLC solvent was removed by rotary evaporation, precipitating the product. The product was extracted in DCM and solvent was removed under reduced pressure) to afford epi-16 as a white solid (2.3 mg, 65% yield). HPLC: gradient 50% to 70% MeCN in $H_2O$ over 20 min, 0.6 mL/min; $t_R$: 8.8 min; HRMS m/z calcd for $C_{38}H_{40}N_4NaO_6$ [MNa$^+$] 671.2846. found 671.3868.

H-Lys-Tyr-Thr-Thr-NHBn (18) (SEQ ID NO: 1). 6 (1.9 mg, 0.010 mmol)+Cu(OAc)$_2$·H$_2$O (2.3 mg, 0.012 mmol)+HOBt (2.8 mg, 0.021 mmol) were dissolved in DMF (0.200 mL) and stirred at rt until homogeneous and dark green. 17 (bis-TFA salt, 8.0 mg, 0.012 mmol) was added to the reaction mixture, which caused the reaction color to change to yellow and eventually a very dark brown over 10 minutes. HPLC monitoring of the reaction showed complete consumption of 6 in favor of H-Lys-Tyr-Thr-Azy(Me)-NHBn after 2.5 h. Although the aziridine intermediate was not isolated, it was observed by HPLC and LRMS analysis: HPLC: isocratic 10% B in A, 2 min, then gradient 10% to 60% B in A over 23 min, 0.6 mL/min; $t_R$: 14.0 min; LRMS m/z calcd for $C_{30}H_{43}N_6O_6$ [MH$^+$] 583.2. found 583.3; m/z calcd for $C_{30}H_{42}N_6NaO_6$ [MNa$^+$] 605.2. found 605.3. The reaction mixture was charged with a solution of water (0.500 mL)+TFA (0.060 mL). After 4 h, the brown heterogeneous mixture was treated with a dropwise addition of aq. NaSH to precipitate a black solid. The reaction was diluted with $H_2O$, and the solid was removed by filtration through a 0.2 μm syringe filter. The filtrate was purified by preparative HPLC to afford 18 as its bis-TFA salt (6.6 mg, 80% yield). HPLC: isocratic 10% B in A, 2 min, then gradient 10% to 60% B in A over 23 min, 0.6 mL/min; $t_R$: 12.3 min; $^1$H NMR (600 MHz, DMSO-d$_6$) δ 9.20 (s, 1H), 8.54 (d, J=7.7, 1H), 8.30 (d, J=8.2, 1H), 8.25 (t, J=5.8, 1H), 8.02 (bs, 3H), 7.67 (bs, 2H), 7.64 (d, J=8.4, 2H), 7.32-7.16 (5H), 7.09 (d, J=7.9, 2H), 6.63 (d, J=7.9, 2H), 5.17 (d, J=4.2, 1H), 4.98 (d, J=3.8, 1H), 4.65 (bs, 1H), 4.35 (dd, J=8.1, 3.5, 1H), 4.28 (d, J=5.8, 1H), 4.22 (dd, J=8.3, 2.5, 1H), 4.08 (d, J=24.3, 2H), 3.70 (bs, 1H), 2.96 (d, J=11.8, 1H), 2.75-2.64 (m, 3H), 1.68 (dd, J=13.5, 6.4, 1H), 1.48 (p, J=7.5, 1H), 1.35-1.23 (m, 2H), 1.05 (d, J=6.2, 3H), 1.01 (d, J=6.0, 3H); HRMS m/z calcd for $C_{30}H_{45}N_6O_7$ [MH$^+$] 601.3350. found 601.3032; m/z calcd for $C_{30}H_{44}N_6NaO_7$ [MNa$^+$] 623.3169. found 623.2794.

H-Glu-Tyr-Thr-Thr-NHBn (SEQ ID NO: 2) (20, General Procedure for Table 2, entries 4-6). 6 (1 equiv.)+Cu(OAc)$_2$.H$_2$O (1 equiv.)+HOBt (2 equiv.) were dissolved in the indicated solvent (0.200 mL) and stirred at rt until dark green (using DMF as a solvent resulted in a homogenous solution, however aq. buffers resulted in fine opaque suspensions). 19 (TFA salt, 1 equiv.) was added to the reaction mixture, which caused the reaction color to change to yellow and eventually a very dark brown over 10 minutes. HPLC monitoring of the reaction showed consumption of 6 in favor of H-Glu-Tyr-Thr-Azy(Me)-NHBn within 2 h. Although the aziridine intermediate was not isolated, it was observed by HPLC and LRMS analysis: HPLC: isocratic 10% B in A, 2 min, then gradient 10% to 60% B in A over 23 min, 0.6 mL/min; t$_R$: 15.2 min; LRMS m/z calcd for C$_{29}$H$_{38}$N$_5$O$_8$ [MH$^+$] 584.2. found 584.0; m/z calcd for C$_{29}$H$_{37}$N$_5$NaO$_8$ [MNa$^+$] 606.3. found 606.3). The reaction mixture was directly treated with a solution of water (0.500 mL)+TFA (0.060 mL). When HPLC analysis showed the hydrolysis was complete, the brown heterogeneous mixture was treated with a dropwise addition of aq. NaSH to precipitate a black solid. The reaction was diluted with H$_2$O and the solid was removed by filtration through a 0.2 μm syringe filter. The filtrate was purified by preparative HPLC to afford 20 as its TFA salt (DMF, 69% yield; phosphate-citrate buffer, 71% yield; urea-phosphate buffer, 88% yield). HPLC: isocratic 10% B in A, 2 min, then gradient 10% to 60% B in A over 23 min, 0.6 mL/min; t$_R$: 13.3 min; $^1$H NMR (600 MHz, DMSO-d$_6$) δ 12.27 (s, 1H), 9.18 (s, 1H), 8.53 (d, J=7.9 Hz, 1H), 8.33 (d, J=8.4 Hz, 1H), 8.22 (t, J=6.0 Hz, 2H), 8.02 (d, J=4.3 Hz, 3H), 7.64 (d, J=8.5 Hz, 1H), 7.30-7.15 (5H), 7.10 (d, J=8.5 Hz, 2H), 6.63 (d, J=8.5 Hz, 2H), 5.16 (bs, 1H), 4.95 (bs, 1H), 4.65-4.63 (m, 1H), 4.38 (dd, J=8.4, 4.0 Hz, 1H), 4.28 (d, J=6.2 Hz, 2H), 4.21 (dd, J=8.5, 3.2 Hz, 1H), 4.10 (dd, J=5.7, 3.1 Hz, 1H), 4.06-4.02 (m, 1H), 3.73 (dd, J=10.5, 5.4 Hz, 1H), 2.95 (dd, J=14.0, 3.2 Hz, 1H), 2.65 (dd, J=14.2, 10.6 Hz, 1H), 2.33 (dd, J=8.4, 3.5 Hz, 1H), 2.31 (dd, J=8.1, 3.3 Hz, 1H), 1.92 (dd, J=14.5, 8.0 Hz, 2H), 1.05 (d, J=6.5 Hz, 3H), 1.00 (d, J=6.3 Hz, 3H); HRMS m/z calcd for C$_{29}$H$_{39}$N$_5$O$_9$ [MH$^+$] 602.2826. found 602.2706.

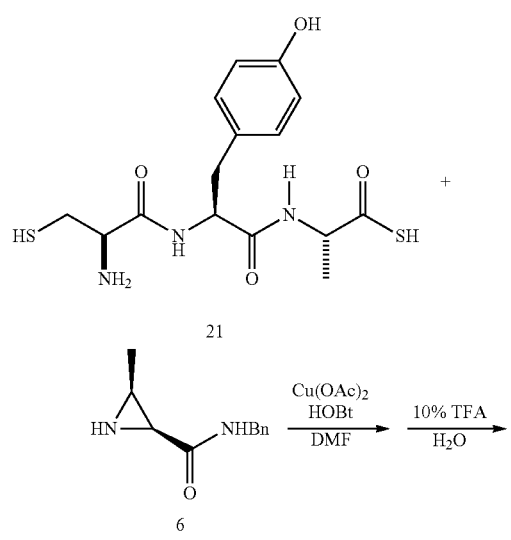

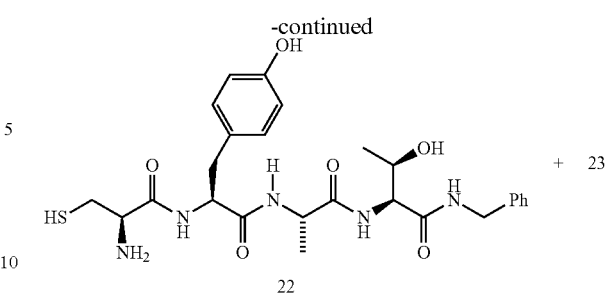

Ligation of H-CYA-SH+H-Azy(Me)-NHBn. 6 (2.5 mg, 0.013 mmol)+Cu(OAc)$_2$.H$_2$O (3.6 mg, 0.018 mmol)+HOBt (4.4 mg, 0.033 mmol) were dissolved in DMF (0.200 mL) and stirred at rt until homogeneous and dark green. 21 OVA salt, 7.6 mg, 0.016 mmol) was added to the reaction mixture, which caused the reaction color to change to black immediately. HPLC monitoring of the reaction showed incomplete consumption of 6 in favor of the disulfide dimer (H-Cys-Try-Ala-Azy(Me)-NHBn)$_2$ after 2 h. Although the aziridine intermediate was not isolated, it could be observed by HPLC and LRMS: HPLC: isocratic 10% B in A, 2 min, then gradient 10% to 60% B in A over 23 min, 0.6 mL/min; t$_R$: 19.7 min; LRMS m/z calcd for C$_{52}$H$_{64}$N$_{10}$NaO$_{10}$S$_2$ [MNa$^+$] 1075.4. found 1075.5. It was noted that (1) there was no LRMS evidence for the presence of the H-Cys-Tyr-Ala-Azy(Me)-NHBn and (2) the reaction mixture for this ligation was significantly more complex than the other examples listed in Table 2. The reaction mixture was charged with a solution of water (0.250 mL)+TFA (0.030 mL). After 2.5 h, when the black heterogeneous mixture was treated with a dropwise addition of aq. NaSH to precipitate a black solid. The mixture was diluted with MeOH (7 mL) and the solid was removed by filtration through a 0.2 μm syringe filter. The filtrate was purified by preparative HPLC to afford 22 as its TFA salt (3.5 mg, 40% yield) and 23 as its bis-TFA salt (3.5 mg, 43% yield). Formation of 22 is believed to have been caused by a reduction of the disulfide dimer by the NaSH that was added to precipitate the copper.

22: HPLC: isocratic 10% B in A, 2 min, then gradient 10% to 60% B in A over 23 min, 0.6 mL/min; t$_R$: 14.2 min; HRMS m/z calcd for C$_{26}$H$_{36}$N$_5$O$_6$S [MH$^+$] 1546.2386. found 546.2922; m/z calcd for C$_{26}$H$_{36}$N$_5$NaO$_6$S [MNa$^+$] 568.2206. found 568.2344.

23: HPLC: isocratic 10% B in A, 2 min, then gradient 10% to 60% B in A over 23 min, 0.6 mL/min; t$_R$: 17.5 min; $^1$H NMR (600 MHz, DMSO-d$_6$) δ 9.20 (s, 1H), 8.72 (bs, 1H), 8.51 (d, J=5.7, 1H), 8.29-8.14 (4H), 7.66 (d, J=8.4, 1H), 7.31-7.23 (6H), 7.20 (t, J=7.1, 2H), 7.05 (d, J=8.2, 1H), 6.63 (d, J=8.4, 2H), 4.94 (bs, 1H), 4.57 (bs, 1H), 4.38 (p, J=7.2 Hz, 1H), 4.32 (dd, J=15.4, 6.2, 1H), 4.26 (dd, J=15.3, 5.8, 1H), 4.23 (dd, J=8.5, 3.6, 1H), 4.03 (s, 2H), 2.96-2.91 (2H), 2.66 (dd, J=13.6, 10.2, 1H), 1.22 (d, J=7.1, 3H), 1.02 (d, J=6.4, 3H). LRMS m/z calcd for C$_{52}$H$_{67}$N$_{10}$O$_{12}$S$_2$ [MH$^+$] 1089.4. found 1089.4; m/z calcd for C$_{26}$H$_{36}$N$_5$NaO$_6$S [MNa$^+$] 1089.4. found 1089.4.

Other products: Crude samples of the reaction mixture, both before and after addition of aq. TFA, were analyzed by LRMS, which gave peaks consistent with 21, 22, and 23 (see above). Minor by-products were tentatively identified as follows: observed before addition of aq. TFA: (S24) m/z calcd for C$_{41}$H$_{50}$N$_6$NaO$_9$S$_2$ [MNa$^+$] 885.3. found 885.4; (S26) m/z calcd for C$_{41}$H$_{50}$N$_6$NaO$_9$S$_3$ [MNa$^+$] 917.3. found 917.4; (S27) m/z calcd for C$_{52}$H$_{64}$N$_{10}$NaO$_{10}$S$_3$ [MNa$^+$] 1114.3. found 1114.2; Observed after aq. I'M addition: (S25) m/z calcd for $C_{41}H_{52}N_8O_{10}S_2$ [MH$^+$] 881.3. found 881.3; (S28) m/z calcd for $C_{52}H_{68}N_{10}O_{12}S_3$ [MH$^+$].

We concluded that these side products emanate from perthioester intermediates. Tam et. al.[9] first disclosed the reaction of thiols and thioacids forming perthiolated products, and the LRMS analysis done on this reaction mixture is consistent with a complex mixture of di-sulfide and tri-sulfide products. An 83% combined yield of the desired products 22 and 23 demonstrates that the aziridine mediated ligation is remarkably faster than the observed side reactions that, presumably, the free thiol causes.

HPLC analysis showed the coupling to be complete (2 h), the reaction mixture was charged with a solution of TFA (0.060 mL)+H$_2$O (0.500 mL). After 3.5 h, the reaction mixture was treated with aq. NaSH to precipitate a black solid. The solid was removed by flushing the reaction mixture through a 0.2 µm syringe filter with MeOH (10 mL). The filtrate had solvent removed by rotary evaporation and was reconstituted in water for purification by preparative HPLC to afford the TFA salt of 25 as a white solid (8.8 mg, 78% yield). HPLC: isocratic 10% B in A, 2 min, then gradient 10% to 60% B in A for 23 min, 0.6 mL/min; $t_R$: 11.1 min; $^1$H NMR (600 MHz, DMSO-d$_6$) δ 9.20

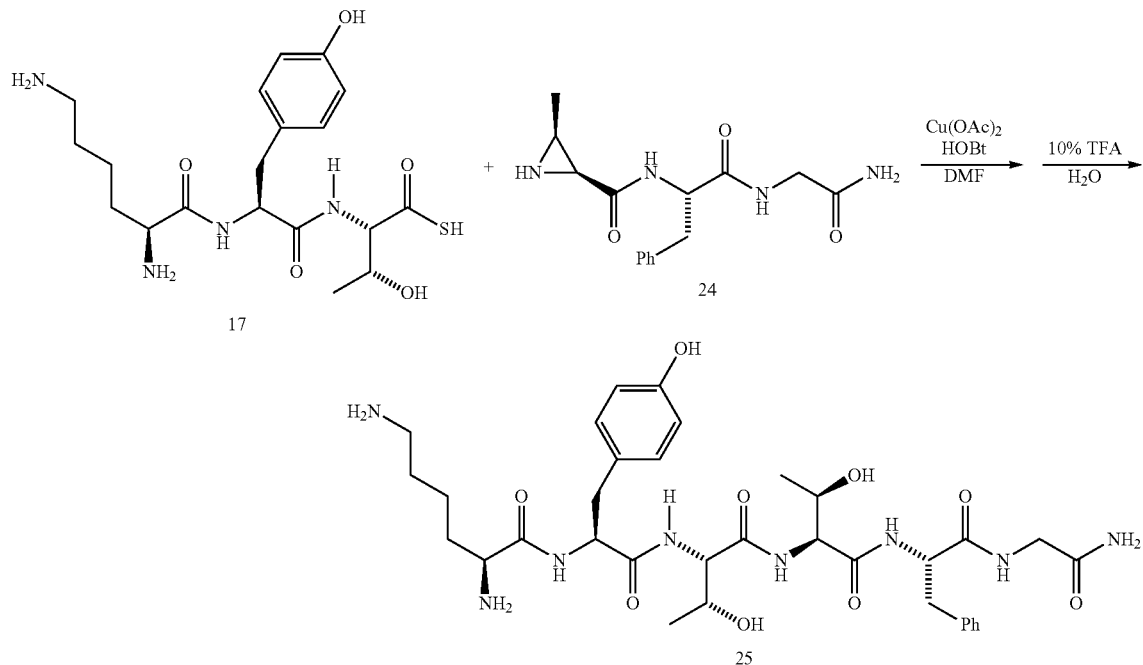

H-Lys-Tyr-Thr-Thr-Phe-Gly-NH$_2$ (25) (SEQ ID NO: 4). 24 (5.0 mg, 0.012 mmol)+Cu(OAc)$_2$.H$_2$O (2.5 mg, 0.013 mmol)+HOBt (3.4 mg, 0.025 mmol) were dissolved in DMF (0.200 mL) and was stirred at rt until homogeneous and dark green. To this solution was added 17, which caused the reaction to change to a dark brown over the next 15 minutes. The formation of H-Lys-Tyr-Thr-Azy(Me)-Phe-Gly-NH$_2$ (SEQ ID NO: 6) was observed by HPLC and LRMS analysis: HPLC: isocratic 10% B in A, 2 minutes, then gradient 10% to 60% B in A over 23 min, 0.6 mL/min; $t_R$: 12.6 min; LRMS m/z calcd for $C_{34}H_{49}N_8O_8$ [MH$^+$] 697.4. found 697.5; m/z calcd for $C_{34}H_{50}N_8NaO_9$ [MNa$^+$] 719.4. found 719.6. When (s, 1H), 8.53 (d, J=8.1, 1H), 8.26 (d, J=8.4, 1H), 8.19 (t, J=5.8, 1H), 8.01 (d, J=7.5, 4H), 7.65 (s, 3H), 7.58 (d, J=8.1, 2H), 7.26-7.03 (m, 9H), 6.63 (d, J=8.5, 2H), 5.07 (d, J=4.5, 1H), 4.97 (d, J=5.0, 1H), 4.69-4.61 (m, 1H), 4.49 (td, J=8.4, 5.3, 1H), 4.32 (dd, J=8.4, 3.8, 1H), 4.21 (dd, J=8.1, 3.9, 1H), 4.03 (qd, J=10.5, 5.5, 2H), 3.70 (bs, 1H), 3.64 (dd, J=16.8, 6.1, 1H), 3.55 (dd, J=16.8, 5.6, 1H), 3.04 (dd, J=14.0, 5.1, 1H), 2.97 (dd, J=14.2, 3.5, 1H), 2.81 (dd, J=13.9, 8.8, 1H), 2.71 (bs, 2H), 2.67 (dd, J=14.5, 10.5, 1H), 1.68 (dd, J=14.4, 7.1, 2H), 1.48 (p, J=7.5, 2H), 1.35-1.22 (m, 2H), 1.00 (d, J=6.3, 3H), 0.99 (d, J=6.3, 3H); HRMS m/z calcd for $C_{34}H_{51}N_8O_9S$ [MH$^+$] 715.3779. found 715.3059.

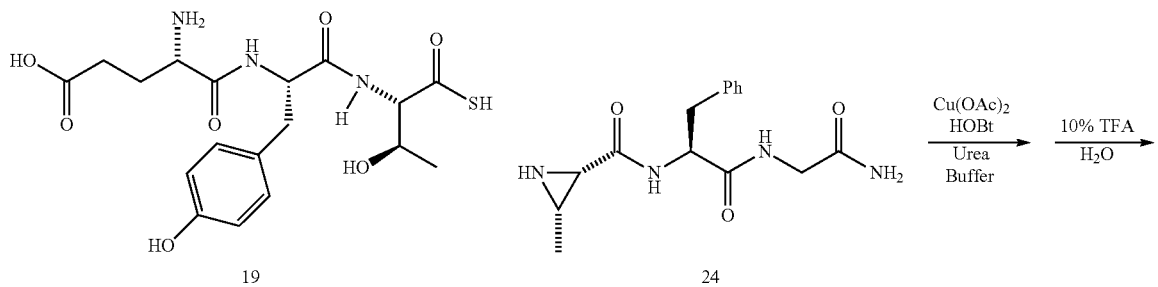

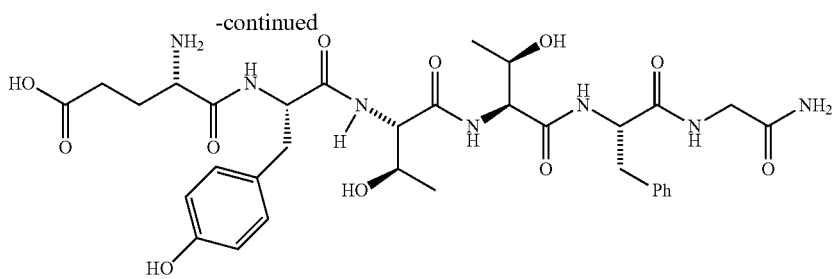

26

H-Glu-Tyr-Thr-Thr-Phe-Gly-NH$_2$ (26) (SEQ ID NO: 5). 24 (5.6 mg, 0.018 mmol)+Cu(OAc)$_2$ (0.019 mmol from an aq. stock solution)+HOBt (0.038 mmol from a 2.00M DMF stock solution) were dissolved in buffer (0.105 mL, 8M Urea, 0.1 M Pi, pH 7.53), and was stirred at rt until homogeneous and dark green. To this solution was added 19 (9.9 mg, 0.018 mmol), which caused the reaction to change to a dark brown immediately. The formation of H-Glu-Tyr-Thr-Azy(Me)-Phe-Gly-NH$_2$ (SEQ ID NO: 7) was observed by HPLC and LRMS analysis: HPLC: isocratic 10% B in A, 2 minutes, then gradient 10% to 60% B in A over 23 min, 0.6 mL/min; t$_R$: 13.0 min; LRMS m/z calcd for C$_{33}$H$_{44}$N$_7$O$_{10}$ [MH$^+$] 698.1. found 698.2; m/z calcd for C$_{33}$H$_{43}$N$_7$NaO$_{10}$ [MNa$^+$] 720.4. found 720.4. When HPLC analysis showed the coupling to be complete (2 h), the reaction mixture was charged with a solution of TFA (0.060 mL)+H$_2$O (0.500 mL). After 2 h, the reaction mixture was treated with aq. NaSH to precipitate a black solid. The solid was removed by flushing the reaction mixture through a 0.2 μm syringe filter with MeOH (10 mL). The filtrate had solvent removed by rotary evaporation and was reconstituted in water for purification by preparative HPLC to afford the TFA salt of 26 as a white solid (11.4 mg, 77% yield). HPLC: isocratic 10% B in A, 2 min, then gradient 10% to 60% B in A over 23 min, 0.6 mL/min; t$_R$: 11.3 min; $^1$H NMR (600 MHz, DMSO-d$_6$) δ 9.18 (s, 1H), 8.52 (d, J=7.9 Hz, 1H), 8.29 (d, J=8.5 Hz, 1H), 8.17 (t, J=5.9 Hz, 1H), 8.02-8.00 (m, 4H), 7.61 (d, J=8.1 Hz, 1H), 7.27-7.03 (m, 9H), 6.63 (d, J=8.5 Hz, 2H), 5.06 (s, 1H), 4.93 (s, 1H), 4.68-4.60 (m, 1H), 4.47 (td, J=8.1, 5.4 Hz, 1H), 4.34 (dd, J=8.4, 3.9 Hz, 1H), 4.20 (dd, J=8.1, 3.9 Hz, 1H), 4.06-3.95 (m, 2H), 3.73 (bd, J=5.2 Hz, 1H), 3.63 (dd, J=16.7, 6.0 Hz, 1H), 3.54 (dd, J=16.8, 5.6 Hz, 1H), 3.03 (dd, J=14.1, 5.1 Hz, 1H), 2.95 (dd, J=14.2, 3.2 Hz, 1H), 2.81 (dd, J=13.9, 8.8 Hz, 1H), 2.65 (dd, J=14.2, 10.5 Hz, 1H), 2.34-2.29 (m, 2H), 1.91 (dd, J=14.7, 7.9 Hz, 2H), 0.99 (overlapped d, 6H); HRMS m/z calcd for C$_{33}$H$_{46}$N$_7$O$_{11}$ [MH$^+$] 716.3255. found 716.3186; m/z calcd for C$_{33}$H$_{45}$N$_7$NaO$_{11}$ [MNa$^+$] 738.3075. found 738.2970.

Ie. Synthesis of a Genuine Sample of 14.

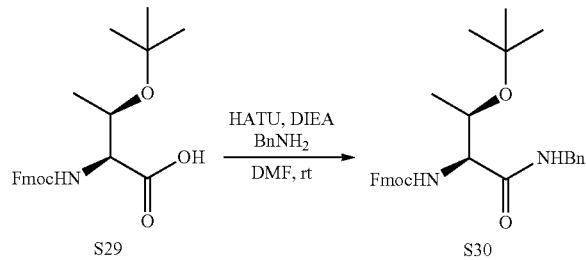

Fmoc-Thr($^t$Bu)-NHBn (S30). Benzylamine (0.270 g, 2.52 mmol) was coupled to Fmoc-Thr($^t$Bu)-OH(S29, 1.00 g, 2.52 mmol) using the standard HATU coupling procedure. The reaction was diluted with Et$_2$O (150 mL), and washed with 10% citric acid solution (60 mL), water (3×60 mL), and brine (60 mL). The organic layer was dried (MgSO$_4$), filtered, and concentrated by rotary evaporation. The crude product was purified using flash chromatography (15% EtOAc/hexanes) to afford S30 as a white solid (1.20 g, 98% yield). R$_f$ 0.53 (1:1 EtOAc/hexanes); $^1$H NMR (300 MHz, CDCl$_3$) δ 7.77 (d, J=7.5 Hz, 2H), 7.61 (d, J=7.4 Hz, 2H), 7.44-7.27 (m, 9H), 6.06 (d, J=4.6 Hz, 2H), 4.50 (dd, J=7.8, 5.7 Hz, 2H), 4.44-4.37 (m, 2H), 4.27-4.14 (m, 3H), 1.24 (s, 9H), 1.04 (d, J=6.5 Hz, 3H); HRMS m/z calcd for C$_{30}$H$_{34}$N$_2$NaO$_4$ [MNa$^+$] 509.2416. found 509.2226.

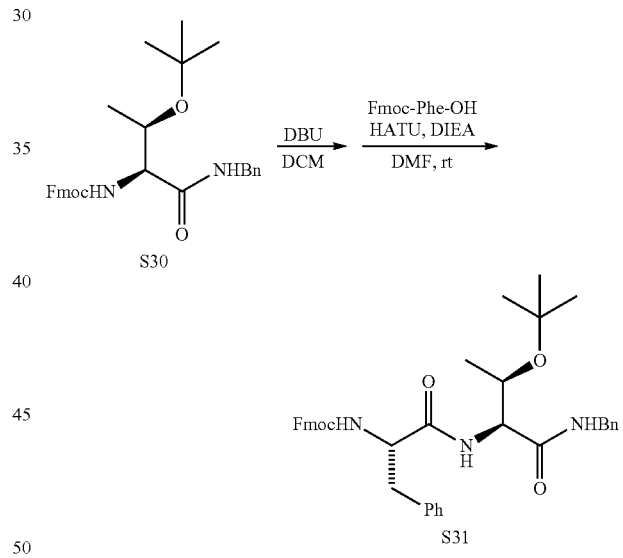

Fmoc-Phe-Thr($^t$Bu)-NHBn (S31). S30 (0.300 g, 0.617 mmol) was subjected to the standard Fmoc deprotection procedure and then coupled to Fmoc-Phe-OH (0.263 g, 0.678 mmol) using the standard HATU coupling procedure. The reaction was diluted with Et$_2$O (90 mL), and washed with 10% citric acid solution (40 mL), water (3×60 mL), and brine (60 mL). The organic layer was dried (MgSO$_4$), filtered, and concentrated by rotary evaporation. The crude product was purified using flash chromatography (30% EtOAc/hexanes) to afford S31 as a white solid (0.344 g, 88% yield over two steps). R$_f$ 0.33 (1:1 EtOAc/hexanes); NMR (300 MHz, CDCl$_3$) δ 7.77 (d, J=7.6 Hz, 2H), 7.53 (dd, J=7.1, 5.2 Hz, 2H), 7.40 (t, J=7.5 Hz, 2H), 7.34-7.10 (14H), 5.30 (d, J=6.2 Hz, 1H), 4.55-4.34 (m, 4H), 4.30-4.08 (m, 4H), 3.11 (d, J=6.4 Hz, 2H), 1.18 (s, 9H), 0.94 (d, J=6.1 Hz, 3H); HRMS m/z calcd for C$_{39}$H$_{43}$N$_3$NaO$_5$ [MNa$^+$] 656.3100. found 656.2769.

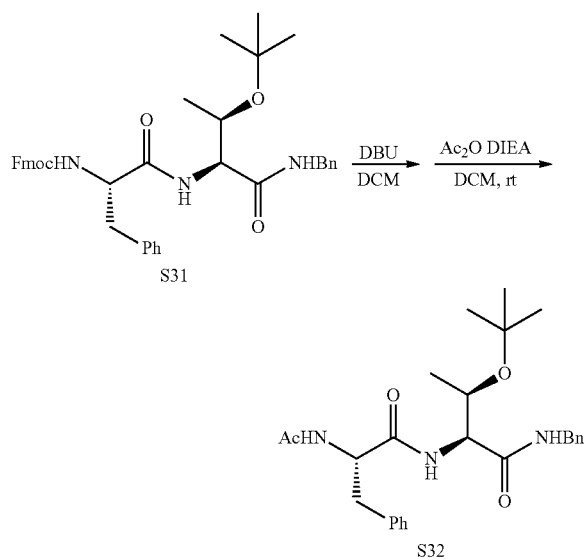

Ac-Phe-Thr(tBu)-NHBn (S32). S31 (0.186 g, 0.293 mmol) was subjected to the standard Fmoc deprotection procedure. The resulting residue was dissolved in a solution of DCM (2 mL), Ac$_2$O (0.060 g, 0.587 mmol), and DIEA (0.076 g, 0.587 mmol) and stirred for 30 minutes at rt. The reaction was diluted with EtOAc (60 mL), washed with water (20 mL), and brine (20 mL). The organic layer was dried (MgSO$_4$), filtered, and concentrated by rotary evaporation. The crude product was purified using flash chromatography (5% MeOH/DCM) to afford S32 as a white solid (0.115 g, 95% yield over two steps). R$_f$ 0.36 (5% MeOH/DCM); $^1$H NMR (300 MHz, CDCl$_3$) δ 7.34-7.13 (10H), 6.88 (d, J=5.8 Hz, 1H), 6.15 (d, J=7.3 Hz, 1H), 4.72 (q, J=6.8 Hz, 1H), 4.51-4.33 (m, 3H), 4.25-4.14 (m, 2H), 3.08 (dd, J=6.7, 4.2 Hz, 2H), 1.97 (s, 3H), 1.16 (s, 9H), 0.96 (d, J=6.3 Hz, 3H); HRMS m/z calcd for C$_{26}$H$_{36}$N$_3$O$_4$ [MH$^+$] 454.2706. found 454.2490; m/z calcd for C$_{26}$H$_{35}$N$_3$NaO$_4$ [MNa$^+$] 476.2525. found 476.2502.

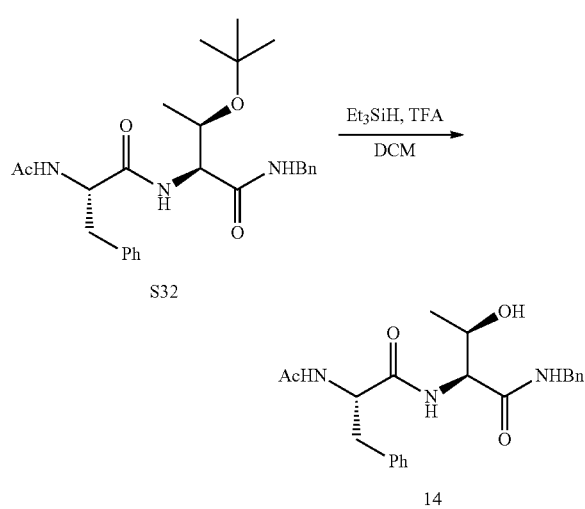

Ac-Phe-Thr-NHBn (14). S32 (0.070 g, 0.154 mmol) was dissolved in an ice cold solution of TFA (0.600 mL)+DCM (0.150 mL)+Et$_3$SiH (0.250 mL) and stirred for 0.5 h. The ice bath was removed and the reaction was allowed to stir at rt for an additional 2 hours. The reaction was diluted with EtOAc (40 mL), and washed with sat. NaHCO$_3$ (2×25 mL), water (25 mL), and brine (25 mL). The organic layer was dried (MgSO$_4$), filtered, and concentrated by rotary evaporation to afford 14 as a white solid (0.050 g, 82% yield). R$_f$ 0.14 (10% iPrOH/DCM); $^1$H NMR (300 MHz, CD$_3$OD) δ 7.33-7.15 (10H), 4.68 (dd, J=9.0, 5.9 Hz, 1H), 4.36 (s, 2H), 4.30 (d, J=3.7 Hz, 1H), 4.21 (dd, J=6.4, 3.7 Hz, 1H), 3.14 (dd, J=13.9, 5.9 Hz, 1H), 2.91 (dd, J=13.9, 9.0 Hz, 1H), 1.89 (s, 3H), 1.14 (d, J=6.4 Hz, 3H). The spectra obtained from this experiment overlaps perfectly with that of 14 prepared from the ligation/ring-opening procedure.

REFERENCE AND NOTES FOR EXPERIMENTAL PROCEDURES (1) a) The experimental procedures for synthesizing 6 and the preparation of trityl aziridine precursor Tr-Azy(Me)-NHBn (S1) from Thr were previously reported by Gin et. al. (see below), however 6 was not isolated and no spectroscopic data reported. b) The synthesis of Tr-Azy(Me)-OH from Tr-Azy(Me)-OBn was performed as reported. See Galonic, D. P.; Ide, N. D.; van der Donk, W. A.; Gin, D. J. Am. Chem. Soc. 2005, 127, 7359-7369 (and references therein).

(2) Goldstein, A. S.; Gelb, M. H. Tetrahedron Lett. 2000, 41, 2797-2800.

(3) Carpino, L. A. J. Am. Chem. Soc. 1993, 115, 4397-4398

(4) There were no efforts made to optimize this experimental procedure.

(5) Barlett, K. N.; Kolakowski, R. V.; Katukojvala, S.; Williams, L. J. Org. Lett. 2006, 8, 823-826

(6) Thioesters are known to be labile during Fmoc-deprotection, thus the low yields on these reactions are not surprising. For a discussion on thioester reactivity in the context of solid phase peptide synthesis, see Crich, D.; Sana, K. J. Org. Chem. 2009, 74, 7383-7388 (and references therein).

(7) Vetter, S. Synth. Comm. 1998, 28, 3219-3223.

(8) McIlvaine, T. C. J. Biol. Chem. 1921, 49, 183-186

(9) Liu, C. F.; Rao, C.; Tam, J. P. Tetrahedron Lett. 1996, 37, 933-936.

Example 2

Further Investigations

Two important chemical ligation problems that remain to be solved are (1) the need to develop a general native chemical ligation method that circumvents the N-terminal Cys requirement and (2) the need for chemical ligation methodology that enables the site-specific introduction of modified amino acid residues at the ligation site. The present technology address both of these problems. The chemical tools that result from this research advance the fields of Biology, Medicine, and Nanotechnology in a transformative way.

The aziridine-mediated peptide ligation concept is shown in Scheme 1 above, and initial investigations of the Cu(II)-promoted coupling of peptide thioacids and aziridine-2-carbonyl peptides to give the aziridine-containing peptides is discussed in Example 1. The aziridine-containing peptides are amenable to a suite of ring-opening reactions that exploit their unique reactivity. Aziridine-mediated peptide ligation is applicable to the synthesis of proteins, and smaller peptide systems The potential utility of using an aziridine moiety embedded in the backbone of a peptide as an electrophilic handle for the site-specific modification has been recognized for some time.

However, the difficulty associated with the synthesis and manipulation of unprotected aziridine-2-carbonyl (Azy) containing peptides has limited the full exploration and exploitation of their properties. The problem stems from the relatively labile N-acylated aziridine moiety, which is susceptible to both nucleophilic N-deacylation (leading to cleavage of the peptide backbone) and premature nucleophilic opening of the aziridine ring under native conditions. In order for the aziridine ring-opening process to form the basis for introducing site-specific modifications into a peptide, the opening must be controllable in terms of both timing and selectivity. The Cu(II)-mediated coupling of unprotected peptide thioacids and Azy peptides enables exploitation of the aziridine's reactivity. This attribute (among others) distinguishes the present technology from the prior art.

Wulff's asymmetric catalytic methodology is used to synthesize cis-3-substituted aziridinyl-2-carboxylic acids d2 (Scheme D1) (Lu et al.) This chemistry involves the reaction of ethyl diazoacetate with readily prepared N-dianisylmethyl (DAM)-protected imines d1 to give the N-protected aziridines d2. This asymmetric aziridination is mediated by a catalyst prepared from the VANOL ligand and B(OPh)$_3$. Wulff applied this reaction to both aromatic and aliphatic imines. Lower ee's were observed with simple aliphatic R groups but this problem was resolved in most cases by a single recrystallization of the crude product. The impact of using functionalized R groups is ascertained empirically. (If some aziridinations prove less enantioselective than desired, purification of the diastereomeric aziridine-2-carbonyl terminated peptides is performed downstream.) It was also shown that the DAM protecting group could be removed under carefully defined acidic conditions without unwanted ring-opening. This was true even with a 3-phenyl substituted azidirine, which has the greatest proclivity for this side reaction. In the case where R is aliphatic, the DAM group could also be removed by hydrogenolysis. It was further demonstrated that free amines such as d3 could be reprotected with a Boc or an Fmoc group to give the differentially protected cis-3-substituted aziridinyl-2-carboxylic acid d4. Others have shown that selective hydrolysis of an ethyl ester in the presence of an Fmoc group can be achieved using Me$_3$SnOH.

Scheme D1

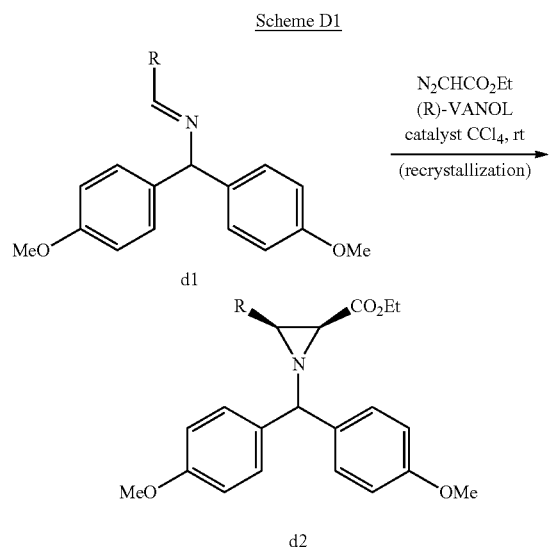

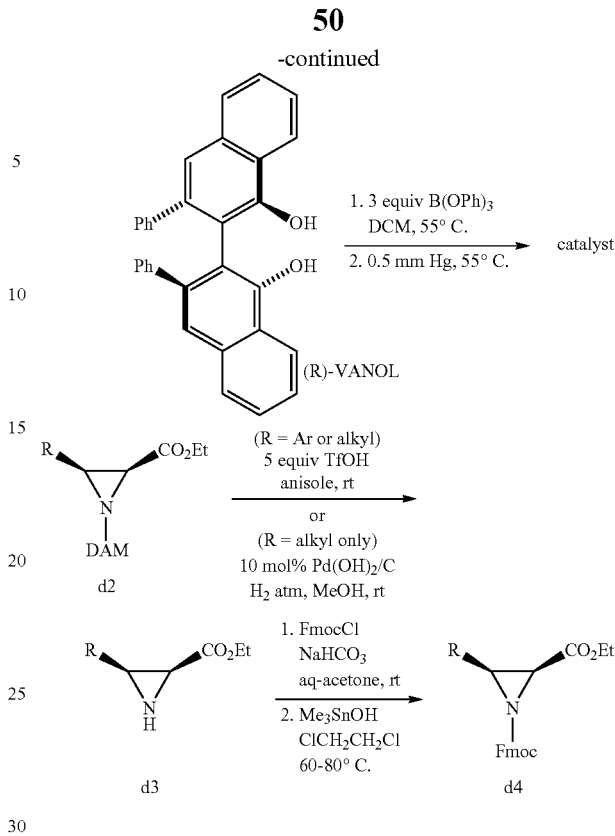

Zwanenburg's method is used to synthesize the corresponding trans-3-substituted aziridinyl-2-carboxylic acids d6 (Scheme D2) (Legters A and B) This method involves nucleophilic opening of the trans-3-substituted oxirane-2-carboxylate esters d5 with azide followed by Staudinger reduction and stereospecific cyclization. The enantiomerically-enriched epoxides d5 are available via Sharpless asymmetric epoxidation/oxidation/esterification of the trans allylic alcohols RCH=CHCH$_2$OH. Installation of an Fmoc group and mild ester hydrolysis as described above provides aziridinyl-2-carboxylic acid d7.

Scheme D2

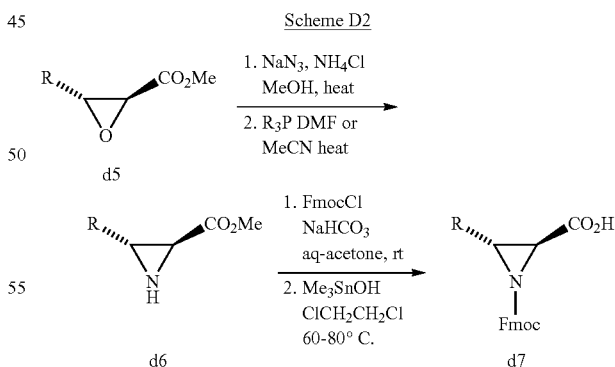

Cis and/or trans versions of the 3-substituted 2-aziridinecarboxylic acids shown in Chart D1 are synthesized using the chemistry described above. The C3 substituents are chosen to correspond to the side chains of the indicated amino acids and, when necessary, are protected with base-labile Fmoc and Fm groups that are compatible with the SPPS strategy to be described below. The aldehyde precursor of the imines (Wulff chemistry) and allylic alcohols (Sharpless chemistry) are prepared by Dess-Martin periodinane oxidation of its alcohol precursor.

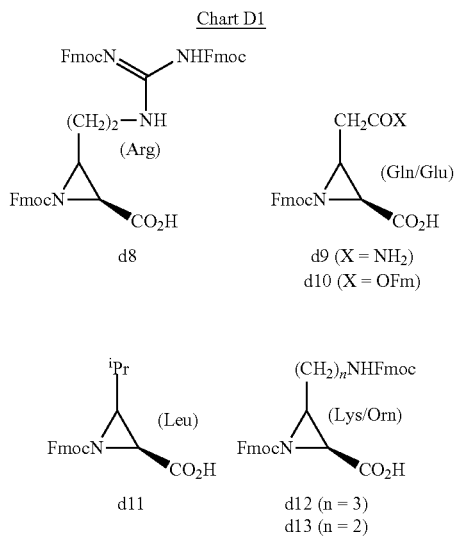

Chart D1

Four trans-3-substituted aziridinyl-2-carboxylic acids are prepared from the tartrate-derived half-ester d16 (Scheme D3). First, the free amine is protected with an Fmoc group to give d17. Steglich esterification with 9-flourenylmethyl alcohol (FmOH) followed by Me₃SnOH mediated hydrolysis of the less hindered methyl ester to give d19. Compounds d20, d21, and d22 are synthesized in a similar fashion but replacing the esterification with an amidation step. There is good precedent for the HATU-mediated coupling of unprotected glycosyl amines to Asp residues.

Synthesis of a Series of Unprotected Aziridinyl-2-Carbonyl Peptides.

To prepare unprotected aziridine-2-carbonyl peptides (Scheme D4), the N-Fmoc 2-aziridinecarboxylic acids d24 are attached to the N-terminus of a support-bound peptide2 d23 that is assembled using established Boc-based SPPS protocols. The main challenge associated with SPPS of aziridine-containing peptides involves the chemoselective removal of protecting groups and cleavage from the resin without premature opening of the aziridine ring This chemoselectivity issue is addressed by synchronizing the protecting group and linker chemistries. Albericio's N[9-(hydroxymethyl)-2-fluorenyl]-based linker is used along with Fmoc- and Fm-based side chain protecting groups. Following the protocol established by Van der Donk and Gin, coupling of the final N-Fmoc 2-aziridinecarboxylic acid to the support-bound peptide is accomplished using HBTU. Their work also showed that the Fmoc group can be removed with 1% DBU/DMF without opening the aziridine ring. Global deprotection and release of the peptide from the resin using these conditions will provide b2 ready for ligation. The product is purified at this stage by reverse phase HPLC followed by lyophilization. This purification protocol worked with the model peptide c17 without opening the aziridine.

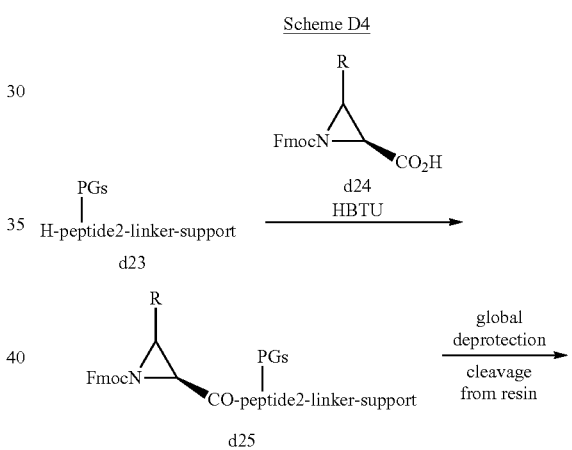

Scheme D4

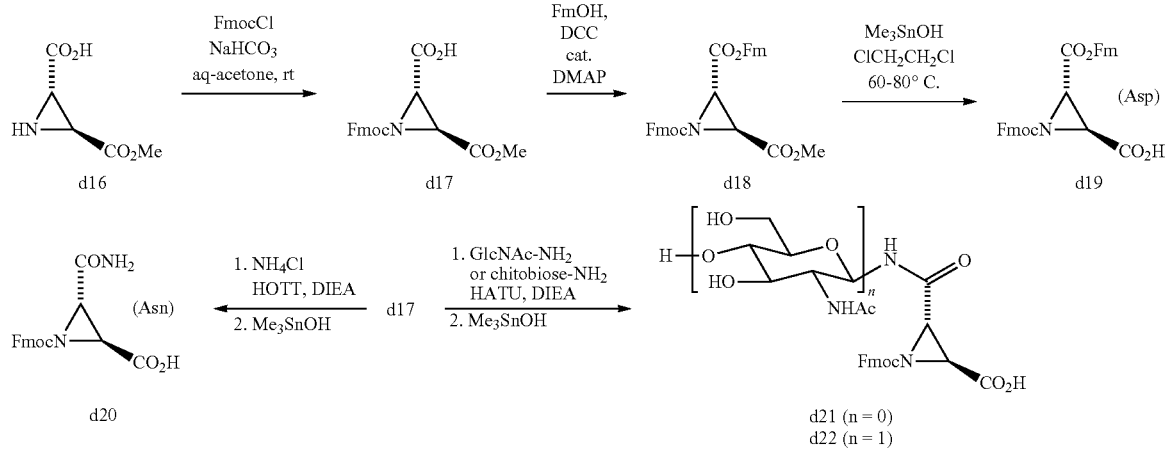

Scheme D3

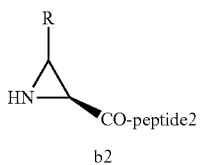

b2

Coupling of Peptide Thioacids and Aziridinyl-2-Carbonyl Peptides Under Native Conditions.

Unprotected peptidyl thioacids corresponding to b 1 are synthesized by one of the following methods. They are prepared in solution via step-wise elongation of Boc-Xaa-SFm esters according to Crich. Unprotected peptide thioacids can also be prepared by SPPS using Danishefsky's strategy (SPPS of protected peptide-OH on a NovaSyn® TGT resin followed by conversion to either STmb or SFm esters and global deprotection/purification). Alternatively, the peptide thioacids can be synthesized directly on a 3-thiopropionyl-linked aminomethyl ChemMatrix resin following Liu's protocol. (Zhang et al.)

The reaction conditions described above are employed (1 equiv. Cu(OAc)$_2$H$_2$O+2 equiv. HOBt in denaturing buffer+DMF as needed). The effect of disulfide reducing agents such as tris(2-carboxyethyl)phosphine (TCEP) are examined in the presence of unprotected Cys residues. Chemoselectivity studies (Scheme D5) are conducted. Coupling of a series of peptide thioacids d26 (Xaa=Arg, Asn, Asp, Cys,* Gln, Glu, *His, Lys,* Ser, and Trp, where * indicates amino acids that have already been examined—see Section C) and aziridine b12 complete the assessment of the compatibility of the coupling reaction with unprotected peptide side chains. Coupling of thioacid d26 and a series of aziridine-2-carbonyl peptides d28 (Zaa=Arg, Asn, Asp, Cys, Glu, Gln, His, Lys, Ser, Thr, Trp, and Tyr) determine the effect of unprotected Zaa residues. Finally, variation of the aziridine 3-substituent R is assessed. The coupling of peptide thioacid c12 (chosen arbitrarily) and aziridine-2-carbonyl dipeptides corresponding to cis and trans versions of d30 probe both the effect of C3 substituent stereochemistry as well as functionality (see Chart D1 and Scheme D2) on the coupling process. Note that the presence of the fixed Phe stereocenter enables chromatographic separation of d30 from any diastereomers resulting from lower enantioselectivity in the Wulf aziridination. N-acyl aziridine products are purified and characterized (RP HPLC followed by lyophilization). Peptides that exhibit poor stability are converted to stable systems (via hydrolytic aziridine ring-opening) as described above.

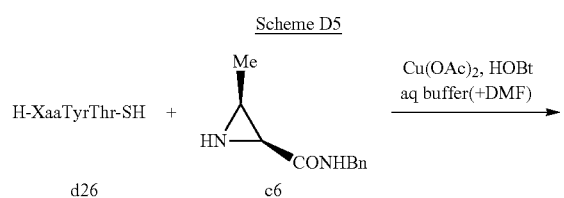

Scheme D5

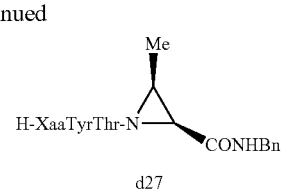

d27

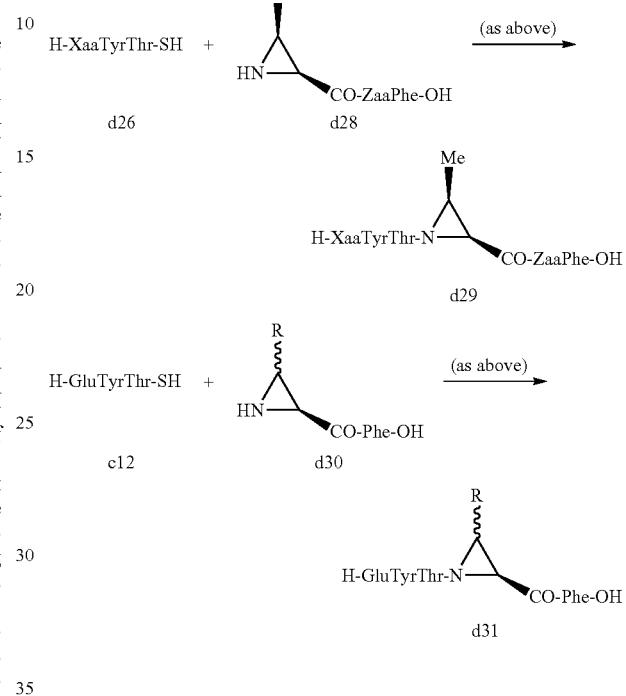

An intramolecular version of the aziridine-mediated ligation is examined (Scheme D6). The target is Hirschmann's cyclic hexapeptide analog of somatostatin. This molecule was also recently synthesized by others. Both of these syntheses required the use of protecting groups in the cyclization step. Aziridine-mediated ligation circumvents this restriction. The hexapeptide precursor d32 is synthesized by merging the aziridine-2-carbonyl peptide and peptide thioacid procedures that were described above. Deprotection using reaction conditions that are compatible with both the aziridine and thioacid moieties provides the cyclization substrate d33. Exposure of this compound to the Cu(II)-promoted coupling conditions produces d34 which is hydrolyzed under standard conditions to give the target d35. Coordination of both the aziridine and thioacid to the Cu(II) ion reduces the entropic barrier to macrocyclization. This example serves as a precedent for a new and general approach to cyclic peptide synthesis.

Scheme D6

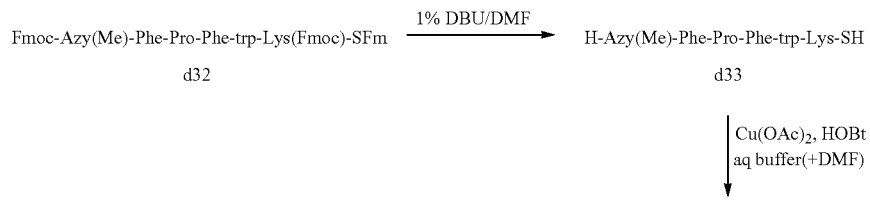

-continued

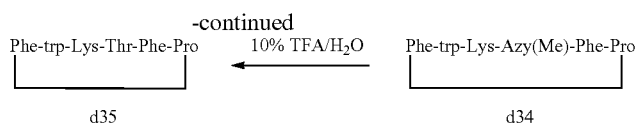

Site-Specific Introduction of Modifications into the Unprotected Peptides via Aziridine Ring-Opening.

N-Acyl aziridines possess a rather unique reactivity profile due to the presence of a tilted amide. As a result this structural feature, N-acyl aziridines are susceptible to both nucleophilic cleavage (base-catalyzed N-deacylation) as well as nucleophilic addition reactions. It is the second reaction pathway that is exploited in a controlled manner by studying a ring-opening of model N-acylated aziridines Ac-Phe-Azy(R)—NHBn using a variety of nucleophiles. C3 selectivity (producing α-peptides) is favored when alkyl and aryl R groups stabilize developing positive charge at C3 in the TS. For the tartrate-derived aziridines, C3-selective conditions are arrived at empirically. (One tactic involves altering the sterics and/or stereoelectronics of the competing ring-openings by temporarily alkylating the preceding amide NH group prior to attaching the aziridine-2-carboxylic acid.) Once the chemistry is established using simple model substrates, the ring-opening reactions are extended to unprotected aziridine-containing peptides.

Reductive ring-opening (Scheme D7) is effected with sodium cyanoborohydride. Precedent for this reaction (with a 3-phenyl substituted aziridine-2-carbonylpeptide) comes from the work of Iqbal. (Prabhakaran et al.) An alternative procedure involves Hantzsch's ester as a (NADH-mimicking) reducing agent. In both reactions, the tilted aziridine amide is activated by protonation. The reductive ring-opening condition is applied to peptide d36. Alternatively, the addition of AcSH followed by hydrolysis and desulfurization using metal-based or metal-free conditions is used. (The regioselective C3-opening of N-acylated 2-carbonylaziridines by thioacids is discussed in the next section.)

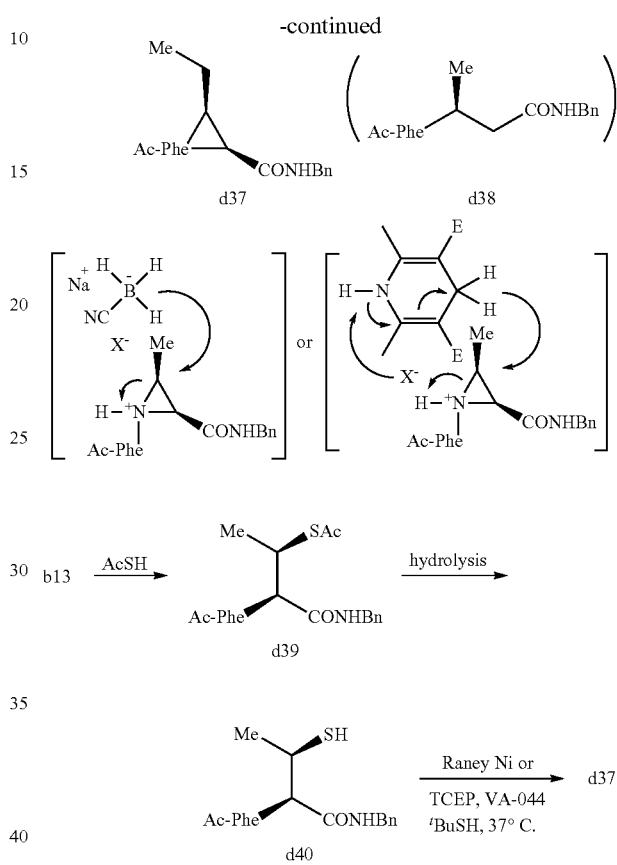

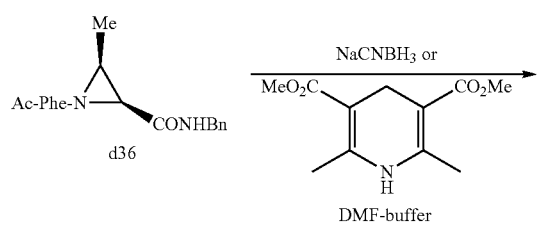

The reductive opening conditions will be applied to the synthesis of the decapeptide H-Leu-Tyr-Arg-Ala-Met-Phe-Arg-Ala-Gln-Lys-OH (d44, Scheme D8) (SEQ ID NO: 8) that was synthesized by Crich using NCL-based methodology. The peptide thioacid d41 and aziridinyl-2-carbonylpeptide d42 are prepared using the methods described above. The decapeptide d44 not only provide a rigorous test for the aziridine-mediated coupling reaction in a typical peptide context but also provides an aziridine substrate that undergoes regioselective reductive ring opening at C3.

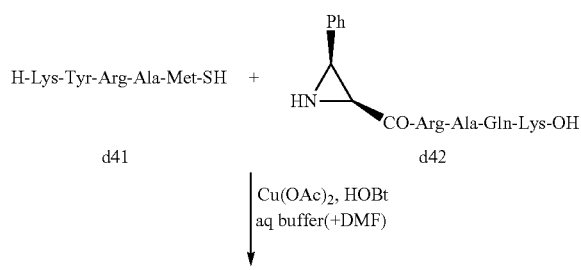

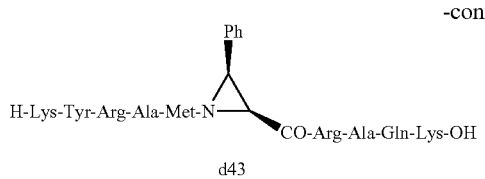

The palmitoylative ring-opening studies (Scheme D9) begin by exposing the model substrate d36 (R=Me) and d46 (R=H) to ring-opening conditions to give the S-palmitoylated products d45 and d47 respectively. The reaction of $C_{15}H_{31}COSH$ with Ac-Azy(Me)-NHBn in DMF+urea gave a 50% yield of the C3-opened product selectively. S-palmitoylative ring-opening proceeds as indicated. The coupling/palmitoylative ring-opening sequence is then applied to longer aziridine containing peptides. One target is the truncated C-terminal N-Ras sequence H-Gly-Thr-Asn-Gly-Cys (Pal)-Met-Gly-Leu-Pro-Cys(Far)-OH (Pal=palmitoyl and Far=farnesyl) (SEQ ID NO: 9). Posttranslational protein lipidation plays an important role in cellular function by providing a reversible means for attaching proteins to membranes. The Ras GTPases are involved in cell cycling, molecular trafficking, and signal transduction. Biosynthesis alone does not provide adequate access to lipidated proteins. The chemical synthesis of lipidated peptides/proteins—particularly differentially polylipidated targets—presents a unique set of challenges because of the orthogonal nature of common lipid linker groups. The aziridine-mediated coupling/palmitoylative ring-opening is a valuable chemical tool for the study of palmitoylation-mediated protein function.

Similar reactions are carried out to achieve site-specific S-ubiquitination of peptides and proteins. A generic scheme for carrying out such reactions is provided in FIG. 1.

The phosphorylative ring-opening studies (Scheme D10) build upon chemistry developed by Okawa and coworkers (Okawa et al.). The model substrates b36 and d46 are exposed to Okawa's conditions to obtain authentic samples of phosphorylated products and confirm the chemoselectivity, regioselectivity and stereoselectivity of the ring-opening. The reaction conditions are optimized so that they may be applied to unprotected aziridine containing peptides. A biologically relevant target, the phosphorylated Checkpoint Kinase 2 (Chk2) fork-head associated (FHA) domain sequence H-Leu-Glu-Thr-Val-Ser-Thr ($PO_3H_2$)-Gln-Glu-Leu-Tyr-Cys-OH (SEQ ID NO: 10) is synthesized. MacMillan has synthesized this phosphopeptide by SPPS and used it to assemble a Thr68-phosphorylated Chk2 (Ser73Cys) "mutant" and demonstrate its phosphate-dependent dimerization. The aziridine-mediated coupling/phosphorylative ring-opening facilitates the synthesis of unprotected phosphorylated proteins by providing a method to phosphorylate specific Ser or Thr residues at the ligation site. This method is thus a valuable tool to help decipher phosphorylation-mediated signaling networks.

Scheme D9

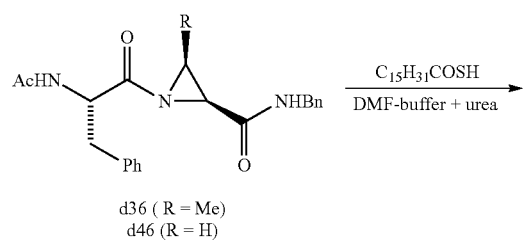

d36 (R = Me)
d46 (R = H)

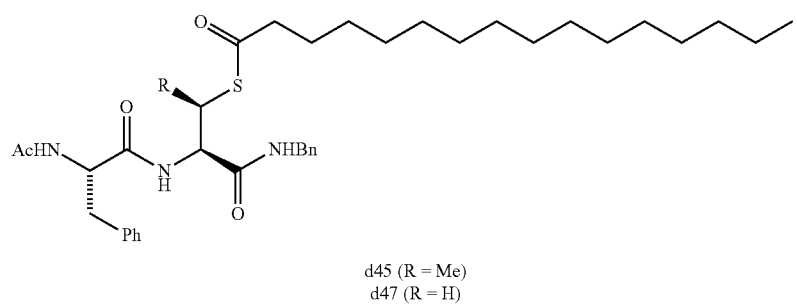

d45 (R = Me)
d47 (R = H)

Scheme D10

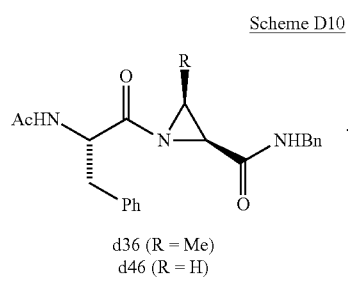

d36 (R = Me)
d46 (R = H)

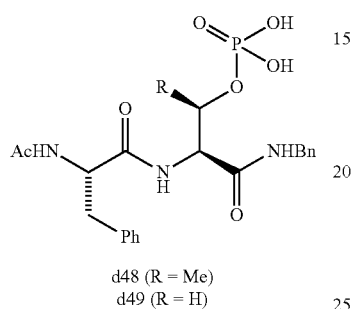

d48 (R = Me)
d49 (R = H)

Two glycosylative ring-opening reactions are explored (Scheme D11). The N-glycan-forming reaction will involve an isocyanide nucleophile adding to an activated aziridine-2-carbonyl peptide. There is precedent for isocyanides opening activated NH aziridines in a "homo-Ugi" sense. There is also a report describing Ugi bioconjugation of proteins in aqueous medium using an unprotected glucosyl isocyanide component. This study defines conditions (variables=solvent, buffer, additive) for the addition of known water-soluble glycosyl isocyanides, and the precursor peracetylated glycosyl isocyanides to the serine-derived aziridine d46. The required hydrolysis of nitrilium d50 is effected without competing aspartimide formation. (Alternatively, the NH functionality is temporarily masked.) This reaction provides an alternative to reductive opening of the tartrate-derived aziridine-2-carbonyl peptides proposed above.

To access O-glycans, the opening of aziridines d36 and d46 by sugar hemiacetals is carried out. This builds on work by Gin which defined conditions to open N-nosyl aziridine-2-carboxamides with (protected) sugar-derived alkoxides (Ryan and Gin). The opening was regioselective and could be tuned to favor either the α- or β-anomer. Reaction variables examined in the present peptide systems include the solvent, additive, as well as the sugar protection status. Aziridine-mediated coupling/glycosylative ring-opening is thus a valuable chemical tool for study of protein glycosylation structure and function.

Scheme D11

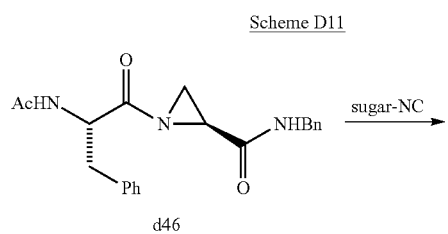

d46

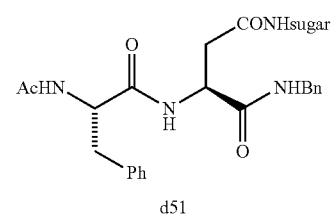

d50

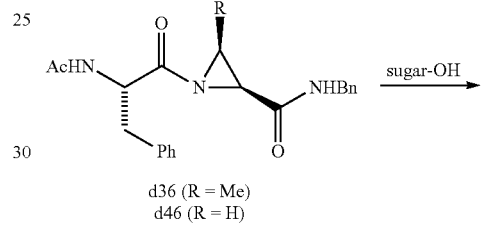

d51

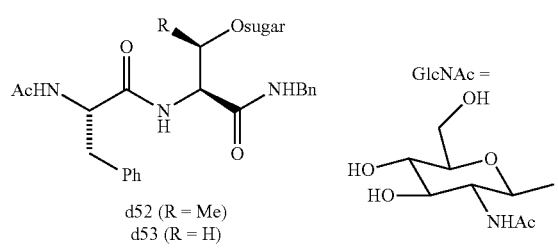

d36 (R = Me)
d46 (R = H)

d52 (R = Me)
d53 (R = H)

GlcNAc =

REFERENCES FOR EXAMPLE 2

[a] Legters, J.; Thijs, L.; Zwanenburg, B. Tetrahedron Lett. 1989, 30, 4881-4884.

[b] Legters, J.; Thijs, L.; Zwanenburg, B. Recl. Tray. Chim. Pays-Bas. 1992, 111, 1-15.

Lu, Z.; Zhang, Y.; Wulff, W. D. J. Am. Chem. Soc. 2007, 129, 7185-7194.

Okawa, K.; Yuki, M.; Tanaka, T. Chem. Lett. 1979, 1085-1086.

Prabhakaran, E. N.; Nandy, J. P.; Shukla, S.; Tewari, A. Das, S. K.; Iqbal, J. Tetrahedron Lett. 2002, 43, 6461-6466.

Ryan, D. A.; Gin, D. Y. J. Am. Chem. Soc. 2008, 130, 15228-15229.

Zhang, X.; Lu, X-W.; Liu, C.-F. Tetrahedron Lett. 2008, 49, 6122-6125.

Example 3

Isomerizative Ring-Opening Studies

Isomerizative ring-opening studies (Scheme D12) also build on known transformations of N-acylated aziridiny-2-carbonyl peptides reported by Okawa (see Example 2. References). The reactions are extended to form specific dehydropeptides in solvents in which the polar substrates are soluble. The resulting ligation/isomerizative process is used to functionalize proteins with nucleophilic reagents. The model substrates b13 and d44 are reacted under known conditions ($Et_3N$ or iodide) in order to obtain authentic samples of dehydropeptides. The conditions are then modified to accommodate longer peptides and native conditions. These reactions likely proceed via an addition/elimination mechanism, so that the use of water-soluble tris[2-carboxyethyl]phosphine (TCEP) leads to the same result under native conditions. The thermodynamically favored (Z)-alkene predominates. The reaction is also tested on longer aziridine-containing peptides.

Scheme D12

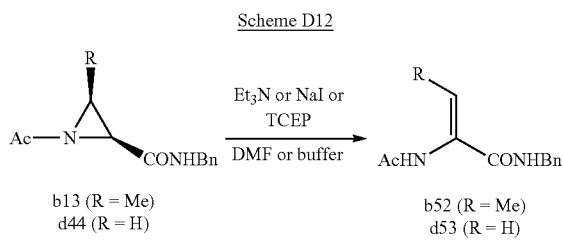

Aziridine-Mediated (Methyl)Lanthionine Ring Formation Under Native Conditions.

The lantibiotics have engendered a great deal of interest because of their therapeutic potential against antibiotic-resistant strains of bacteria. In spite of the considerable effort that has been expended towards the chemical synthesis of lantibiotics, only two total chemical syntheses of natural lantibiotics, nisin and lactocin S, have been reported to date. The aziridine-mediated ligation offers two avenues for (methyl)lanthionine ring formation (Scheme D13). First, the coupling product d54 (from H-Ala-SH+H-Azy(Me)-Pro-Gly-Cys-Val-Ala-OH) (SEQ ID NO: 11) is subjected to the isomerizative ring-opening to give d55, which bears a free Cys residue disposed towards addition to the dehydrobutyrine residue to form d56. This cyclization (using d55 prepared by an alternate route) is known to be stereoselective for the natural L,D-methyllanthionine configuration. However, the nonenzymatic biomimetic approach to (methyllanthionine ring systems is not general in terms of regioselectivity and stereoselectivity. Aziridine-mediate ligation provides an alternative, stereochemically unambiguous approach that circumvents this problem. Peptide d57, which differs from d54 by incorporation of an aziridine derived from D-threonine, is exposed to conditions (DBU/DMF) known to promote direct displacement at C3 of the aziridine by thiolate. The resulting stereospecific ring-opening generates the L,D-methyllanthionine stereochemistry unambiguously. There is precedent for the regioselective and stereoselective intermolecular opening of protected aziridine-containing peptides by thiolates.

Scheme D13

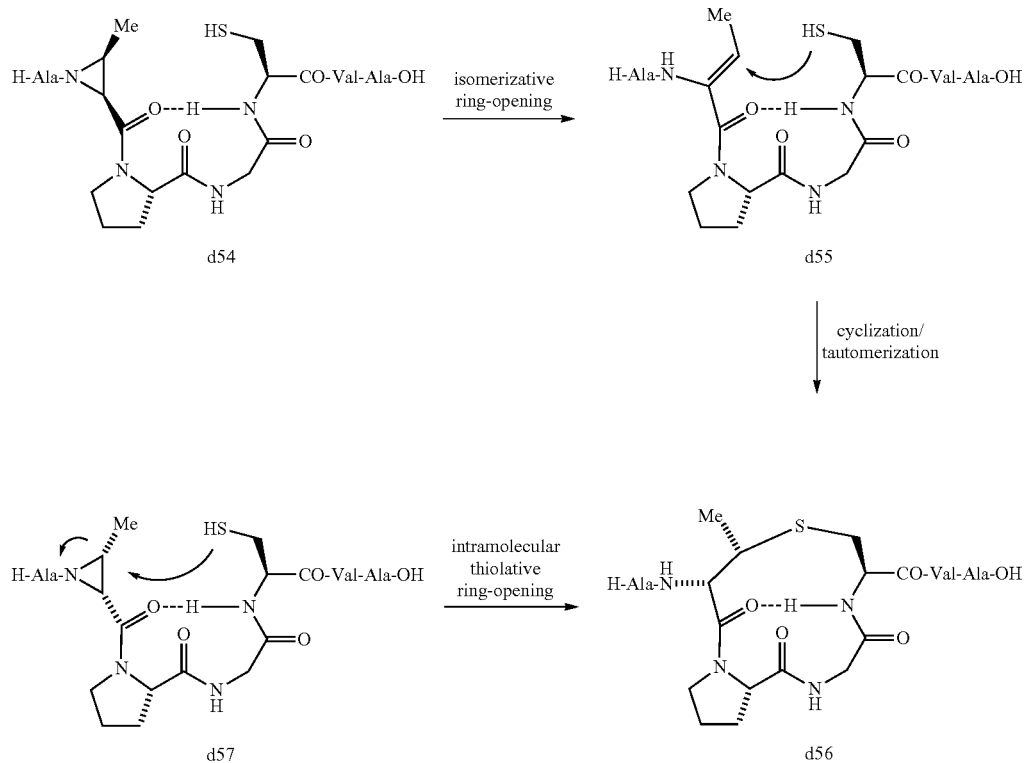

A sequential ligation protocol is developed and applied to the synthesis of a (1-5)-truncated lacticin 3147 A2 (d64, SEQ ID NO: 16). The bis(desmethyl) analogue of this natural product has been synthesized by Vederas and coworkers using a solid-supported synthesis strategy (Ross et al. J. Am. Chem. Soc. 2010, 132, 462-463.) The present aziridine-mediated lantibiotic synthesis begins with the union of peptide thioacid d58 (SEQ ID NO: 12) and the aziridine peptide thioester d59 (SEQ ID NO: 13) to give the lanthionine-containing peptide thioacid d60 (SEQ ID NO: 14) after unmasking of the C-terminal thioacid (Scheme D 14). The coupling/cyclization/deprotection sequence is then re-applied successively to produce d62 (SEQ ID NO: 15) and, finally, d64 (SEQ ID NO: 16) The lanthionine ring is known to be stable to acidic media. The stereochemistry of the lanthionine and methyllanthionine rings is established unambiguously using Vederas' empirical method. The requisite peptide thioacids and aziridine-2-carbonyl peptides are synthesized using the known methodology described above.

The sequential ligation protocol is depicted in Scheme D14 below.

Example 4

Development of a General Aziridinyl Peptide Synthesis

A problem which must be taken into account during development of a general aziridinyl peptide synthesis method is that aziridines do not survive standard acidic global deprotection conditions. This is illustrated in FIG. 2A, which shows undesirable ring opening upon exposure of an aziridinyl peptide to trifluoroacetic acid (TFA). A solution is to employ fluorenylmethyl (Fmoc)-based protecting groups. This is illustrated in FIG. 2B. As can be seen, use of the milder reagent DBU removes protecting groups without ring opening.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

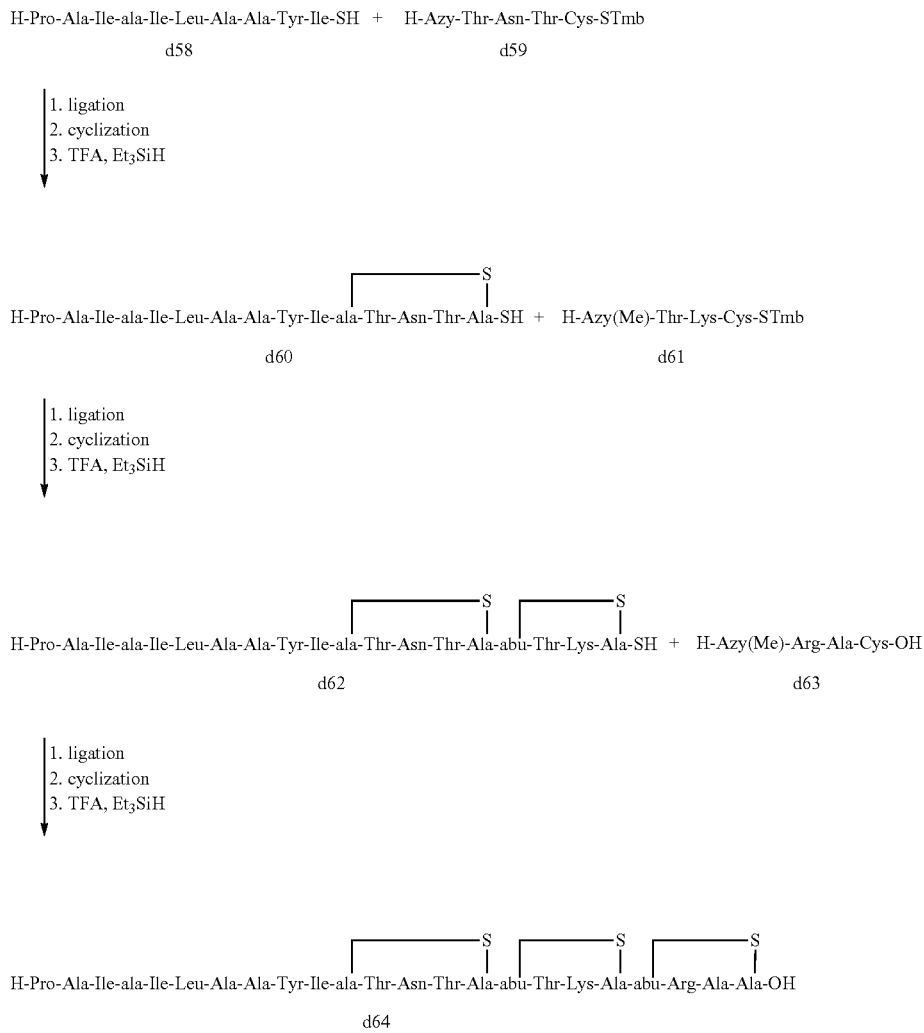

I claim:

1. A method of forming a ligation product, comprising the steps of
   i) reacting, in the presence of Cu(II) ion, a thioacid which includes a first variable group and a terminal SH moiety with an aziridinyl-2-carbonyl compound that comprises a second variable group, and optionally a third variable group substituted at a 3 position of an aziridine ring of said aziridinyl-2-carbonyl compound, said reacting being performed under conditions that form a first ligation product that comprises said aziridine ring; and
   ii) exposing said first ligation product that comprises said aziridine ring to conditions which cause opening of said aziridine ring to form a second ligation product.

2. The method of claim 1, wherein said first variable group is selected from the group consisting of an amino acid, a peptide, a polymer, an organic group, a prodrug, and a detection agent.

3. The method of claim 1, wherein said first variable group is a peptide that is not protected.

4. The method of claim 1, wherein said aziridinyl-2-carbonyl compound comprises said third variable group, and wherein each of said second variable group and said third variable group are independently selected from the group consisting of a peptide, a polymer, a prodrug and a detection agent.

5. The method of claim 4, wherein at least one of said second and third variable groups do not comprise a protecting group.

6. The method of claim 1, wherein said first ligation product that comprises said aziridine ring has a formula $R_1$—CO-1-aziridinyl-2-CO—$R_3$-3-$R_2$, wherein
- R1 is a peptide, a polymer, an organic group, or a detection agent;
- R2 is selected from the group consisting of: hydrogen, alkyl, substituted alkyl, halogen, aryl, aralkyl, substituted aryl, heteroaryl, alkenyl, substituted alkenyl, alkynyl, substituted alkynyl, cycloalkyl, a heterocycle, a heteroatom, a sugar, a glycan, a carbohydrate, a nucleotide, a nucleic acid, a cofactor, a peptide, a prodrug, a polymer, a lipid, an amino acid side chain, and a detection agent; and
- R3 is a peptide, a polymer, a prodrug or a detection agent.

7. The method of claim 1, wherein said conditions which cause opening of said aziridinyl ring include exposing said ligation product to a nucleophile.

\* \* \* \* \*